(12) United States Patent
Fukushima et al.

(10) Patent No.: US 10,120,278 B2
(45) Date of Patent: Nov. 6, 2018

(54) CARBOXYLIC ACID ONIUM SALT, CHEMICALLY AMPLIFIED RESIST COMPOSITION, AND PATTERN FORMING PROCESS

(71) Applicant: Shin-Etsu Chemical Co., Ltd., Tokyo (JP)

(72) Inventors: Masahiro Fukushima, Joetsu (JP); Kazuhiro Katayama, Joetsu (JP)

(73) Assignee: SHIN-ETSU CHEMICAL CO., LTD., Tokyo (JP)

( * ) Notice: Subject to any disclaimer, the term of this patent is extended or adjusted under 35 U.S.C. 154(b) by 0 days.

(21) Appl. No.: 15/488,774

(22) Filed: Apr. 17, 2017

(65) Prior Publication Data

US 2017/0315442 A1  Nov. 2, 2017

(30) Foreign Application Priority Data

Apr. 28, 2016  (JP) .................. 2016-090752

(51) Int. Cl.
*G03F 7/038* (2006.01)
*G03F 7/004* (2006.01)
(Continued)

(52) U.S. Cl.
CPC .......... *G03F 7/0045* (2013.01); *C07C 59/115* (2013.01); *C07C 69/753* (2013.01);
(Continued)

(58) Field of Classification Search
None
See application file for complete search history.

(56) References Cited

U.S. PATENT DOCUMENTS 6,136,500 A   10/2000  Kobayashi et al.
6,485,883 B2  11/2002  Kodama et al.
(Continued)

FOREIGN PATENT DOCUMENTS

JP   11-125907 A   5/1999
JP   11-327143 A  11/1999
(Continued)

OTHER PUBLICATIONS

Office Action dated Jul. 24, 2018, issued in counterpart Korean Application No. 10-2017-0052789, with English translation. (15 pages).

*Primary Examiner* — Martin J Angebranndt
(74) *Attorney, Agent, or Firm* — Westerman, Hattori, Daniels & Adrian, LLP

(57) ABSTRACT

A carboxylic acid onium salt of formula (1) exerts a satisfactory acid diffusion control (or quencher) function. A resist composition comprising the carboxylic acid onium salt can be processed by DUV or EUV lithography to form a resist pattern with improved resolution, reduced LWR and minimal defects after development.

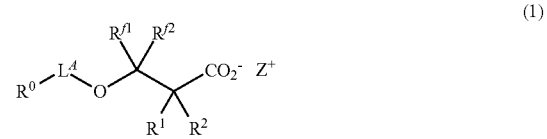

(1)

15 Claims, 6 Drawing Sheets

(51) Int. Cl.
*G03F 7/09* (2006.01)
*G03F 7/16* (2006.01)
*G03F 7/32* (2006.01)
*G03F 7/20* (2006.01)
*G03F 7/38* (2006.01)
*C07C 59/115* (2006.01)
*C07C 69/753* (2006.01)
*C07C 381/12* (2006.01)
*C07D 307/00* (2006.01)
*C07D 493/18* (2006.01)
*G03F 7/11* (2006.01)

(52) U.S. Cl.
CPC .......... *C07C 381/12* (2013.01); *C07D 307/00* (2013.01); *C07D 493/18* (2013.01); *G03F 7/0046* (2013.01); *G03F 7/0048* (2013.01); *G03F 7/0382* (2013.01); *G03F 7/091* (2013.01); *G03F 7/11* (2013.01); *G03F 7/162* (2013.01); *G03F 7/168* (2013.01); *G03F 7/2006* (2013.01); *G03F 7/2041* (2013.01); *G03F 7/322* (2013.01); *G03F 7/325* (2013.01); *G03F 7/38* (2013.01); *C07C 2603/68* (2017.05); *C07C 2603/74* (2017.05)

(56) References Cited

U.S. PATENT DOCUMENTS

| | | |
|---|---|---|
| 6,492,091 B2 | 12/2002 | Kodama et al. |
| 9,221,742 B2 | 12/2015 | Ohashi et al. |
| 2001/0041300 A1* | 11/2001 | Kodama ............... G03F 7/0045 430/170 |
| 2003/0224285 A1* | 12/2003 | Nakao .................. G03F 7/0045 430/270.1 |
| 2004/0033434 A1* | 2/2004 | Ishihara ................ C07C 53/21 430/270.1 |
| 2012/0202153 A1* | 8/2012 | Hatakeyama ......... G03F 7/0045 430/283.1 |
| 2012/0288796 A1* | 11/2012 | Katayama ............ G03F 7/0045 430/285.1 |
| 2013/0101936 A1* | 4/2013 | Taniguchi ............ G03F 7/0045 430/280.1 |
| 2013/0157197 A1* | 6/2013 | Komuro ................ G03F 7/027 430/285.1 |
| 2013/0189619 A1* | 7/2013 | Komuro ................ G03F 7/004 430/270.1 |
| 2014/0255843 A1* | 9/2014 | Kobayashi ............ G03F 7/40 430/270.1 |
| 2015/0086926 A1* | 3/2015 | Ohashi .................. C07C 381/12 430/285.1 |
| 2015/0346600 A1 | 12/2015 | Adachi et al. |
| 2017/0184962 A1* | 6/2017 | Hatakeyama ......... G03F 7/2004 |
| 2017/0184964 A1* | 6/2017 | Hatakeyama ......... G03F 7/0045 |

FOREIGN PATENT DOCUMENTS

| | | | |
|---|---|---|---|
| JP | 2001-281849 A | 10/2001 | |
| JP | 2006-195283 | * 7/2006 | ............. G03F 7/004 |
| JP | 4226803 B2 | 2/2009 | |
| JP | 2002-072481 | * 3/2012 | ............. G03F 7/039 |
| JP | 2012-108447 A | 6/2012 | |
| JP | 2015-54833 A | 3/2015 | |
| JP | 2015-225251 A | 12/2015 | |

* cited by examiner

CARBOXYLIC ACID ONIUM SALT, CHEMICALLY AMPLIFIED RESIST COMPOSITION, AND PATTERN FORMING PROCESS

CROSS-REFERENCE TO RELATED APPLICATION

This non-provisional application claims priority under 35 U.S.C. § 119(a) on Patent Application No. 2016-090752 filed in Japan on Apr. 28, 2016, the entire contents of which are hereby incorporated by reference.

TECHNICAL FIELD

This invention relates to a carboxylic acid onium salt of specific structure, a chemically amplified resist composition comprising the salt, and a pattern forming process using the resist composition.

BACKGROUND ART

While a number of recent efforts are being made to achieve a finer pattern rule in the drive for higher integration densities and operating speeds in LSI devices, DUV and EUV lithography is thought to hold particular promise as the next generation in microfabrication technology. In particular, photolithography using an ArF excimer laser is requisite to the micropatterning technique capable of achieving a feature size of 0.13 µm or less.

The ArF lithography started partial use from the fabrication of 130-nm node devices and became the main lithography since 90-nm node devices. Although lithography using $F_2$ laser (157 nm) was initially thought promising as the next lithography for 45-nm node devices, its development was retarded by several problems. A highlight was suddenly placed on the ArF immersion lithography that introduces a liquid having a higher refractive index than air (e.g., water, ethylene glycol, glycerol) between the projection lens and the wafer, allowing the projection lens to be designed to a numerical aperture (NA) of 1.0 or higher and achieving a higher resolution. While the ArF immersion lithography has entered the commercial stage, the technology still needs a resist material which is substantially non-leachable in water.

In the ArF lithography (193 nm), a high sensitivity resist material capable of achieving a high resolution at a small dose of exposure is needed to prevent the degradation of precise and expensive optical system materials. Among several measures for providing high sensitivity resist material, the most common is to select each component which is highly transparent at the wavelength of 193 nm. For example, polyacrylic acid and derivatives thereof, norbornene-maleic anhydride alternating copolymers, polynorbornene, ring-opening metathesis polymerization (ROMP) polymers, and hydrogenated ROMP polymers have been proposed as the base resin. This choice is effective to some extent in enhancing the transparency of a resin alone.

Sulfonium salts such as triphenylsulfonium nonafuorobutanesulfonate are typically used as the photoacid generator (PAG) because of stability in resist compositions.

Studies have also been made on acid diffusion inhibitors. Amines are typically used as the acid diffusion inhibitor. Many problems associated with line width roughness (LWR) as an index of pattern roughness and pattern profile are left unsolved. Also use of weak acid onium salts as the diffusion inhibitor is under study. For example, Patent Document 1 describes that patterns with minimal roughness can be formed using a compound capable of generating a carboxylic acid having a boiling point of at least 150° C.

Patent Document 2 reports improvements in sensitivity, resolution and exposure margin by the addition of sulfonic acid ammonium salts or carboxylic acid ammonium salts. Also, Patent Document 3 describes that a resist composition for KrF or EB lithography comprising a PAG capable of generating a fluorinated carboxylic acid is improved in resolution and process latitude such as exposure margin and depth of focus. Further, Patent Document 4 describes a positive photosensitive composition for ArF excimer laser lithography comprising a carboxylic acid onium salt. These systems are based on the mechanism that a salt exchange occurs between a weak acid onium salt and a strong acid (sulfonic acid) generated by another PAG upon exposure, to form a weak acid and a strong acid onium salt. That is, the strong acid ($\alpha,\alpha$-difluorosulfonic acid) having high acidity is replaced by a weak acid (alkanesulfonic acid or carboxylic acid), thereby suppressing acid-aided elimination reaction of acid labile group and reducing or controlling the distance of acid diffusion. The onium salt apparently functions as a quencher, that is, acid diffusion inhibitor. However, as the microfabrication technology is currently further advanced, the resist compositions using such weak acid onium salts become unsatisfactory with respect to resolution, roughness, depth of focus and the like, particularly when processed by the ArF immersion lithography. The alkanesulfonic acid salts have a low quencher capability because the acidity is not fully low. The carboxylic acid salts are not only insufficient in the above-referred properties, but also suffer from a leaching problem because they are highly hydrophilic. That is, the salts can be leached in immersion water used in the ArF immersion lithography. Since this leaching has a concern of contaminating the exposure tool and can also cause defects, it is desired to minimize the leaching.

Patent Document 5 discloses an onium salt of fluoroalkanesulfonamide as the weak acid onium salt. When this onium salt is applied to the upcoming generation of ultrafine processing using ArF lithography or ArF immersion lithography, the line width roughness (LWR), indicative of pattern roughness, and resolution are yet short. There is still a need for a weak acid onium salt having improved quencher function. Also Patent Document 6 describes an onium salt of $\alpha,\alpha$-difluorocarboxylic acid as the carboxylic acid onium salt. On use of this onium salt, it can act as an acid generator in some cases because the carboxylic acid resulting from proton exchange with strong acid has an acidity which is not fully low. Because of such low quencher function, LWR and resolution are unsatisfactory.

To comply with the requirement of further miniaturization, there is a demand for a novel acid diffusion inhibitor having a fully low acidity, improved quencher function, and low hydrophilicity.

CITATION LIST

Patent Document 1: JP-A H11-125907 (U.S. Pat. No. 6,136,500)
Patent Document 2: JP-A H11-327143
Patent Document 3: JP-A 2001-281849 (U.S. Pat. No. 6,485,883)
Patent Document 4: JP 4226803 (U.S. Pat. No. 6,492,091)
Patent Document 5: JP-A 2012-108447

Patent Document 6: JP-A 2015-054833

DISCLOSURE OF INVENTION

An object of the invention is to provide a chemically amplified resist composition which is processed by DUV lithography and EUV lithography to form a resist pattern with improved resolution, reduced LWR and minimal defects after development, a carboxylic acid onium salt for use therein, and a pattern forming process using the resist composition.

The inventors have found that a resist composition comprising a carboxylic acid onium salt of specific structure can be processed by lithography to form a resist pattern with improved resolution, reduced LWR and minimal defects after development, and is suited for high accuracy micropatterning.

In one aspect, the invention provides a carboxylic acid onium salt having the formula (1):

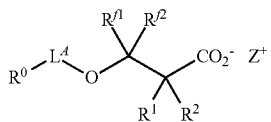

(1)

wherein $R^0$ is hydrogen, or a $C_1$-$C_{20}$ straight, branched or cyclic monovalent hydrocarbon group which may contain a heteroatom; $R^1$ and $R^2$ are each independently hydrogen, or a $C_1$-$C_{20}$ straight, branched or cyclic monovalent hydrocarbon group which may contain a heteroatom, or $R^1$ and $R^2$ may bond together to form a ring with the carbon atom to which they are attached; $R^{f1}$ and $R^{f2}$ are each independently fluorine or a $C_1$-$C_6$ perfluoroalkyl group; $L^A$ is a single bond or forms an ester bond, sulfonate bond, carbonate bond or carbamate bond with the vicinal oxygen atom; $Z^+$ is a sulfonium cation having the formula (2) or an iodonium cation having the formula (3):

$$R^{12}-\overset{\overset{R^{11}}{|}}{S^+}-R^{13} \quad (2)$$

$$R^{14}-I^+-R^{15} \quad (3)$$

wherein $R^{11}$, $R^{12}$ and $R^{13}$ are each independently a $C_1$-$C_{20}$ straight, branched or cyclic monovalent hydrocarbon group which may contain a heteroatom, any two of $R^{11}$, $R^{12}$ and $R^{13}$ may bond together to form a ring with the sulfur atom in the formula, $R^{14}$ and $R^{15}$ are each independently a $C_1$-$C_{20}$ straight, branched or cyclic monovalent hydrocarbon group which may contain a heteroatom.

In a preferred embodiment, $R^{f1}$ and $R^{f2}$ are each independently fluorine or trifluoromethyl. Also preferably, $Z^+$ is a sulfonium cation of formula (2).

In another aspect, the invention provides an acid diffusion inhibitor comprising the carboxylic acid onium salt defined above.

In a further aspect, the invention provides a chemically amplified resist composition comprising (A) the acid diffusion inhibitor defined above, (B) a base resin, (C) a photoacid generator, and (D) an organic solvent. The base resin contains a polymer comprising recurring units having the formula (a) and recurring units having the formula (b).

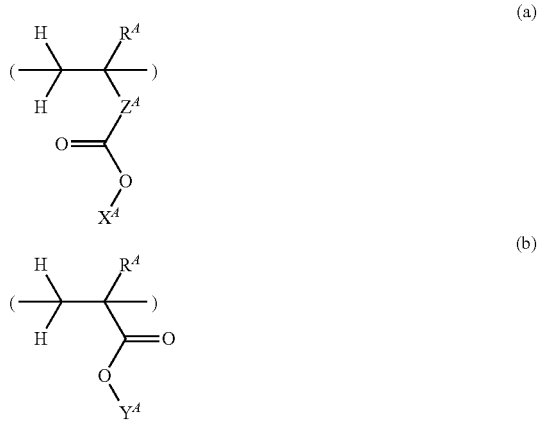

Herein $R^A$ is hydrogen, methyl or trifluoromethyl, $Z^A$ is a single bond, phenylene, naphthylene or (backbone)-C(=O)—O—$Z'$—, $Z'$ is a $C_1$-$C_{10}$ straight, branched or cyclic alkylene group which may contain a hydroxyl moiety, ether bond, ester bond, or lactone ring, or a phenylene or naphthylene group, $X^A$ is an acid labile group, and $Y^A$ is hydrogen or a polar group having at least one structure selected from the group consisting of hydroxyl, cyano, carbonyl, carboxyl, ether bond, ester bond, sulfonate bond, carbonate bond, lactone ring, sultone ring, and carboxylic anhydride.

The polymer may further comprise recurring units of at least one type selected from recurring units having the formulae (c1) to (c3).

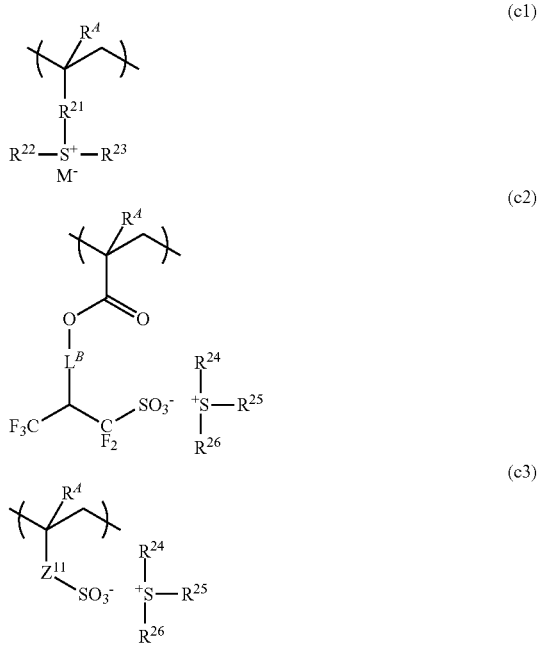

Herein $R^A$ is as defined above; $R^{21}$ is a single bond, phenylene, —O—$R^{31}$—, or —C(=O)—$Z^{22}$—$R^{31}$, $Z^{22}$ is —O— or —NH—, $R^{31}$ is a $C_1$-$C_6$ straight, branched or cyclic alkylene group, $C_2$-$C_6$ straight, branched or cyclic alkenylene group or phenylene group, which may contain a carbonyl (—CO—), ester (—COO—), ether (—O—) or hydroxyl moiety; L⁸ is a single bond or —Z³³—C(=O)—O—, Z³³ is a $C_1$-$C_{20}$ straight, branched or cyclic divalent hydrocarbon group which may contain a heteroatom; $Z^{11}$ is a single bond, methylene, ethylene, phenylene, fluorinated phenylene, —O—R³²—, or —C(=O)—Z⁴⁴—R³²—, Z⁴⁴ is —O— or —NH—, R³² is a $C_1$-$C_6$ straight, branched or cyclic alkylene, $C_2$-$C_6$ straight, branched or cyclic alkenylene or phenylene group, which may contain a carbonyl, ester, ether or hydroxyl moiety; $R^{22}$ to $R^{26}$ are each independently a $C_1$-$C_{20}$ straight, branched or cyclic monovalent hydrocarbon group which may contain a heteroatom, or any two of $R^{21}$, $R^{22}$ and $R^{23}$ may bond together to form a ring with the sulfur atom in the formula, any two of $R^{24}$, $R^{25}$ and $R^{26}$ may bond together to form a ring with the sulfur atom in the formula; and M⁻ is a non-nucleophilic counter ion.

In a preferred embodiment, component (C) is a photoacid generator having the formula (4) or (5).

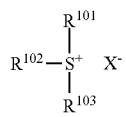

(4)

Herein $R^{101}$, $R^{102}$ and $R^{103}$ are each independently a $C_1$-$C_{20}$ straight, branched or cyclic monovalent hydrocarbon group which may contain a heteroatom, any two of $R^{101}$, $R^{102}$ and $R^{103}$ may bond together to form a ring with the sulfur atom to which they are attached, and X⁻ is an anion selected from the formulae (4A) to (4D):

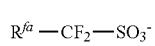

(4A)

(4B)

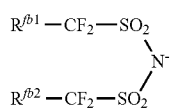

(4C)

(4D)

wherein $R^{fa}$, $R^{fb1}$, $R^{fb2}$, $R^{fc1}$, $R^{fc2}$, and $R^{fc3}$ are each independently fluorine or a $C_1$-$C_{40}$ straight, branched or cyclic monovalent hydrocarbon group which may contain a heteroatom, $R^{fb1}$ and $R^{fb2}$, or $R^{fc1}$ and $R^{fc2}$ may bond together to form a ring with the carbon atoms to which they are attached and the carbon atom therebetween, $R^{fd}$ is a $C_1$-$C_{40}$ straight, branched or cyclic monovalent hydrocarbon group which may contain a heteroatom,

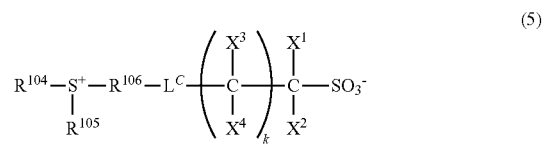

(5)

wherein $R^{104}$ and $R^{105}$ are each independently a $C_1$-$C_{30}$ straight, branched or cyclic monovalent hydrocarbon group which may contain a heteroatom, $R^{106}$ is a $C_1$-$C_{30}$ straight, branched or cyclic divalent hydrocarbon group which may contain a heteroatom, any two of $R^{104}$, $R^{105}$ and $R^{106}$ may bond together to form a ring with the sulfur atom to which they are attached, $L^C$ is a single bond, ether bond, or a $C_1$-$C_{20}$ straight, branched or cyclic divalent hydrocarbon group which may contain a heteroatom, $X^1$, $X^2$, $X^3$ and $X^4$ are each independently hydrogen, fluorine or trifluoromethyl, with the proviso that at least one of $X^1$, $X^2$, $X^3$ and $X^4$ is a substituent other than hydrogen, and k is an integer of 1 to 3.

The resist composition may further comprise (E) a nitrogen-containing compound and (F) a surfactant which is insoluble or substantially insoluble in water and soluble in alkaline developer and/or a surfactant which is insoluble or substantially insoluble in water and alkaline developer.

In a still further aspect, the invention provides a pattern forming process comprising the steps of applying the chemically amplified resist composition defined above onto a substrate, prebaking to form a resist film, exposing the resist film to KrF excimer laser, ArF excimer laser, EB or EUV through a photomask, baking, and developing the exposed resist film in a developer.

Typically, the exposing step is by immersion lithography wherein a liquid having a refractive index of at least 1.0 is interposed between the resist film and a projection lens. The pattern forming process may further comprise the step of forming a protective film on the resist film, and in the immersion lithography, the liquid is interposed between the protective film and the projection lens.

Advantageous Effects of Invention

Since the carboxylic acid onium salt exerts a satisfactory acid diffusion control (or quencher) function, the inventive resist composition comprising the same enables to form a pattern of good profile with a high resolution, low LWR, and improved rectangularity. The salt has a high solubility in resist solvents. When the ArF immersion lithography is applied to the resist composition, there are advantages including least leaching in immersion water and minimal development defects.

BRIEF DESCRIPTION OF ACCOMPANYING DRAWINGS

DESCRIPTION OF EMBODIMENTS

Figure 1:
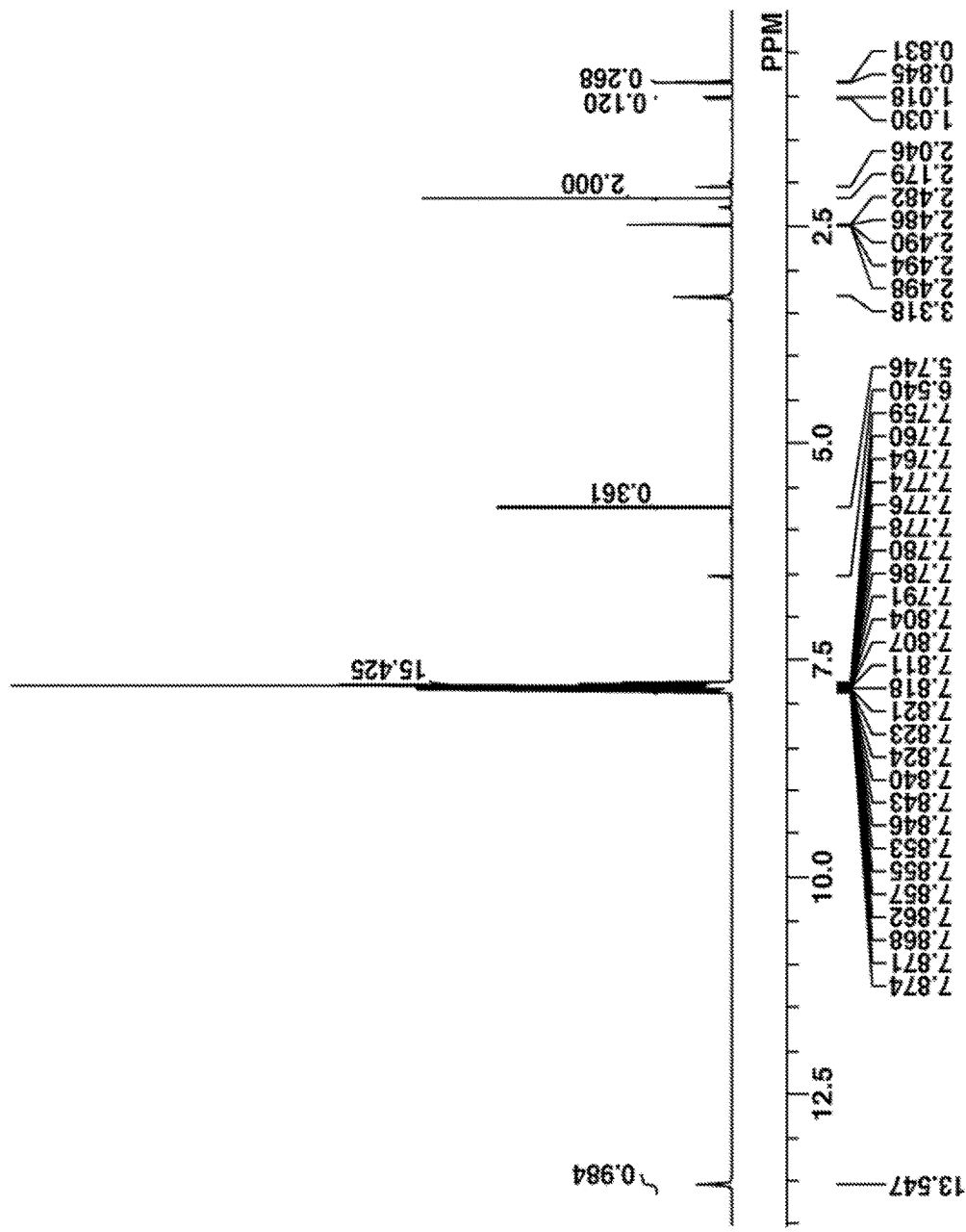
FIG. 1 is a diagram of ¹H-NMR spectrum of the compound obtained in Synthesis Example 1-2.

As used herein, the singular forms "a," "an" and "the" include plural referents unless the context clearly dictates otherwise. The notation (Cn-Cm) means a group containing from n to m carbon atoms per group. In chemical formulae, the broken line denotes a valence bond; Me stands for methyl, Ph for phenyl and Ac for acetyl, The abbreviations and acronyms have the following meaning.
DUV: deep ultraviolet
EUV: extreme ultraviolet
Mw: weight average molecular weight
Mn: number average molecular weight
Mw/Mn: molecular weight distribution or dispersity
GPC: gel permeation chromatography
PEB: post-exposure bake
PAG: photoacid generator
LWR: line width roughness
Onium Salt One embodiment of the invention is a carboxylic acid onium salt having the formula (1).

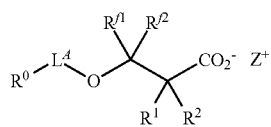

(1)

In formula (1), $R^0$ is hydrogen, or a $C_1$-$C_{20}$ straight, branched or cyclic monovalent hydrocarbon group which may contain a heteroatom. Suitable monovalent hydrocarbon groups include alkyl groups such as methyl, ethyl, propyl, isopropyl, n-butyl, sec-butyl, tert-butyl, tert-pentyl, n-pentyl, n-hexyl, n-octyl, n-nonyl, n-decyl, cyclopentyl, cyclohexyl, 2-ethylhexyl, cyclopentylmethyl, cyclopentylethyl, cyclopentylbutyl, cyclohexylmethyl, cyclohexylethyl, cyclohexylbutyl, norbornyl, tricyclo[5.2.1.0$^{2,6}$]decanyl, adamantyl, and adamantylmethyl, and aryl groups such as phenyl, naphthyl, and anthracenyl. In these groups, one or more hydrogen atom may be replaced by a substituent containing a heteroatom such as oxygen, sulfur, nitrogen or halogen, or a substituent containing a heteroatom such as oxygen, sulfur or nitrogen may intervene between carbon atoms, so that the group may contain a hydroxyl moiety, cyano moiety, carbonyl moiety, ether bond, ester bond, sulfonate (sulfonic acid ester) bond, carbonate bond, lactone ring, sultone ring, carboxylic anhydride or haloalkyl moiety.

In formula (1), $R^1$ and $R^2$ are each independently hydrogen, or a $C_1$-$C_{20}$ straight, branched or cyclic monovalent hydrocarbon group which may contain a heteroatom. Also, $R^1$ and $R^2$ may bond together to form a ring with the carbon atom to which they are attached. Suitable monovalent hydrocarbon groups are as exemplified for $R^0$. When $R^1$ and $R^2$ bond together to form a ring with the carbon atom to which they are attached, suitable rings thus formed include cyclopentane, cyclohexane, norbornane and adamantane rings. In these groups, one or more hydrogen atom may be replaced by a substituent containing a heteroatom such as oxygen, sulfur, nitrogen or halogen, or a substituent containing a heteroatom such as oxygen, sulfur or nitrogen may intervene between carbon atoms, so that the group may contain a hydroxyl moiety, cyano moiety, carbonyl moiety, ether bond, ester bond, sulfonate bond, carbonate bond, lactone ring, sultone ring, carboxylic anhydride or haloalkyl moiety.

In formula (1), $R^{f1}$ and $R^{f2}$ are each independently fluorine or a $C_1$-$C_6$ perfluoroalkyl group. Suitable perfluoroalkyl groups include trifluoromethyl, perfluoroethyl, perfluoroisopropyl, perfluorobutyl, perfluoro-sec-butyl, perfluoro-tert-butyl, perfluoropentyl, and perfluorohexyl. $R^{f1}$ and $R^{f2}$ are preferably fluorine or trifluoromethyl, more preferably trifluoromethyl.

In formula (1), $L^A$ is a single bond or forms an ester bond, sulfonate bond, carbonate bond or carbamate bond with the vicinal oxygen atom.

Preferred structures for the anion moiety of the carboxylic acid onium salt having formula (1) are shown below, but not limited thereto.

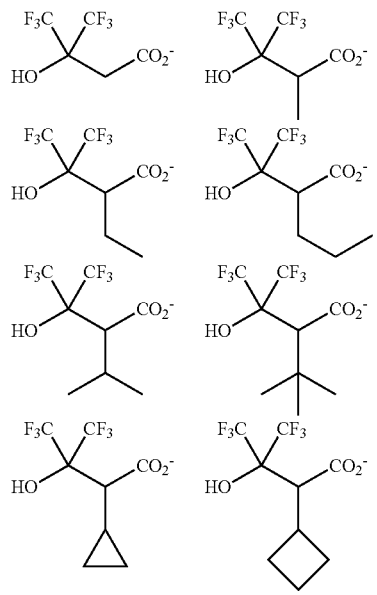

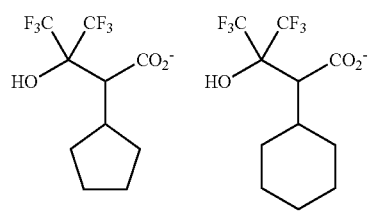

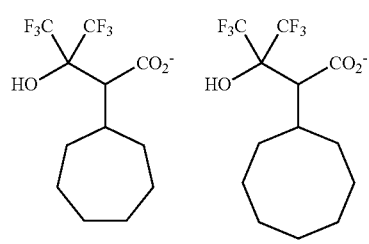

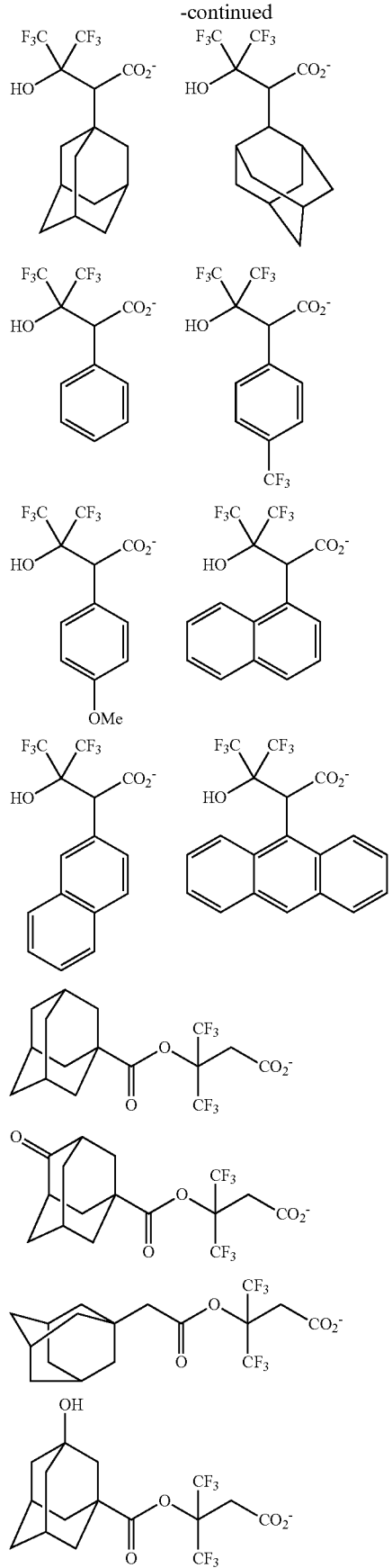
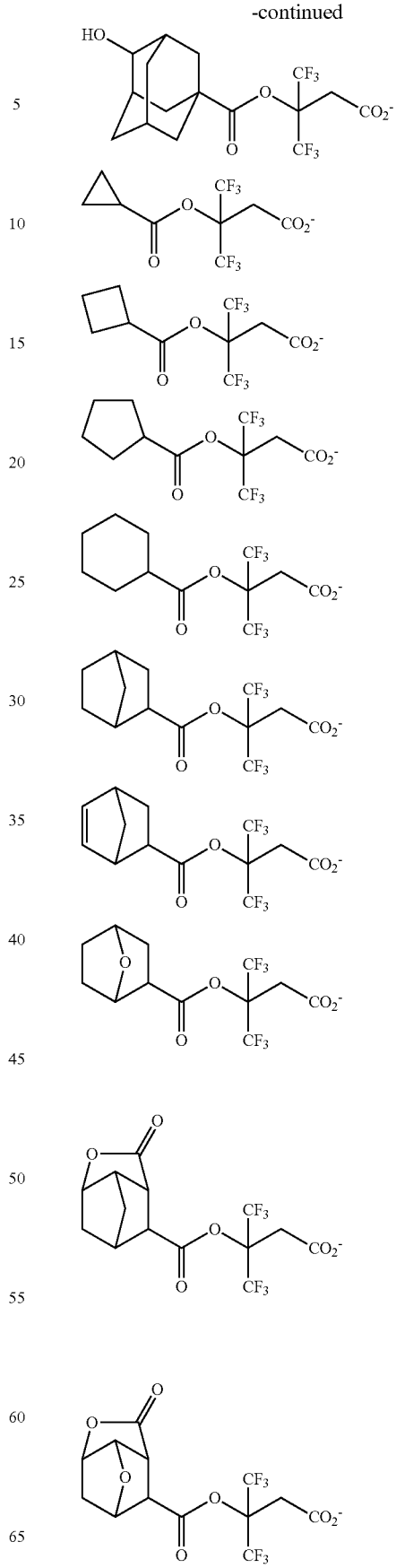

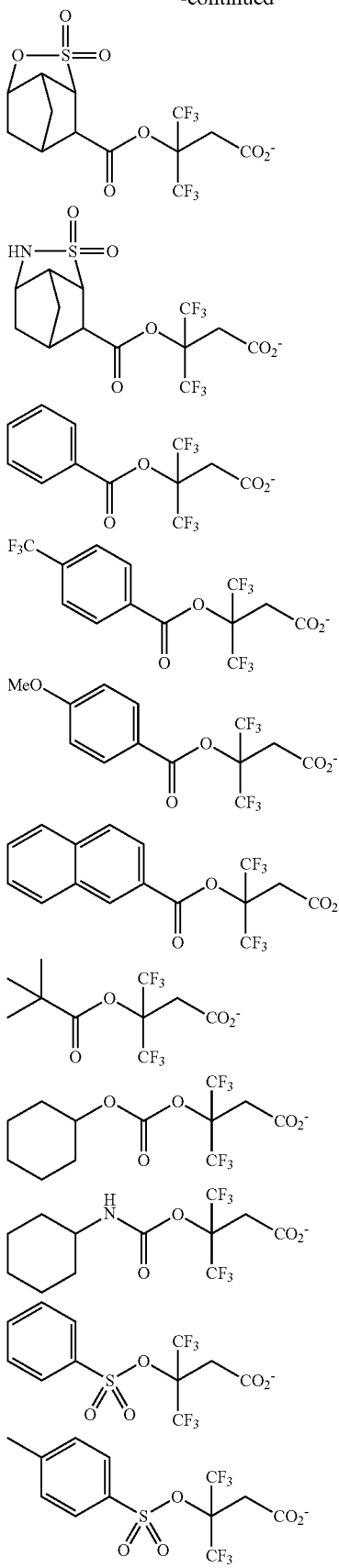

An onium salt having such a structure as the anion has very high lipophilicity due to the solvent solubility of fluorine atoms despite carboxylic acid salt and is least leachable in water during immersion lithography due to water repellency. The onium salt has a fully low acidity since they have fluorine or perfluoroalkyl group on the carbon atom at β-position relative to the carboxylate anion moiety. Therefore, the onium salt can effectively trap the strong acid generated by the acid generator without cleavage of acid labile groups on the base resin.

In formula (1), $Z^+$ is a sulfonium cation having the formula (2) or an iodonium cation having the formula (3).

In formula (2), $R^{11}$, $R^{12}$ and $R^{13}$ are each independently a $C_1$-$C_{20}$ straight, branched or cyclic monovalent hydrocarbon group which may contain a heteroatom. Suitable monovalent hydrocarbon groups include alkyl groups such as methyl, ethyl, n-propyl, isopropyl, n-butyl, tert-butyl, cyclopropyl, cyclopentyl, cyclohexyl, cyclopropylmethyl, 4-methylcyclohexyl, cyclohexylmethyl, norbornyl, and adamantyl, alkenyl groups such as vinyl, allyl, propenyl, butenyl, hexenyl and cyclohexenyl, aryl groups such as phenyl, naphthyl, and thienyl, and aralkyl groups such as benzyl, 1-phenylethyl and 2-phenylethyl, with the aryl groups being preferred. In these groups, one or more hydrogen atom may be replaced by a substituent containing a heteroatom such as oxygen, sulfur, nitrogen or halogen, or a substituent containing a heteroatom such as oxygen, sulfur or nitrogen may intervene between carbon atoms, so that the group may contain a hydroxyl moiety, cyano moiety, carbonyl moiety, ether bond, ester bond, sulfonate (sulfonic acid ester) bond, carbonate bond, lactone ring, sultone ring, carboxylic anhydride or haloalkyl moiety.

Any two of $R^{11}$, $R^{12}$ and $R^{13}$ may bond together to form a ring with the sulfur atom in the formula. Examples of the sulfonium cation having formula (2) where two R's form a ring are shown below.

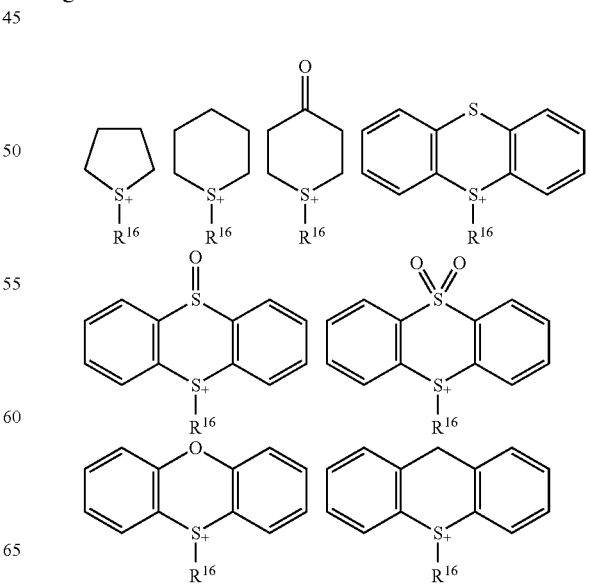

-continued
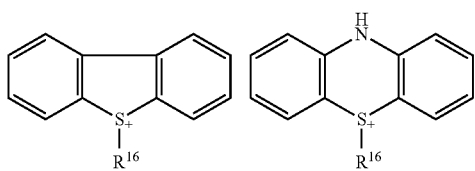
Herein $R^{16}$ is a $C_1$-$C_{20}$ straight, branched or cyclic monovalent hydrocarbon group which may contain a heteroatom.
Examples of the sulfonium cation having formula (2) are shown below, but not limited thereto.
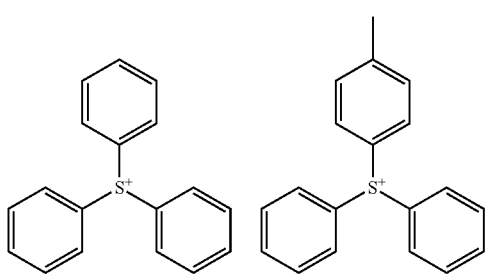
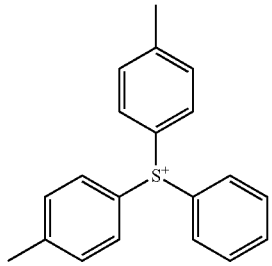
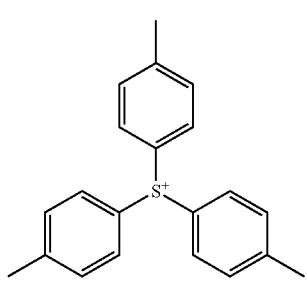
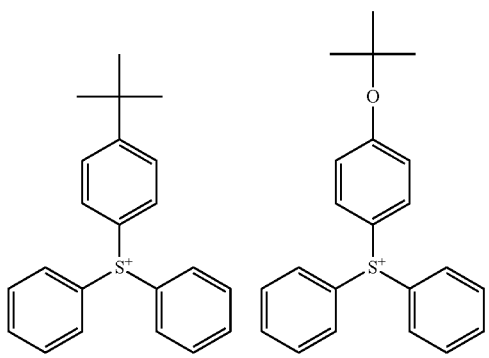
-continued
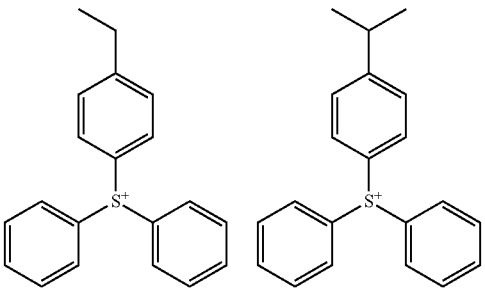
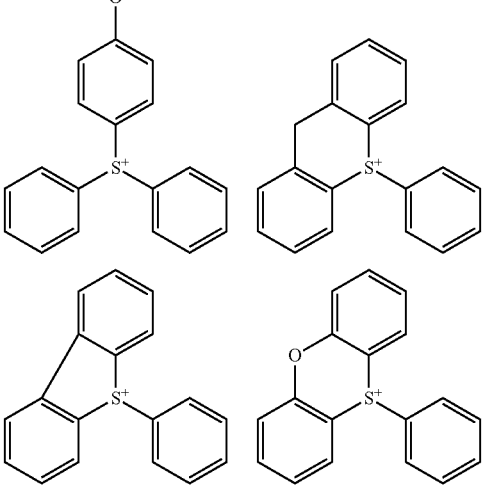
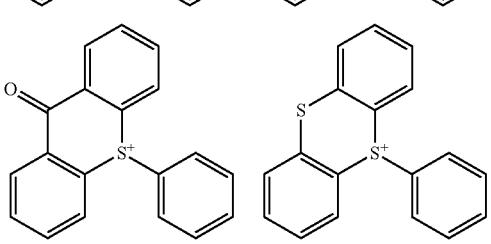
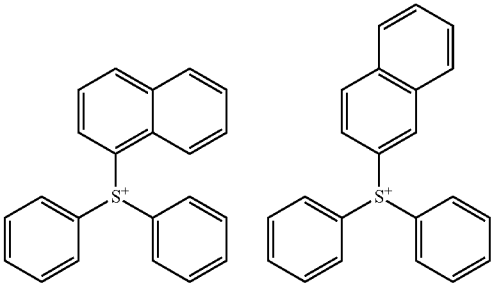
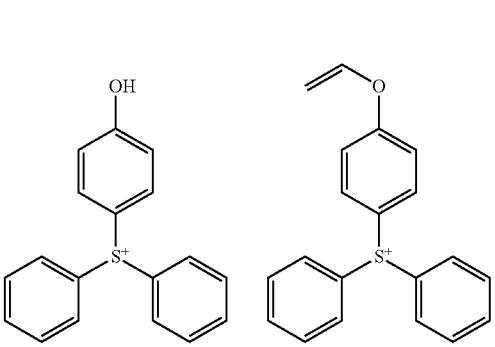

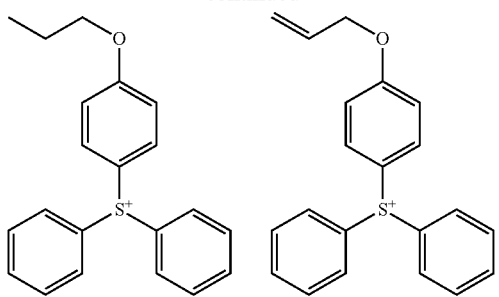
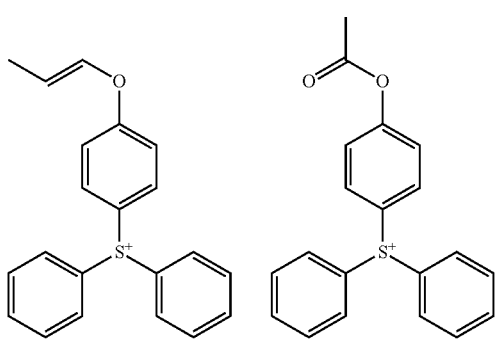
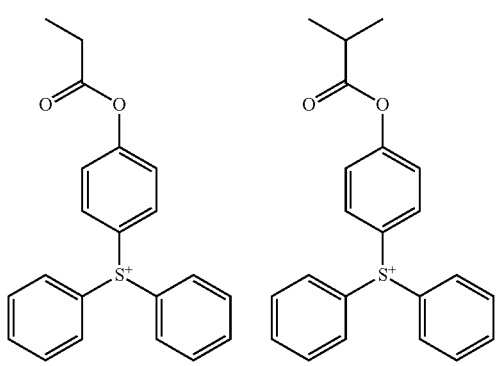
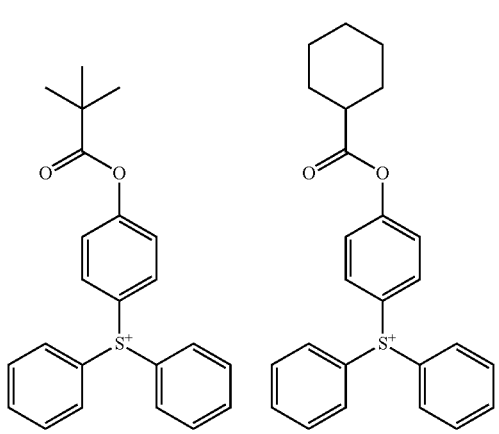
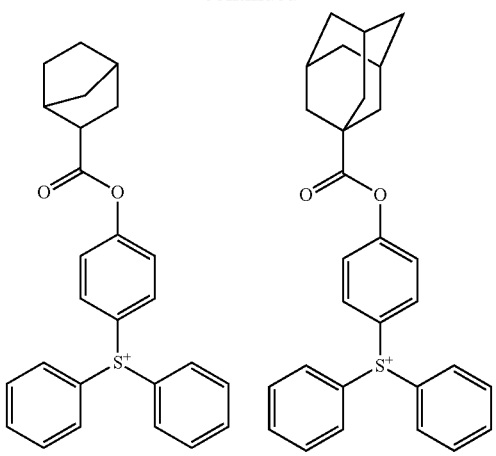
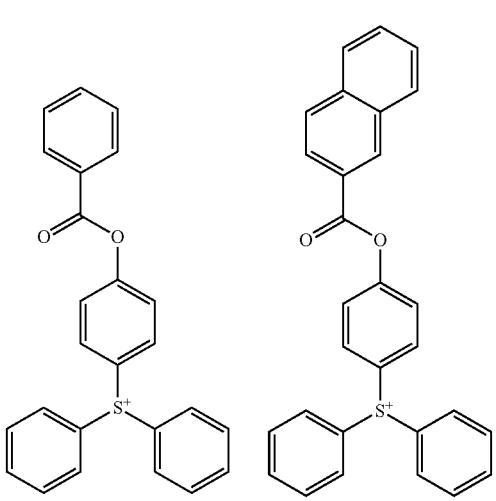
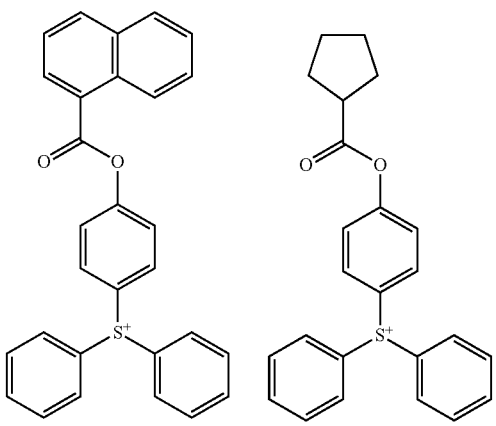

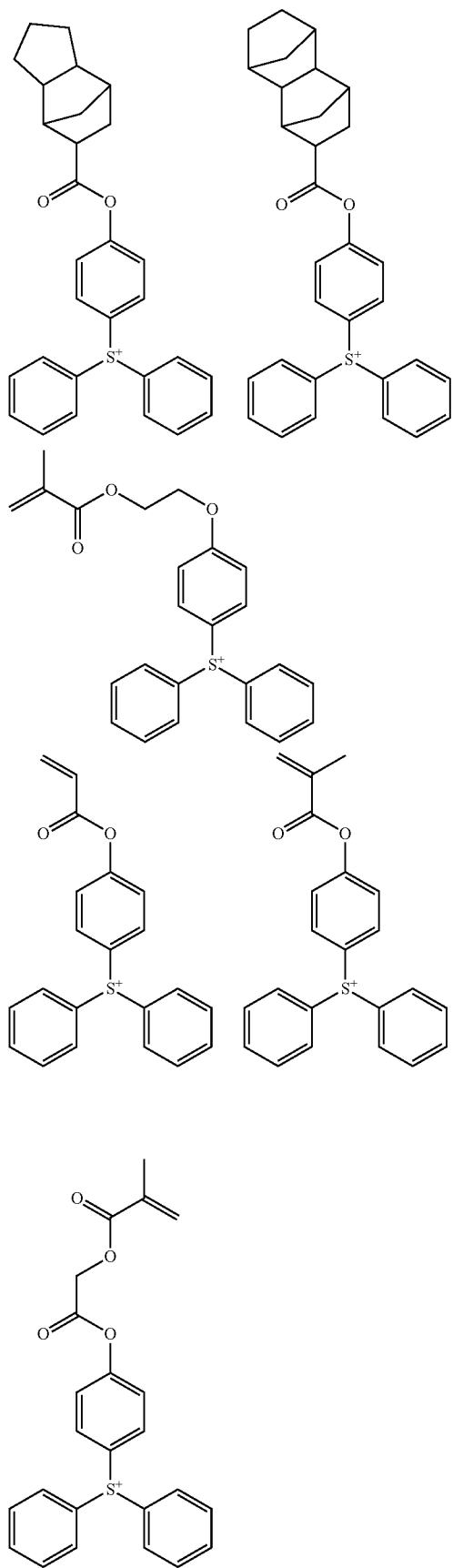
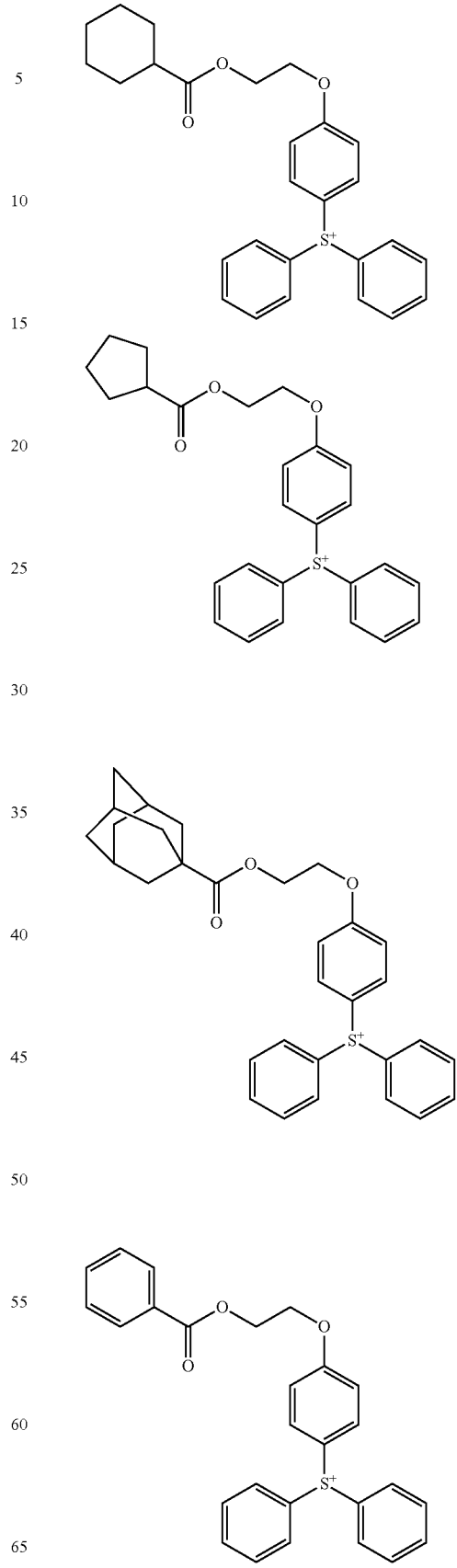

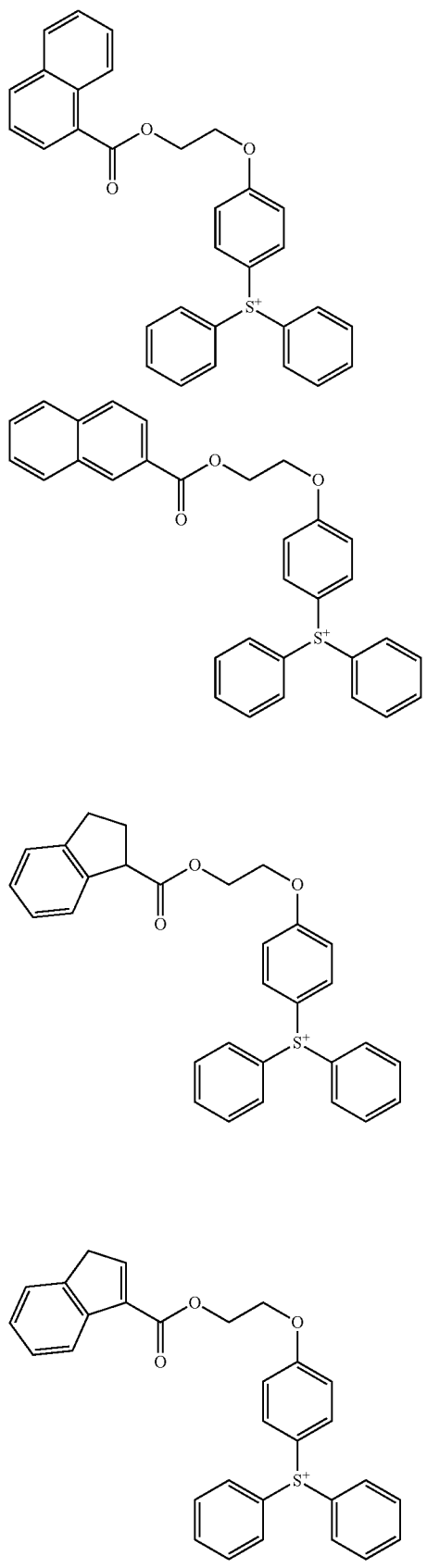
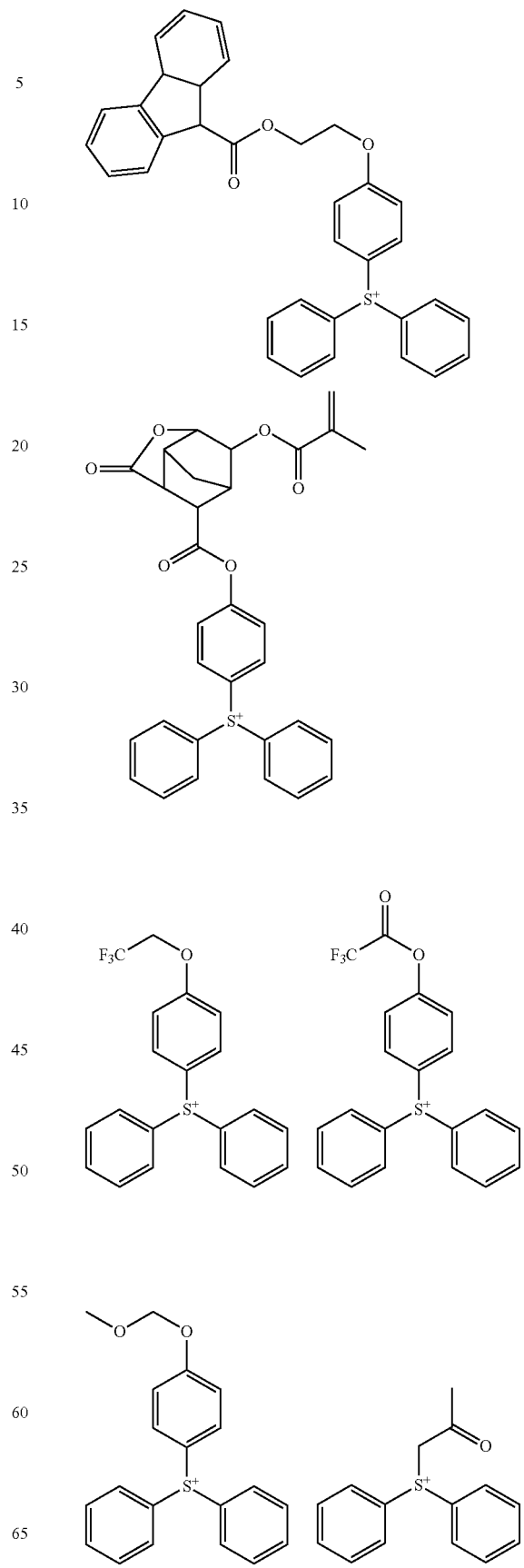

-continued
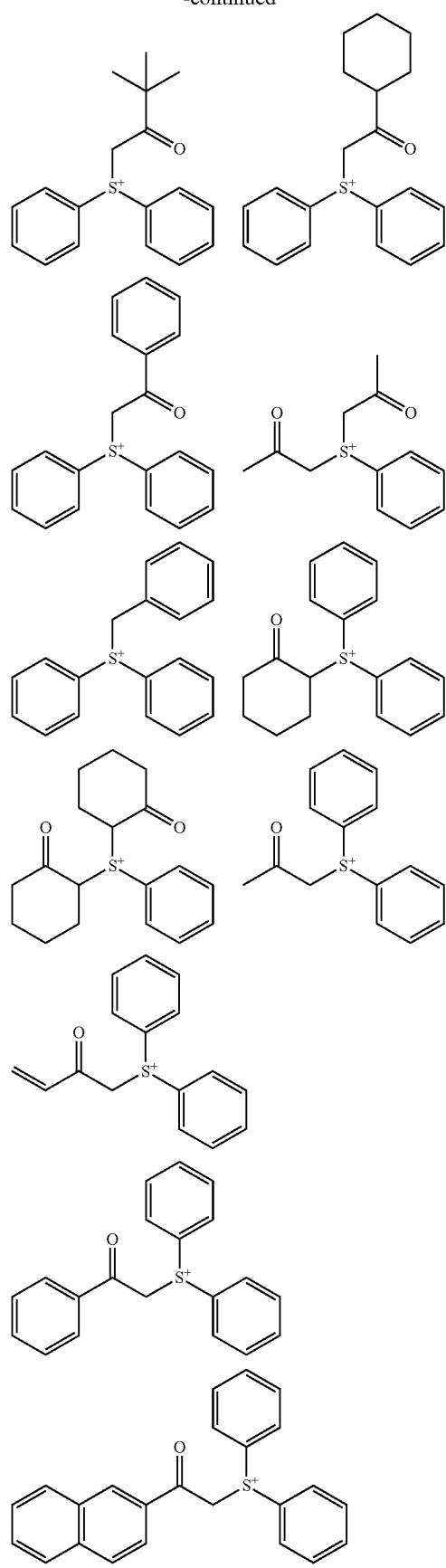
-continued
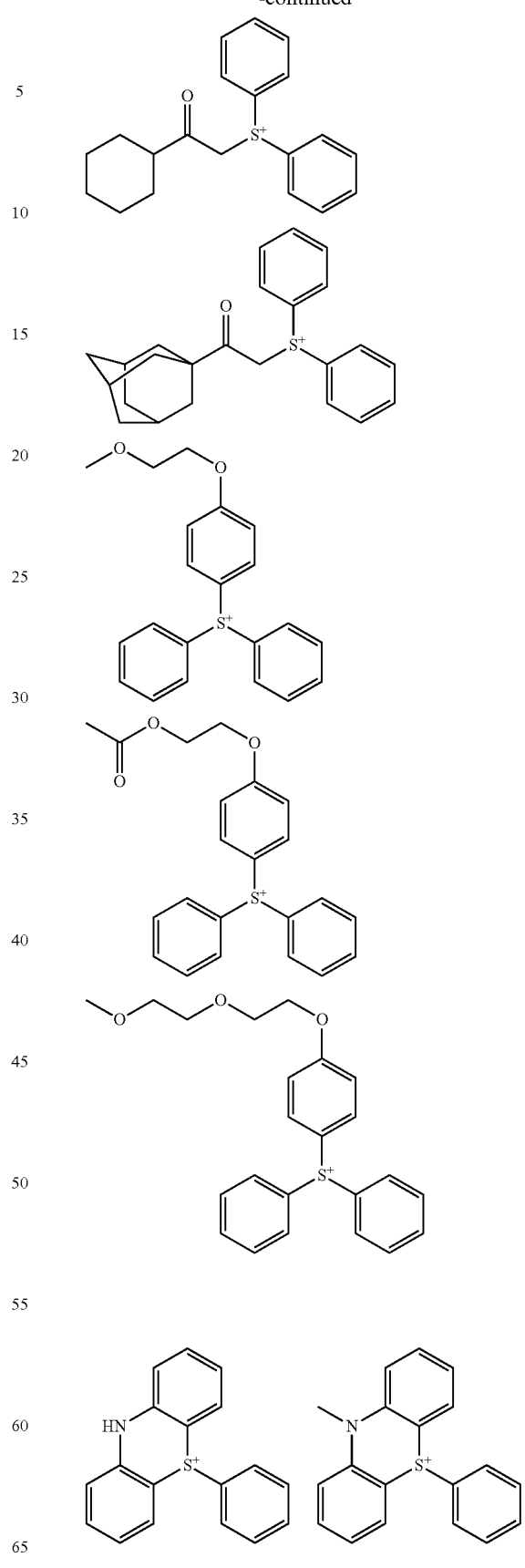

-continued
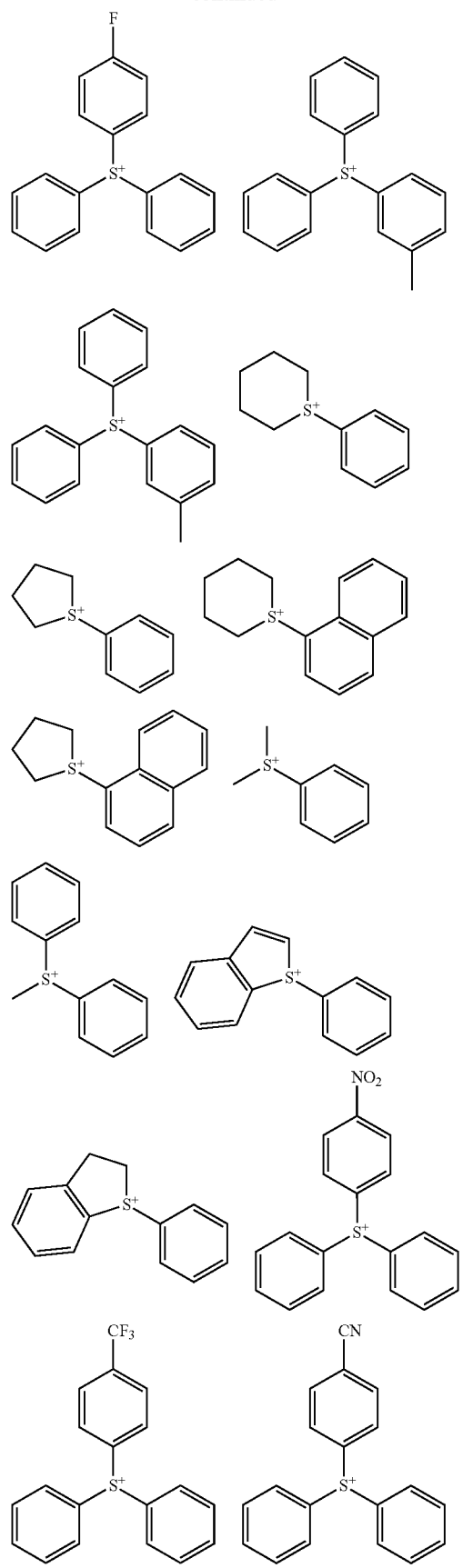
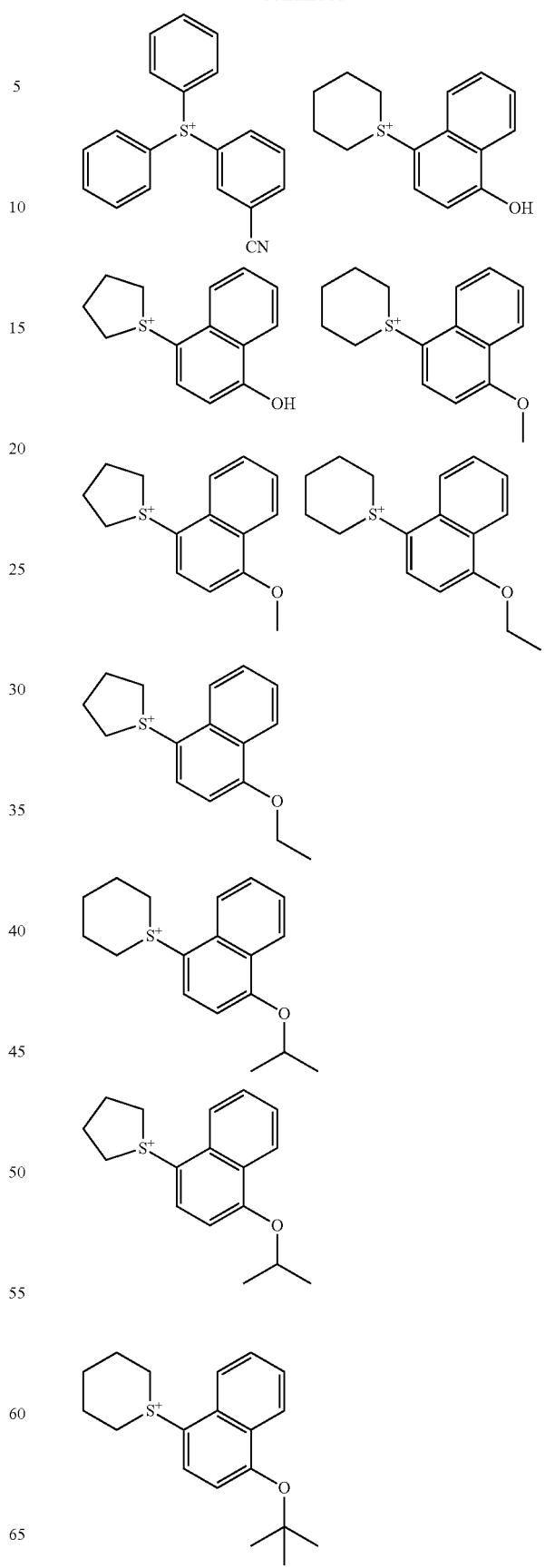

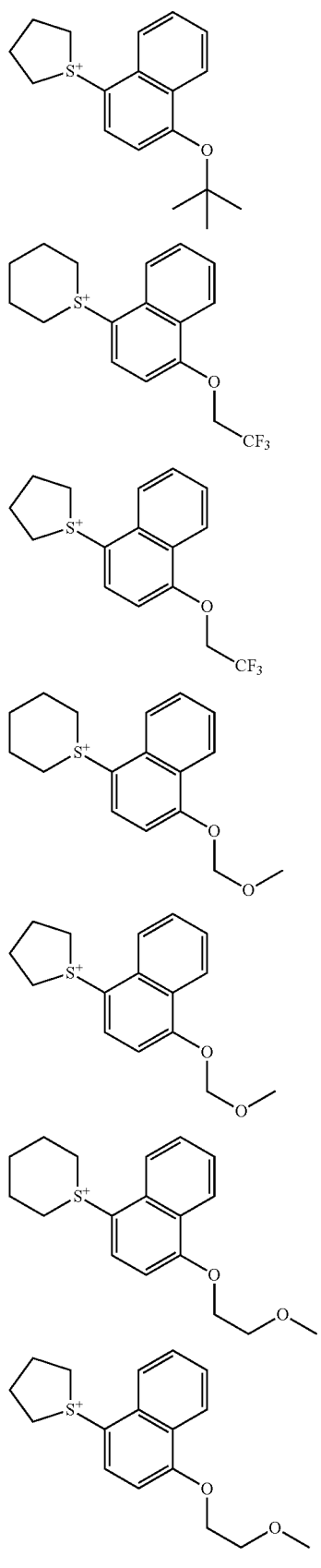
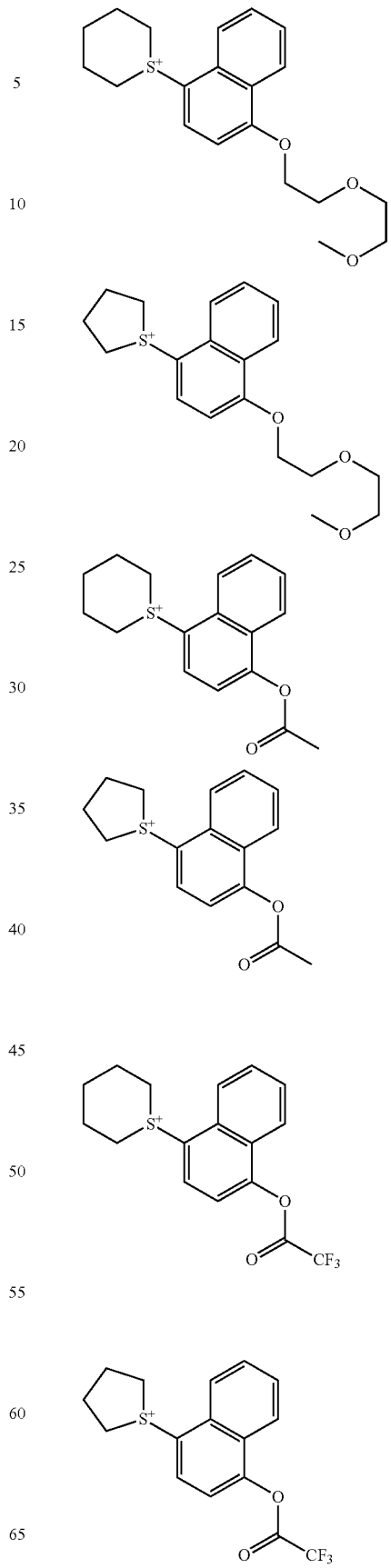

27
-continued
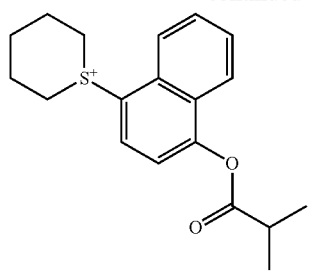
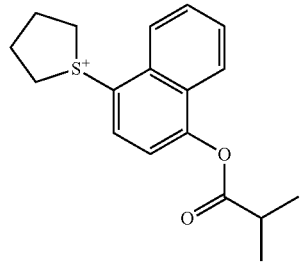
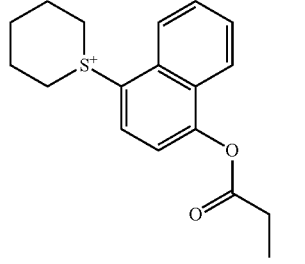
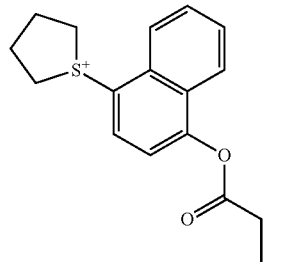
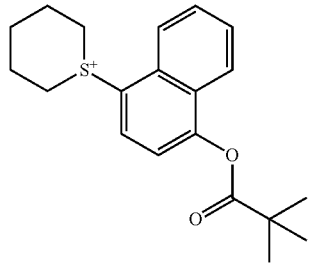
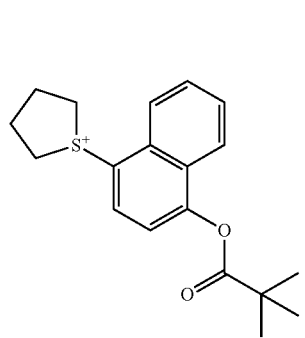
28
-continued
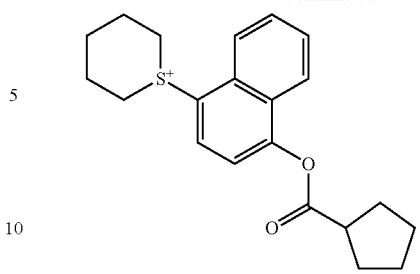
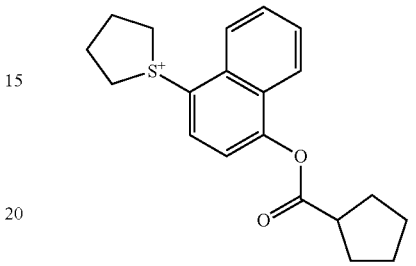
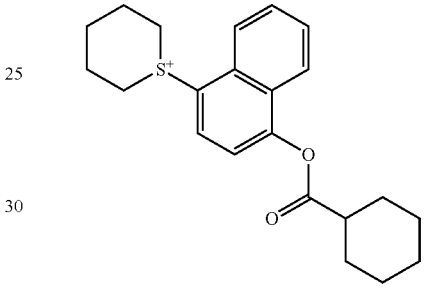
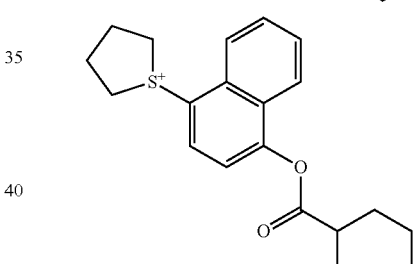
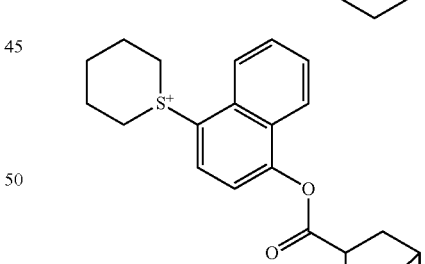
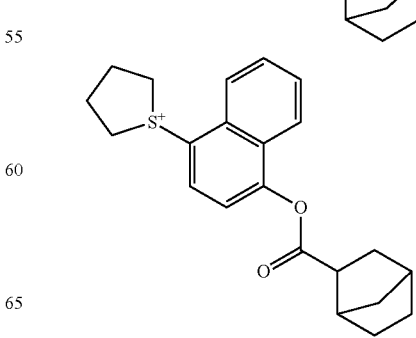

29
-continued

30
-continued

31
-continued
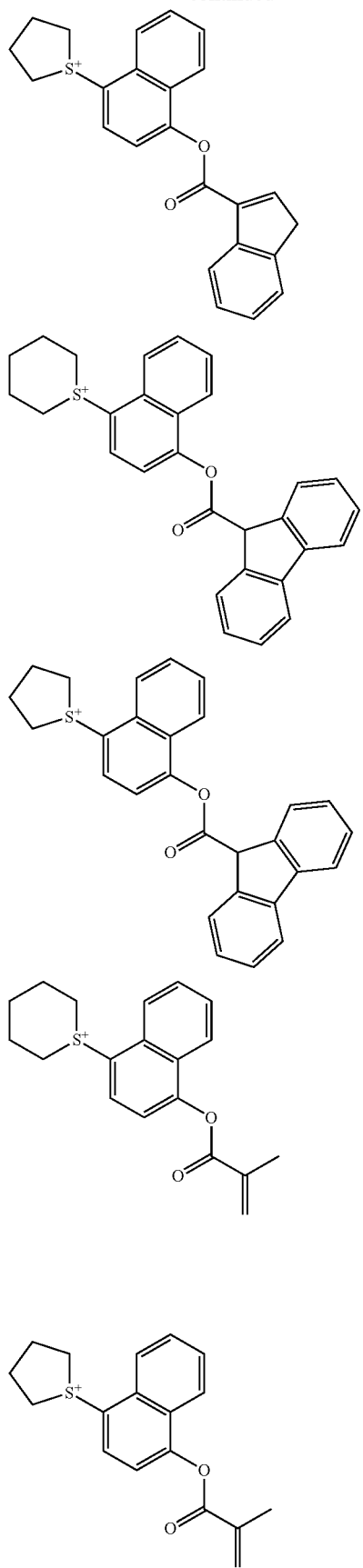
32
-continued
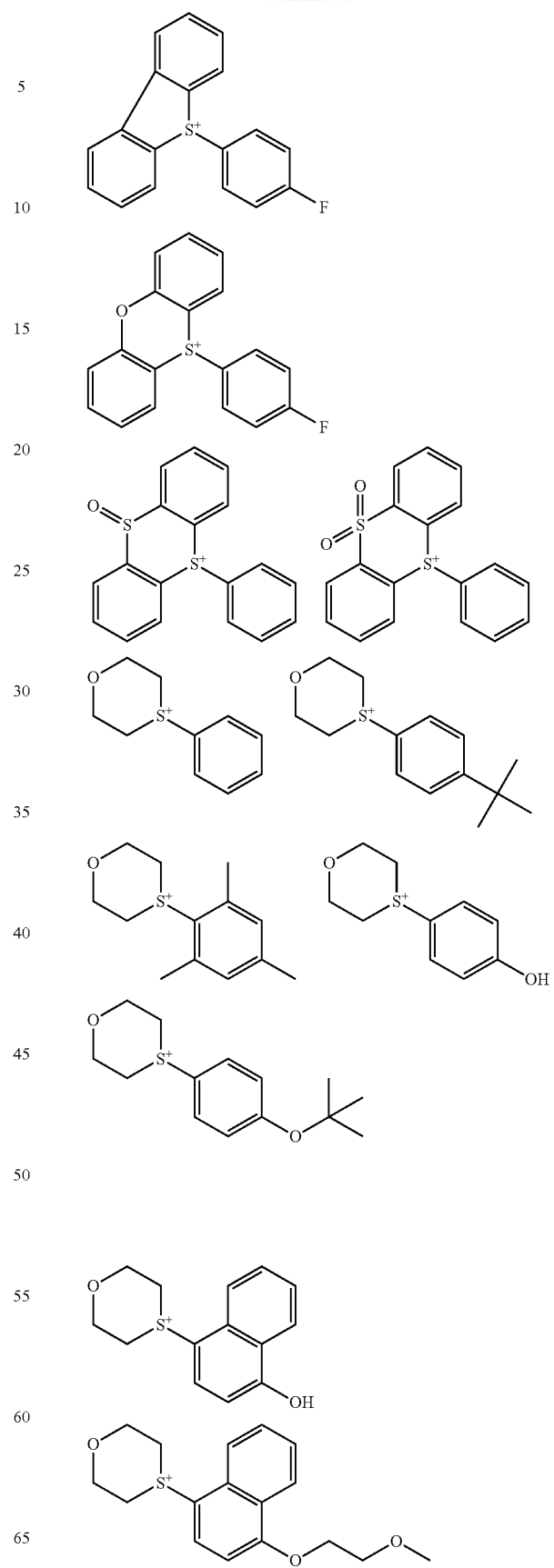

-continued
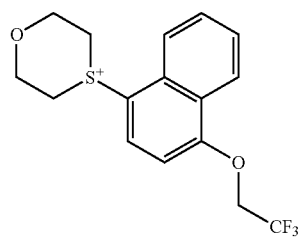
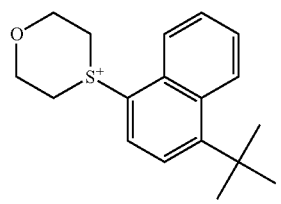
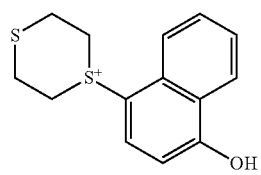
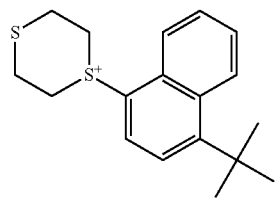
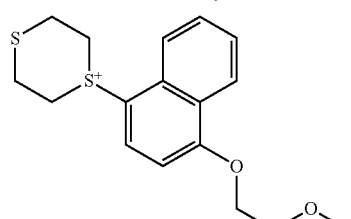
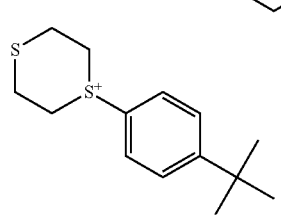
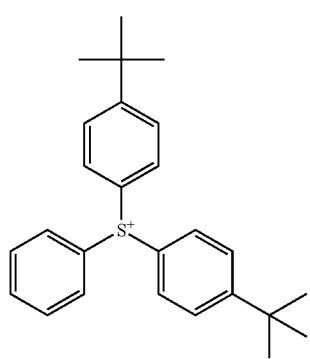
-continued
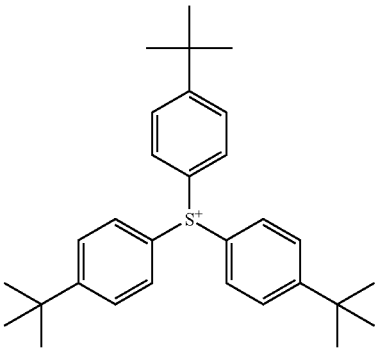
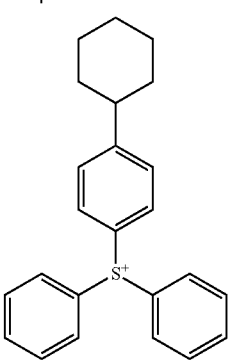
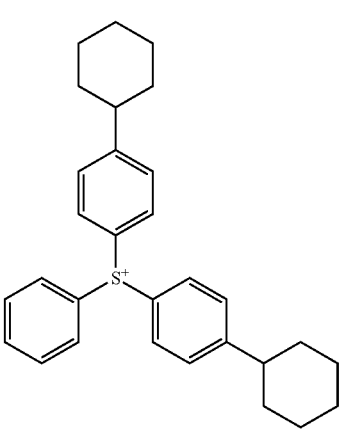
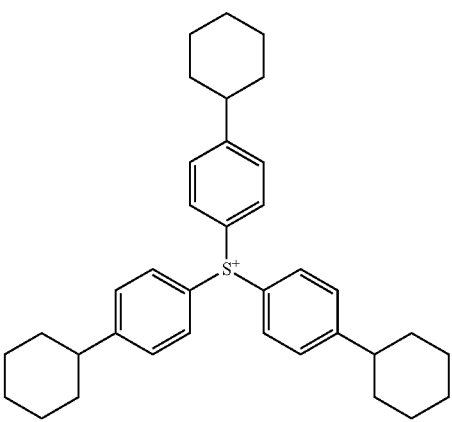

35
-continued
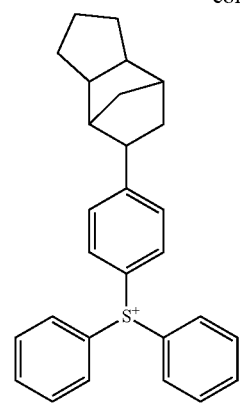
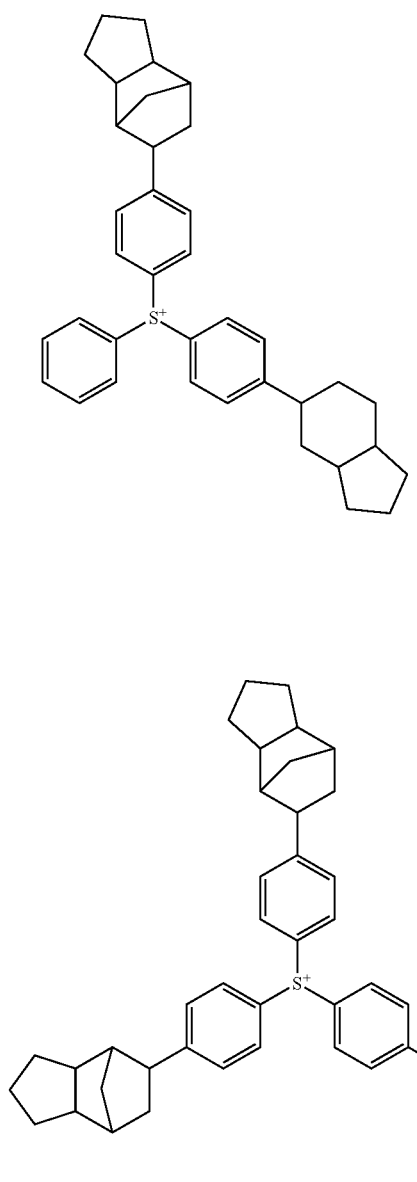
36
-continued
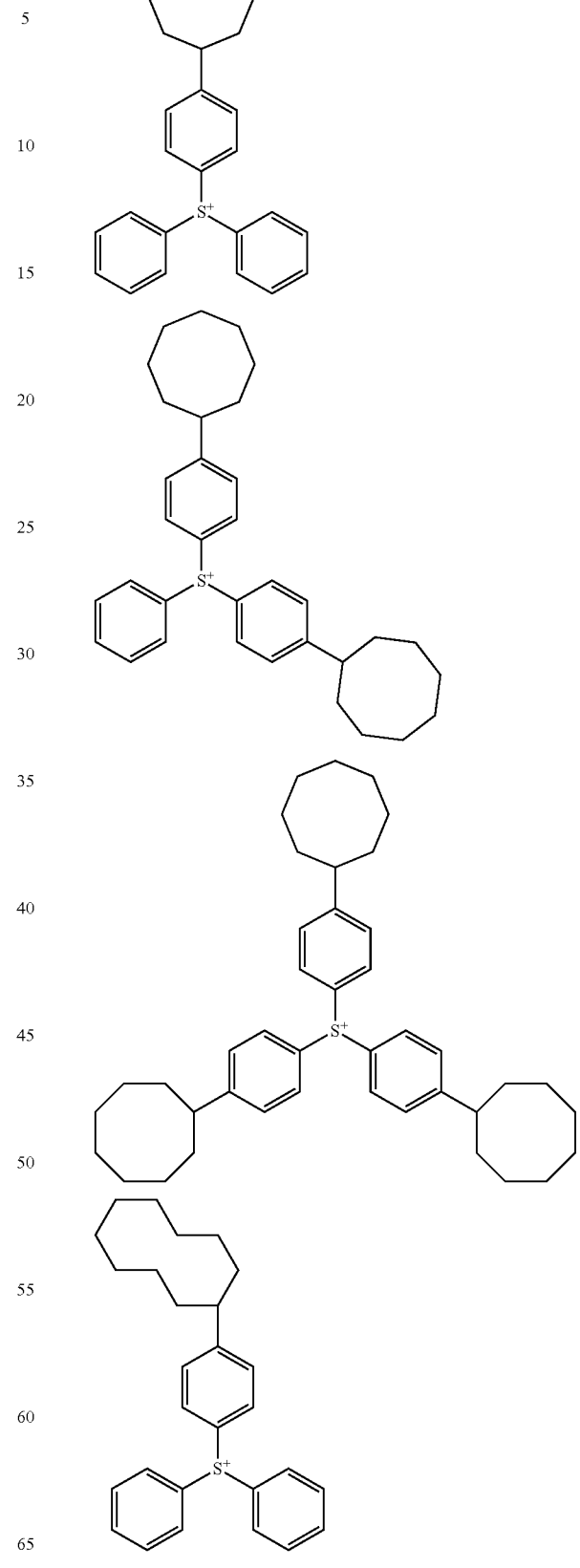

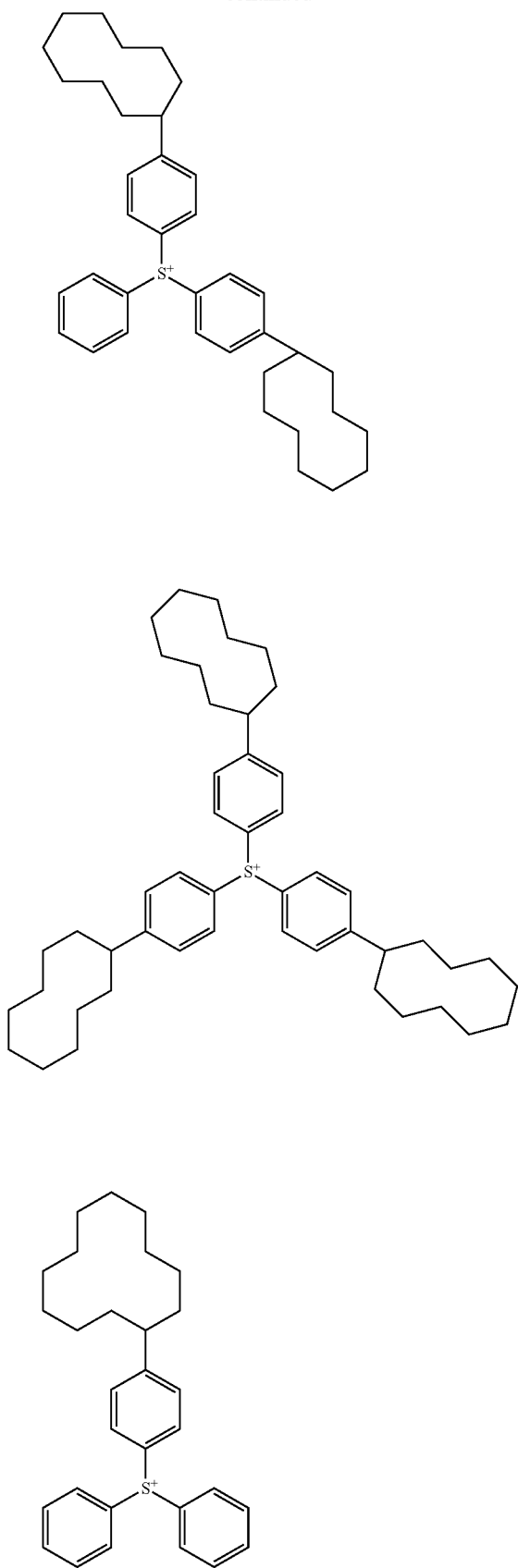

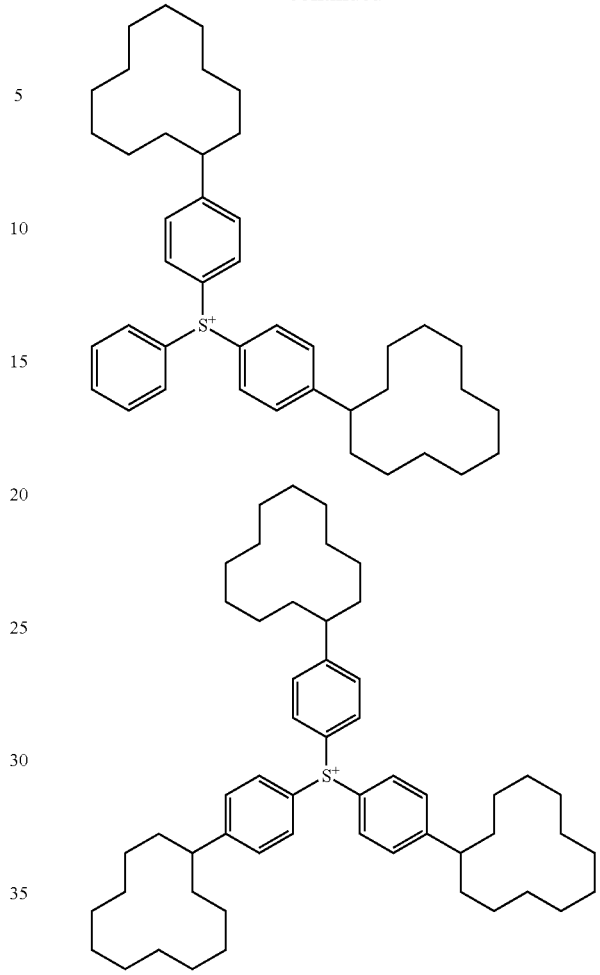

In formula (3), $R^{14}$ and $R^{15}$ are each independently a $C_1$-$C_{20}$ straight, branched or cyclic monovalent hydrocarbon group which may contain a heteroatom. Suitable monovalent hydrocarbon groups include alkyl groups such as methyl, ethyl, n-propyl, isopropyl, n-butyl, tert-butyl, cyclopropyl, cyclopentyl, cyclohexyl, cyclopropylmethyl, 4-methylcyclohexyl, cyclohexylmethyl, norbornyl, and adamantyl, alkenyl groups such as vinyl, allyl, propenyl, butenyl, hexenyl and cyclohexenyl, aryl groups such as phenyl, naphthyl, and thienyl, and aralkyl groups such as benzyl, 1-phenylethyl and 2-phenylethyl, with the aryl groups being preferred. In these groups, one or more hydrogen atom may be replaced by a substituent containing a heteroatom such as oxygen, sulfur, nitrogen or halogen, or a substituent containing a heteroatom such as oxygen, sulfur or nitrogen may intervene between carbon atoms, so that the group may contain a hydroxyl moiety, cyano moiety, carbonyl moiety, ether bond, ester bond, sulfonate bond, carbonate bond, lactone ring, sultone ring, carboxylic anhydride or haloalkyl moiety.

Examples of the iodonium cation having formula (3) are shown below, but not limited thereto.

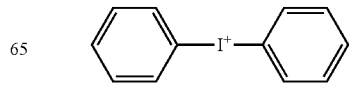

-continued

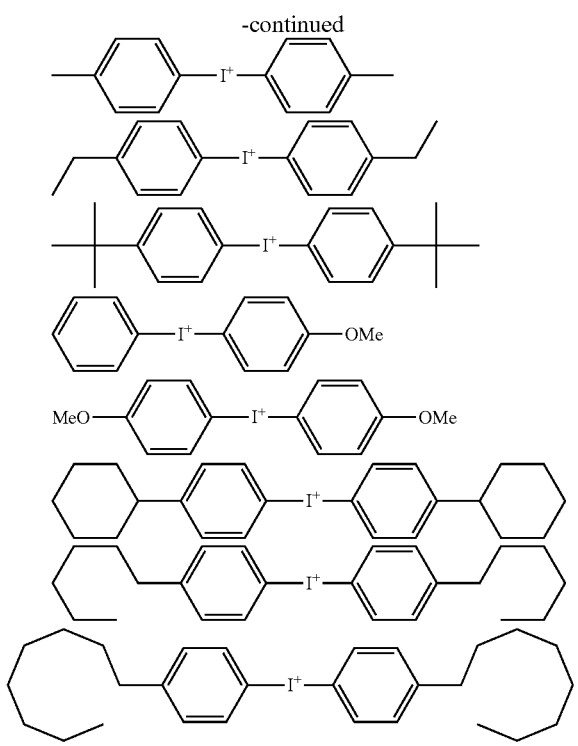

Illustrative structures of the carboxylic acid onium salt include arbitrary combinations of the above-exemplified anion moieties with the above-exemplified cation moieties.

In a system where a carboxylic acid onium salt of the invention and an onium salt capable of generating strong acid such as α-fluorinated sulfonic acid, imidic acid or methidic acid (which are collectively referred to as "strong acid" in this context) are co-present, a corresponding carboxylic acid and strong acid generate upon light exposure. On the other hand, in the region receiving a reduced dose of exposure, much (undecomposed) onium salt is present. The strong acid functions as a catalyst for inducing deprotection reaction to the base resin whereas the carboxylic acid onium salt of the invention induces little deprotection reaction. The strong acid undergoes ion exchange with the residual carboxylic acid sulfonium salt. It is converted to a strong acid onium salt and instead, carboxylic acid is released. Differently stated, through ion exchange, the strong acid is neutralized with the carboxylic acid onium salt. That is, the carboxylic acid onium salt of the invention functions as a quencher. This onium salt type quencher tends to form a resist pattern with a reduced LWR as compared with the conventional quenchers in the form of amine compounds.

Salt exchange between strong acid and carboxylic acid onium salt is infinitely repeated. The site where strong acid is generated at the end of exposure shifts from the site where the onium salt of strong acid generation type is initially present. It is believed that since the cycle of photo-acid generation and salt exchange is repeated many times, the acid generation point is averaged, which leads to a resist pattern with reduced LWR after development.

As the compound that exerts a quencher effect by a similar mechanism, Patent Documents 1 to 6 report carboxylic acid onium salts, alkanesulfonic acid onium salts, arenesulfonic acid onium salts, and α,α-difluorocarboxylic acid onium salts. With respect to the type of onium salt, sulfonium, iodonium and ammonium salts are included. However, on use of an alkanesulfonic acid onium salt or arenesulfonic acid onium salt, the generated acid has such an acid strength that part thereof may function as the acid generator to induce deprotection reaction rather than functioning as the quencher, leading to a lowering of resolution and an increase of acid diffusion, which invite degradation of resist performance factors like exposure latitude (EL) and mask error factor (MEF). Also, the α,α-difluorocarboxylic acid onium salt described in Patent Document 6 is a carboxylic acid onium salt, but has fluorine atom at α-position relative to the carboxylate anion. Thus, like the aforementioned sulfonic acid onium salts, the generated acid has a certain level of acidity, which can induce deprotection reaction depending on a choice of acid labile groups on the base resin. Likewise, fluorocarboxylic acid onium salts obtained by simply extending the straight chain allow for acid diffusion and undergo salt exchange with strong acid in the unexposed region, probably leading to reductions of resolution, EL and MEF. Further, the alkanecarboxylic acid onium salt can function as the quencher. However, due to its very high hydrophilicity, possible leaching of carboxylic acid onium salt in water becomes a concern, particularly in the ArF immersion lithography. The leaching in water is undesired because it causes contamination to the exposure tool and defect formation after development. As discussed in Patent Document 3, the fluoroalkanecarboxylic acid onium salts offer a certain degree of hydrophilicity control as compared with non-fluorinated acid onium salts, but the control of hydrophilicity is insufficient when the carbon count is low. Although perfluoroalkanecarboxylic acid onium salts having a high carbon count are exemplified, these carboxylic acids have surfactant-like physical properties and are deemed incompatible with resist compositions. Incompatibility with resist composition can cause defect formation. In addition, perfluoroalkanecarboxylic acids are unfavorable from the biotic and environmental aspects.

The above-discussed problems are solved by the carboxylic acid onium salt of the invention. The carboxylic acid onium salt is structurally characterized in that it is a β,β-difluoro (or bisperfluoroalkyl) carboxylic acid salt. This structure, due to the water repellency of fluorine atoms, enables to control the hydrophilicity of onium salt to a substantial extent, minimizes leaching in water particularly in the ArF immersion lithography, and is effective for reducing defects after development. Also, since β,β-difluoro (or bisperfluoroalkyl) carboxylic acid available after proton exchange with strong acid has an insufficient acidity to induce deprotection reaction of acid labile groups on the base resin, the contrast between exposed and unexposed regions is improved, so that a resist composition which is improved not only in LWR, but also in resolution, EL and MEF is available. Furthermore, since the carboxylic acid onium salt of the invention is fully compatible with resist components by virtue of its structure, defects resulting from less-dissolvable onium salts are eliminated or reduced.

The carboxylic acid onium salt of the invention may be synthesized, for example, according to the following scheme. Although reference is made to the synthesis of a carboxylic acid onium salt wherein $R^{f1}$ and $R^{f2}$ are trifluoromethyl as a typical example, the synthesis route is not limited thereto.

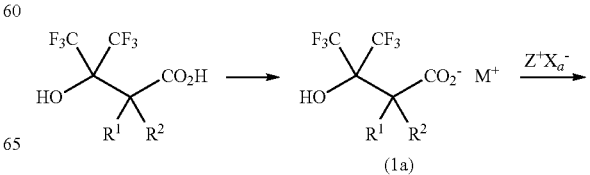

(1a)

-continued

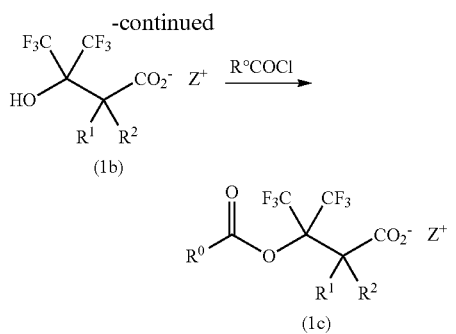

Herein $R^0$, $R^1$, $R^2$, and $Z^+$ are as defined above, $M^+$ is a cation, and $X_a^-$ is an anion.

First, an intermediate compound (1a) is synthesized by alkaline hydrolysis of β,β-bistrifluoromethylhydroxycarboxylic acid. The reaction may be performed using water as solvent. The base for hydrolysis may be selected from hydroxides of alkali metals and alkaline earth metals. Inter alia, sodium hydroxide or potassium hydroxide is preferably used for commercial availability.

Next, intermediate compound (1a) is subjected to a salt exchange with an onium salt of the formula; $Z^+X_a^-$, to synthesize carboxylic acid onium salt (1b). Of the anions $X_a^-$, chloride, bromide, iodide, and methylsulfate anions are preferred because they allow for quantitative progress of exchange reaction. The carboxylic acid onium salt (1b) may be directly used as acid diffusion inhibitor.

Further, the hydroxyl group in the anion of carboxylic acid onium salt (1b) is modified, for example, acylated to synthesize carboxylic acid onium salt (1c). For the acylation reaction, not only the reaction with acid chlorides, but also any well-known organic chemistry reactions such as reaction with acid anhydrides are applicable.

The second step of ion exchange in the above scheme may be readily carried out by well-known methods, for example, with reference to JP-A 2007-145797 (U.S. Pat. No. 7,511,169).

Understandably, the synthesis method according to the above scheme is merely exemplary and the invention is not limited thereto. While the scheme refers to the synthesis of an ester compound, those skilled artisans can synthesize onium salts having an ether, sulfonate, carbonate or carbamate bond by using the chemical techniques within the common knowledge of organic chemistry.

Acid Diffusion Inhibitor

The carboxylic acid onium salt defined herein is useful as an acid diffusion inhibitor or quencher.

Resist Composition

Another embodiment of the invention is directed to a resist composition comprising (A) an acid diffusion inhibitor in the form of a carboxylic acid onium salt having formula (1) as an essential component, (B) a base resin, (C) a photoacid generator, and (D) an organic solvent. If necessary, the resist composition may further comprise (E) a nitrogen-containing compound, (F) a surfactant which is insoluble or substantially insoluble in water and soluble in alkaline developer and/or a surfactant which is insoluble or substantially insoluble in water and alkaline developer, and (G) another component.

The carboxylic acid onium salt functions as an acid diffusion inhibitor (or controlling agent). An appropriate amount of the onium salt is 0.1 to 40 parts, more preferably 1 to 20 parts by weight per 100 parts by weight of the base resin (B), As long as its amount is in the range, the carboxylic acid onium salt fully functions as an acid diffusion inhibitor, eliminating any performance problems such as sensitivity drop, solubility shortage, and foreign particles.

(B) Base Resin

The base resin used in the resist composition preferably contains a polymer comprising recurring units having the formula (a) and recurring units having the formula

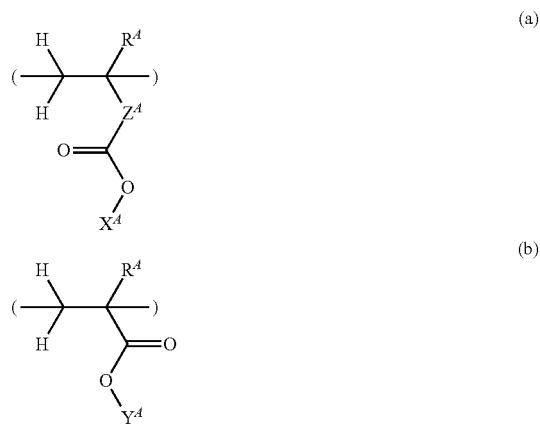

Herein $R^A$ is hydrogen, methyl or trifluoromethyl. $Z^A$ is a single bond, phenylene, naphthylene or (backbone)-C(=O)—O—Z'—, wherein Z' is a $C_1$-$C_{10}$ straight, branched or cyclic alkylene group which may contain a hydroxyl moiety, ether bond, ester bond, or lactone ring, or a phenylene or naphthylene group. $X^A$ is an acid labile group. $Y^A$ is hydrogen or a polar group having at least one structure selected from the group consisting of hydroxyl, cyano, carbonyl, carboxyl, ether bond, ester bond, sulfonate bond, carbonate bond, lactone ring, sultone ring, and carboxylic anhydride.

Examples of the structure of formula (a) wherein $Z^A$ is a variant are illustrated below, but not limited thereto. $R^A$ and $X^A$ are as defined above.

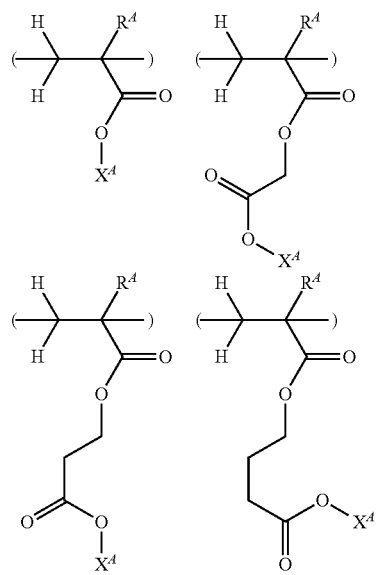

-continued
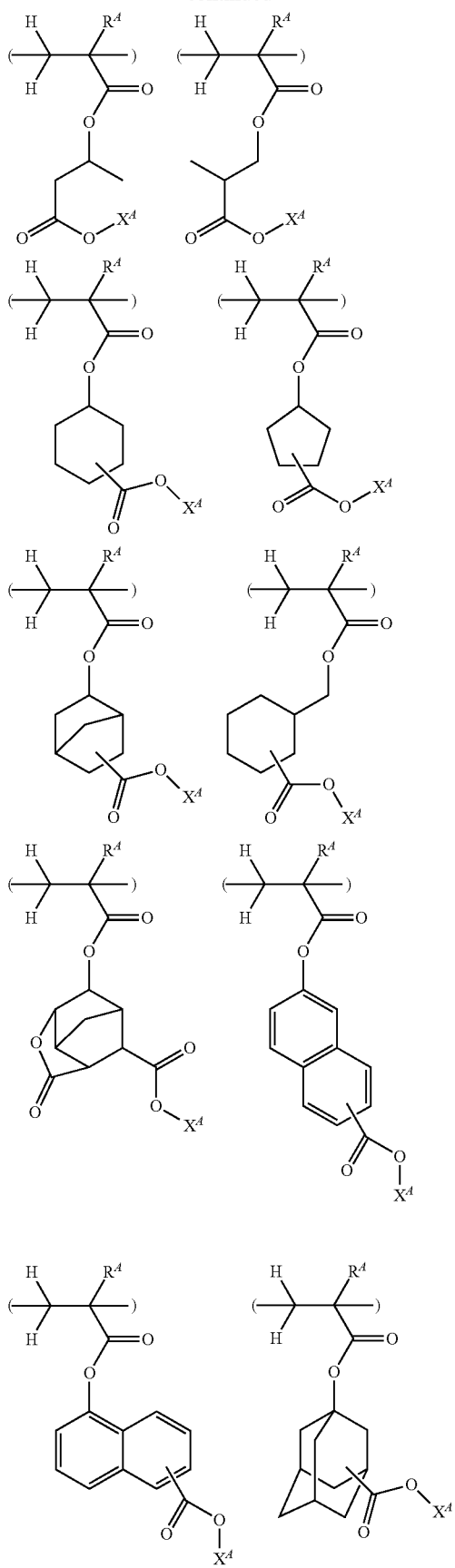
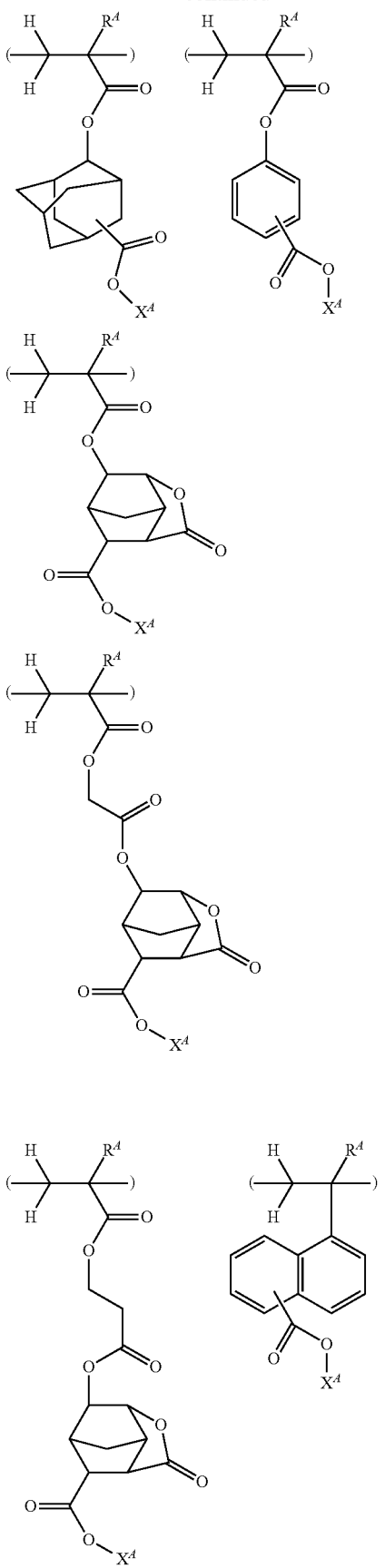

-continued

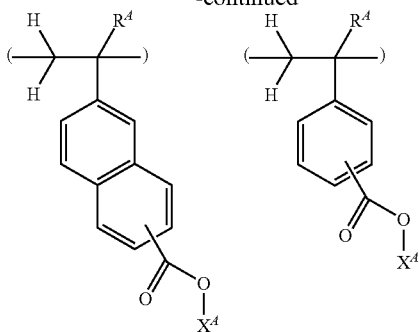

The polymer comprising recurring units having formula (a) functions such that it may be decomposed to generate carboxylic acid under the action of an acid and turn alkali soluble.

The acid labile group represented by $X^A$ may be selected from a variety of such groups. Examples of the acid labile group include groups of the following general formulae (L1) to (L4), tertiary alkyl groups of 4 to 20 carbon atoms, preferably 4 to 15 carbon atoms, trialkylsilyl groups in which each alkyl moiety has 1 to 6 carbon atoms, and oxoalkyl groups of 4 to 20 carbon atoms.

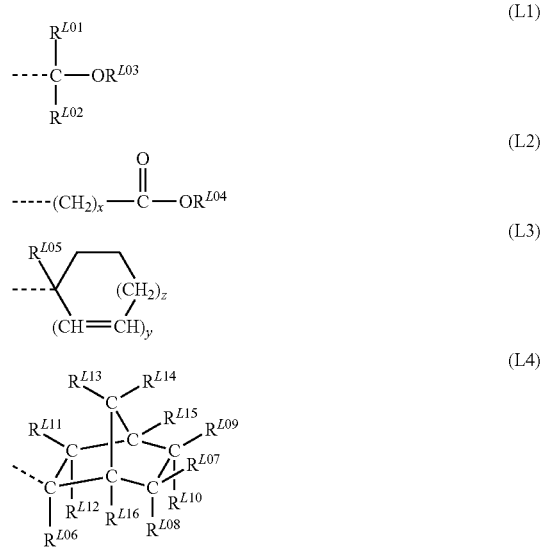

In formula (L1), $R^{L01}$ and $R^{L02}$ are hydrogen or straight, branched or cyclic alkyl groups of 1 to 18 carbon atoms, preferably 1 to 10 carbon atoms. Exemplary alkyl groups include methyl, ethyl, propyl, isopropyl, n-butyl, sec-butyl, tert-butyl, cyclopentyl, cyclohexyl, 2-ethylhexyl, n-octyl, norbornyl, tricyclodecanyl, tetracyclododecanyl, and adamantyl. $R^{L03}$ is a monovalent hydrocarbon group of 1 to 18 carbon atoms, preferably 1 to 10 carbon atoms, which may contain a heteroatom such as oxygen, examples of which include unsubstituted straight, branched or cyclic alkyl groups and straight, branched or cyclic alkyl groups in which some hydrogen atoms are replaced by hydroxyl, alkoxy, oxo, amino, alkylamino or the like, or in which a heteroatom such as oxygen intervenes between carbon atoms. Exemplary alkyl groups are as exemplified above for $R^{L01}$ and $R^{L02}$.

Illustrative examples of the substituted alkyl groups are shown below.

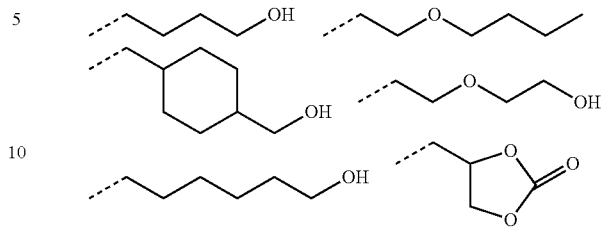

A pair of $R^{L01}$ and $R^{L02}$, $R^{L01}$ and $R^{L03}$, or $R^{L02}$ and $R^{L03}$ may bond together to form a ring with the carbon and oxygen atom to which they are attached. A ring-forming pair of $R^{L01}$, $R^{L02}$ and $R^{L03}$ is a straight or branched alkylene group of 1 to 18 carbon atoms, preferably 1 to 10 carbon atoms.

In formula (L2), $R^{L04}$ is a tertiary alkyl group of 4 to 20 carbon atoms, preferably 4 to 15 carbon atoms, a trialkylsilyl group in which each alkyl moiety has 1 to 6 carbon atoms, an oxoalkyl group of 4 to 20 carbon atoms, or a group of formula (L1). Exemplary tertiary alkyl groups are tert-butyl, tert-pentyl, 1,1-diethylpropyl, 2-cyclopentylpropan-2-yl, 2-cyclohexylpropan-2-yl, 2-(bicyclo[2.2.1]heptan-2-yl)propan-2-yl, 2-(adamantan-1-yl)propan-2-yl, 1-ethylcyclopentyl, 1-butylcyclopentyl, 1-ethylcyclohexyl, 1-butylcyclohexyl, 1-ethyl-2-cyclopentenyl, 1-ethyl-2-cyclohexenyl, 2-methyl-2-adamantyl, and 2-ethyl-2-adamantyl. Exemplary trialkylsilyl groups are trimethylsilyl, triethylsilyl, and dimethyl-tert-butylsilyl. Exemplary oxoalkyl groups are 3-oxocyclohexyl, 4-methyl-2-oxooxan-4-yl, and 5-methyl-2-oxooxolan-5-yl. Letter x is an integer of 0 to 6.

In formula (L3), $R^{L05}$ is an optionally substituted, straight, branched or cyclic $C_1$-$C_8$ alkyl group or an optionally substituted $C_6$-$C_{20}$ aryl group. Examples of the optionally substituted alkyl group include straight, branched or cyclic alkyl groups such as methyl, ethyl, propyl, isopropyl, n-butyl, sec-butyl, tert-butyl, tert-pentyl, n-pentyl, n-hexyl, cyclopentyl and cyclohexyl, and substituted forms of the foregoing in which some hydrogen atoms are substituted by hydroxyl, alkoxy, carboxyl, alkoxycarbonyl, oxo, amino, alkylamino, cyano, mercapto, alkylthio, sulfo or the like. Examples of the optionally substituted aryl groups include phenyl, methylphenyl, naphthyl, anthryl, phenanthryl, and pyrenyl, and substituted forms of the foregoing in which some hydrogen atoms are substituted by hydroxyl, alkoxy, carboxyl, alkoxycarbonyl, oxo, amino, alkylamino, cyano, mercapto, alkylthio, sulfo or the like. Letter y is equal to 0 or 1, z is equal to 0, 1, 2 or 3, and 2y+z is equal to 2 or 3.

In formula (L4), $R^{L06}$ is an optionally substituted, straight, branched or cyclic $C_1$-$C_8$ alkyl group or an optionally substituted $C_6$-$C_{20}$ aryl group. Examples of these groups are the same as exemplified for $R^{L05}$. $R^{L07}$ to $R^{L16}$ independently represent hydrogen or $C_1$-$C_{15}$ monovalent hydrocarbon groups. Exemplary hydrocarbon groups are straight, branched or cyclic alkyl groups such as methyl, ethyl, propyl, isopropyl, n-butyl, sec-butyl, tert-butyl, tert-pentyl, n-pentyl, n-hexyl, n-octyl, n-nonyl, n-decyl, cyclopentyl, cyclohexyl, cyclopentylmethyl, cyclopentylethyl, cyclopentylbutyl, cyclohexylmethyl, cyclohexylethyl and cyclohexylbutyl, and substituted forms of the foregoing in which some hydrogen atoms are replaced by hydroxyl, alkoxy, carboxyl, alkoxycarbonyl, oxo, amino, alkylamino, cyano, mercapto, alkylthio, sulfo or other groups. Alternatively, two of $R^{L07}$ to $R^{L16}$ may bond together to form a ring with the carbon atom to which they are attached (for example, a pair of $R^{L07}$ and $R^{L08}$, $R^{L07}$ and $R^{L09}$, $R^{L07}$ and $R^{L10}$, $R^{L08}$ and $R^{L10}$, $R^{L09}$ and $R^{L10}$, $R^{L11}$ and $R^{L12}$, $R^{L13}$ and $R^{L14}$, or a similar pair form a ring). A ring-forming pair of $R^{L07}$ to $R^{L16}$ is a $C_1$-$C_{15}$ divalent hydrocarbon group, examples of which are the ones exemplified above for the monovalent hydrocarbon groups, with one hydrogen atom being eliminated. Two of $R^{L07}$ to $R^{L06}$ which are attached to vicinal carbon atoms may bond together directly to form a double bond (for example, a pair of $R^{L07}$ and $R^{L09}$, $R^{L09}$ and $R^{L15}$, $R^{L13}$ and $R^{L15}$, $R^{L14}$ and $R^{L15}$, or a similar pair).

Of the acid labile groups of formula (L1), the straight and branched ones are exemplified by the following groups.

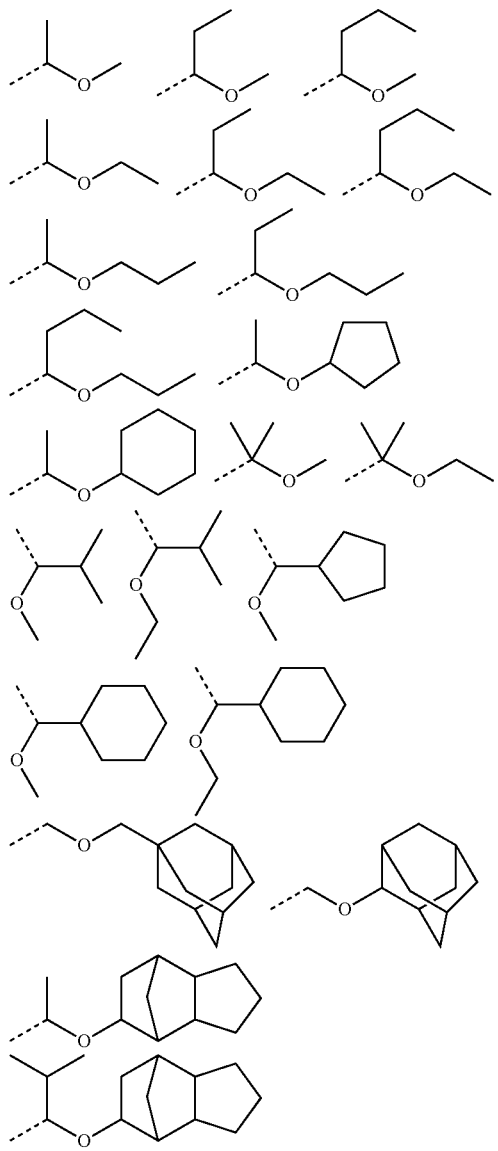

Of the acid labile groups of formula (L1), the cyclic ones are, for example, tetrahydrofuran-2-yl, 2-methyltetrahydrofuran-2-yl, tetrahydropyran-2-yl, and 2-methyltetrahydropyran-2-yl.

Examples of the acid labile groups of formula (L2) include tert-butoxycarbonyl, tert-butoxycarbonylmethyl, tert-pentyloxycarbonyl, tert-pentyloxycarbonylmethyl, 1,1-diethylpropyloxycarbonyl, 1,1-diethylpropyloxycarbonylmethyl, 1-ethylcyclopentyloxycarbonyl, 1-ethylcyclopentyloxycarbonylmethyl, 1-ethyl-2-cyclopentenyloxycarbonyl, 1-ethyl-2-cyclopentenyloxycarbonylmethyl, 1-ethoxyethoxycarbonylmethyl, 2-tetrahydropyranyloxycarbonylmethyl, and 2-tetrahydrofuranyloxycarbonylmethyl groups.

Examples of the acid labile groups of formula (L3) include 1-methyleyclopentyl, 1-ethyleyclopentyl, 1-n-propylcyclopentyl, 1-isopropylcyclopentyl, 1-n-butylcyclopentyl, 1-sec-butylcyclopentyl, 1-cyclohexylcyclopentyl, 1-(4-methoxy-n-butyl)cyclopentyl, 1-methylcyclohexyl, 1-ethylcyclohexyl, 3-methyl-1-cyclopenten-3-yl, 3-ethyl-1-cyclopenten-3-yl, 3-methyl-1-cyclohexen-3-yl, and 3-ethyl-1-cyclohexen-3-yl groups.

Of the acid labile groups having formula (L4), groups having the following formulas (L4-1) to (L4-4) are preferred.

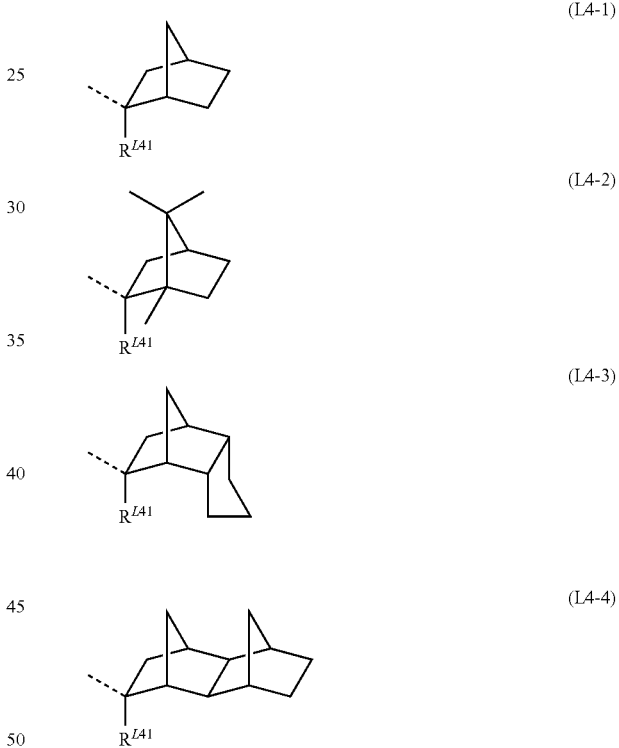

In formulas (L4-1) to (L4-4), the broken line denotes a bonding site and direction. $R^{L41}$ is each independently a monovalent hydrocarbon group, typically a $C_1$-$C_{10}$ straight, branched or cyclic alkyl group, such as methyl, ethyl, propyl, isopropyl, n-butyl, sec-butyl, tert-butyl, tert-pentyl, n-pentyl, n-hexyl, cyclopentyl and cyclohexyl.

For formulas (L4-1) to (L4-4), there can exist enantiomers and diastereomers. Each of formulae (L4-1) to (L4-4) collectively represents all such stereoisomers. When the acid labile group $X^A$ is of formula (L4), a plurality of stereoisomers may be included.

For example, the general formula (L4-3) represents one or a mixture of two selected from groups having the following general formulas (L4-3-1) and (L4-3-2).

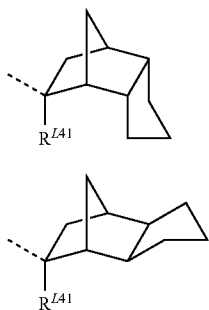
(L4-3-1)

(L4-3-2)

$R^{L41}$ is as defined above.

Similarly, the general formula (L4-4) represents one or a mixture of two or more selected from groups having the following general formulas (L4-4-1) to (L4-4-4).

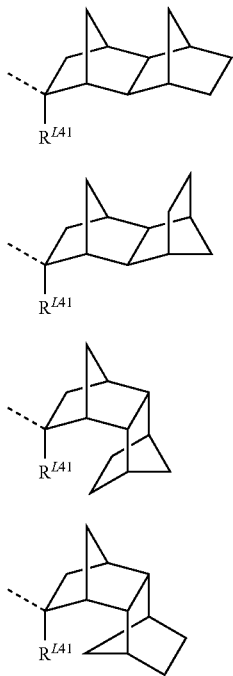
(L4-4-1)

(L4-4-2)

(L4-4-3)

(L4-4-4)

$R^{L41}$ is as defined above.

Each of formulas (L4-1) to (L4-4), (L4-3-1) and (L4-3-2), and (L4-4-1) to (L4-4-4) collectively represents an enantiomer thereof and a mixture of enantiomers.

It is noted that in the above formulas (L4-1) to (L4-4), (L4-3-1) and (L4-3-2), and (L4-4-1) to (L4-4-4), the bond direction is on the exo side relative to the bicyclo[2.2.1] heptane ring, which ensures high reactivity for acid catalyzed elimination reaction (see JP-A 2000-336121). In preparing these monomers having a tertiary exo-alkyl group of bicyclo[2.2.1]heptane skeleton as a substituent group, there may be contained monomers substituted with an endo-alkyl group as represented by the following formulas (L4-1-endo) to (L4-4-endo). For good reactivity, an exo proportion of at least 50 mol % is preferred, with an exo proportion of at least 80 mol % being more preferred.

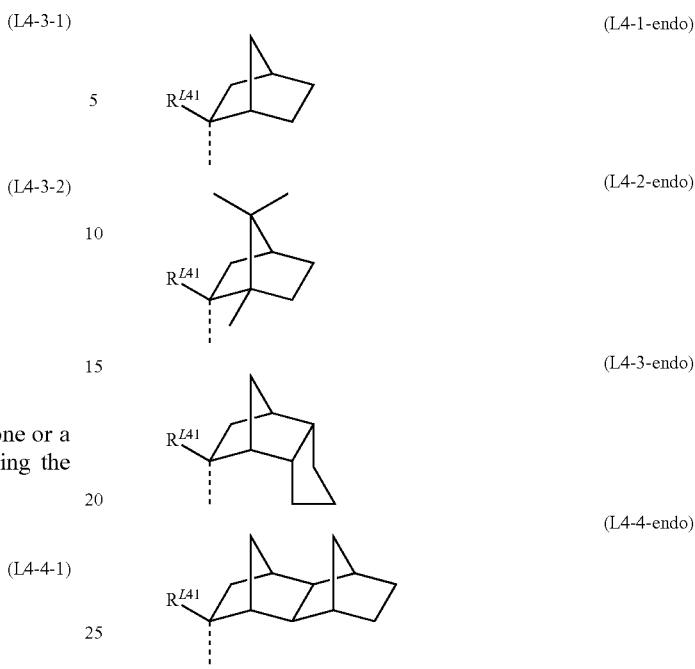
(L4-1-endo)

(L4-2-endo)

(L4-3-endo)

(L4-4-endo)

$R^{L41}$ is as defined above,

Illustrative examples of the acid labile group of formula (L4) are given below

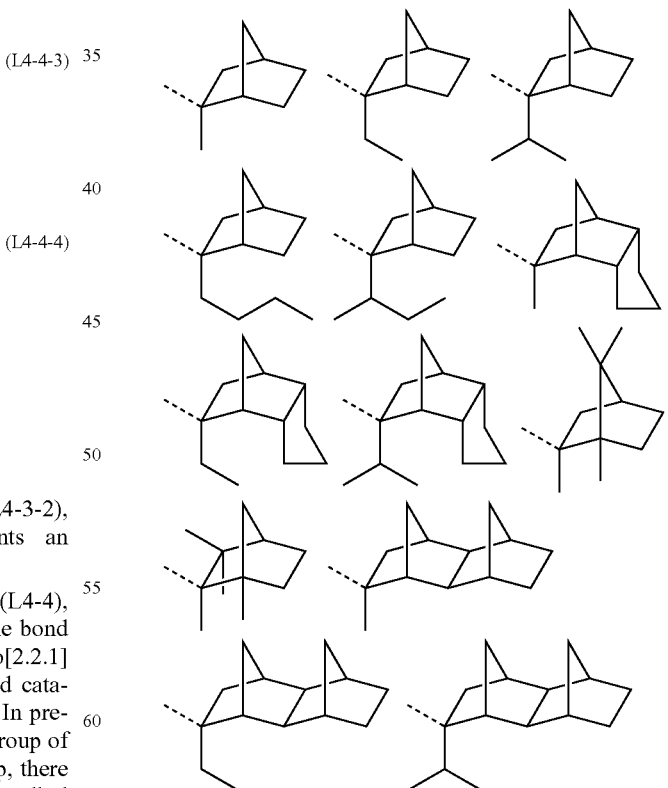

Examples of the $C_4$-$C_{20}$ tertiary alkyl groups, trialkylsilyl groups in which each alkyl moiety has 1 to 6 carbon atoms, and $C_4$-$C_{20}$ oxoalkyl groups are as exemplified for $R^{L04}$.

Illustrative examples of the recurring units of formula (a) are given below, but not limited thereto. $R^A$ is as defined above.
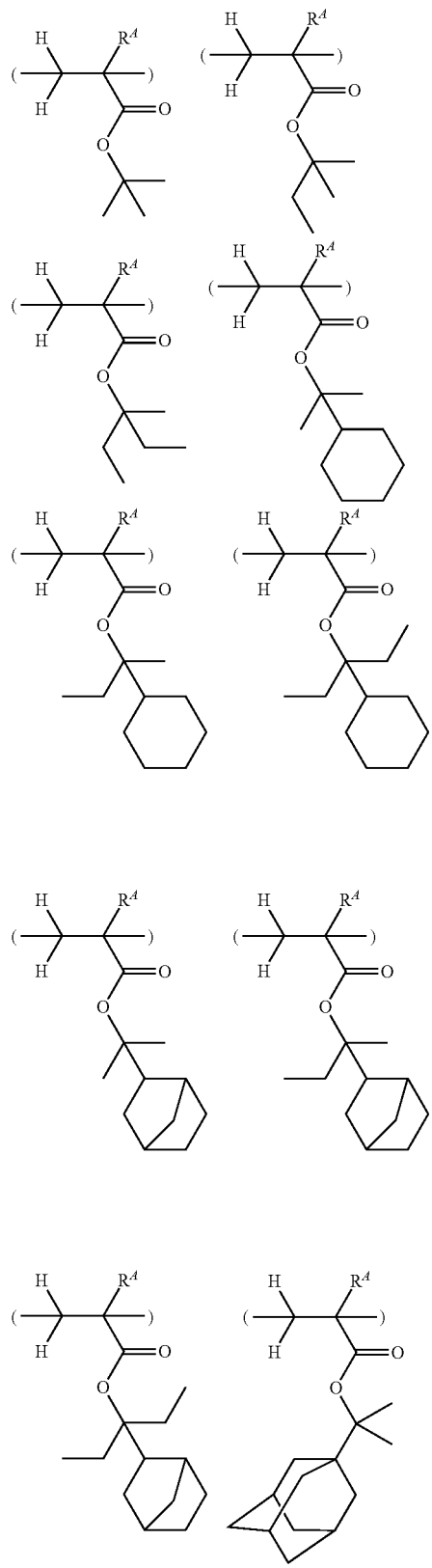
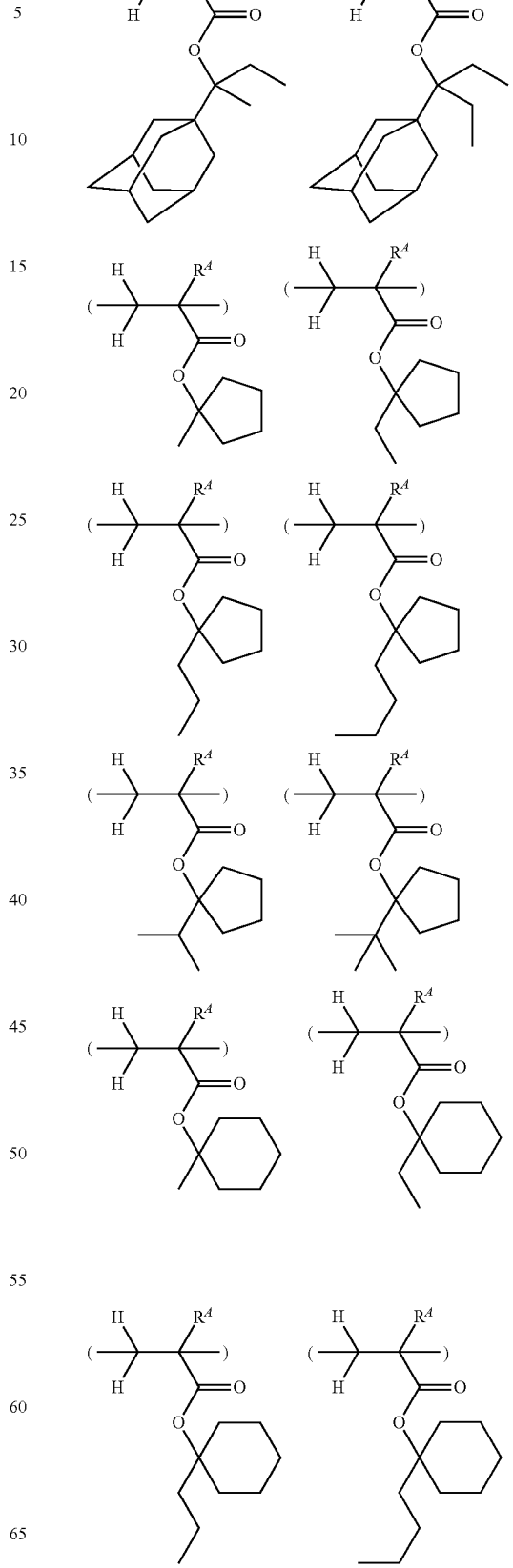

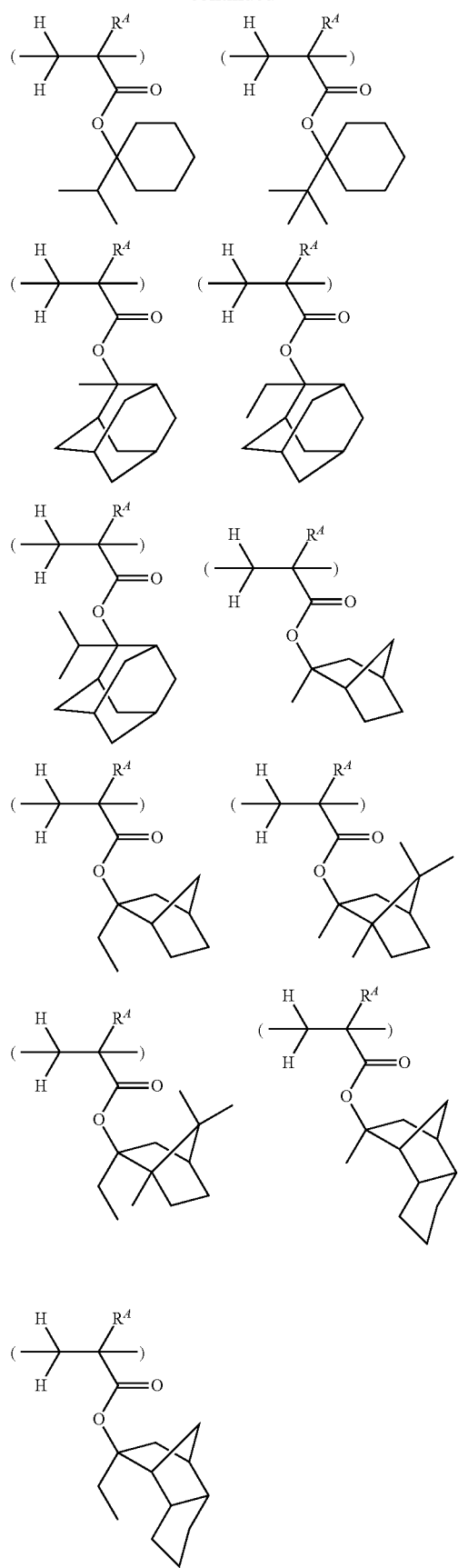
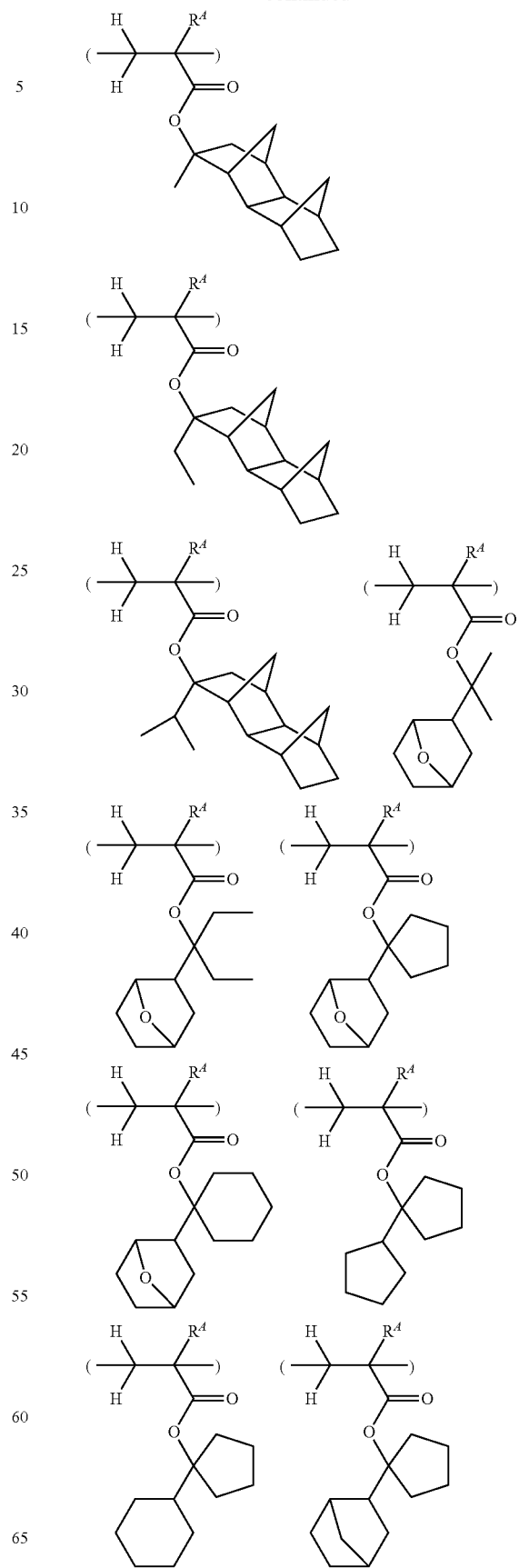

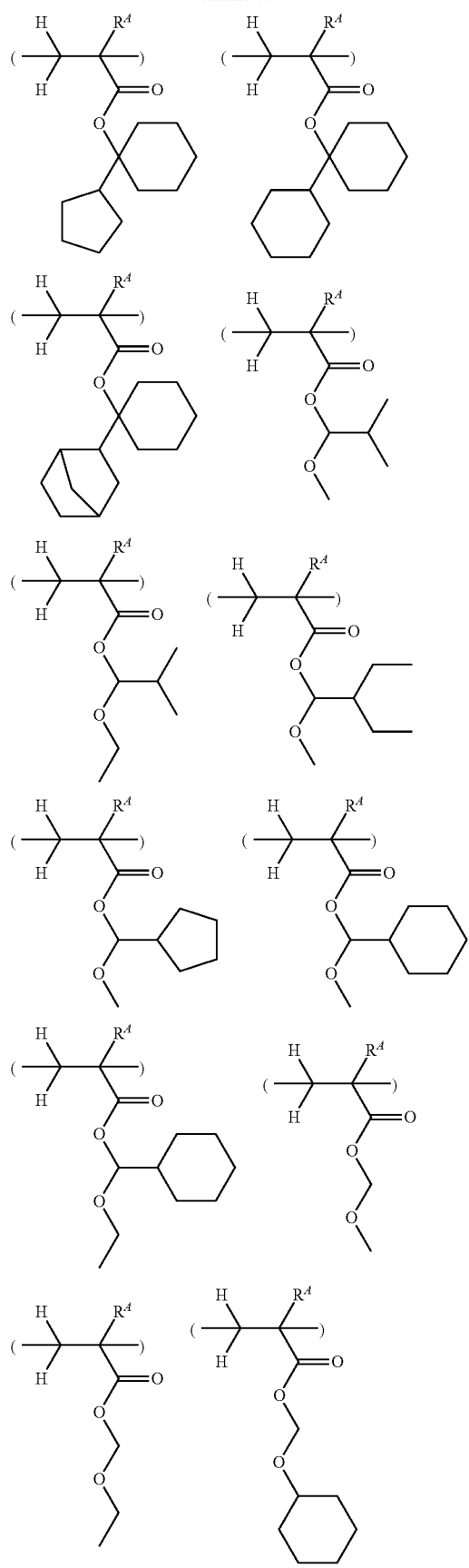
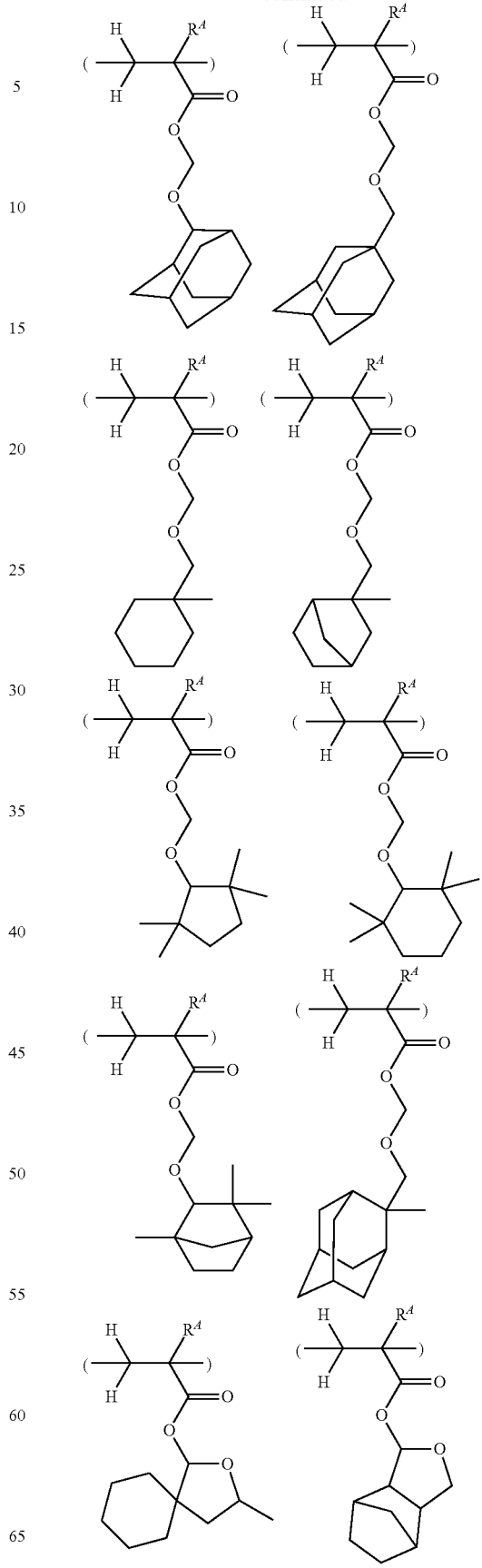

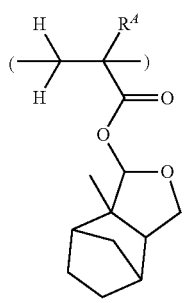

The above examples correspond to those units of formula (a) wherein $Z^A$ is a single bond. Where $Z^A$ is other than a single bond, a combination with a similar acid labile group is possible. Thus examples of the recurring units of formula (a) wherein $Z^A$ is other than a single bond are as illustrated above.

Illustrative examples of the recurring units of formula (b) are given below, but not limited thereto. $R^A$ is as defined above.

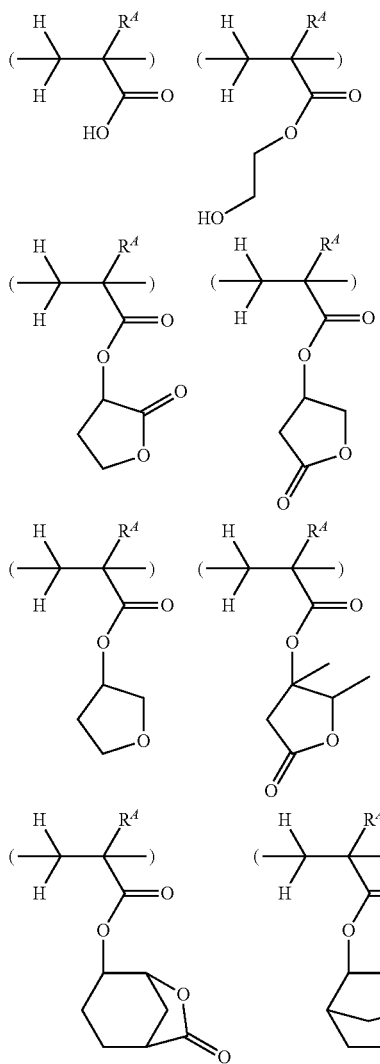
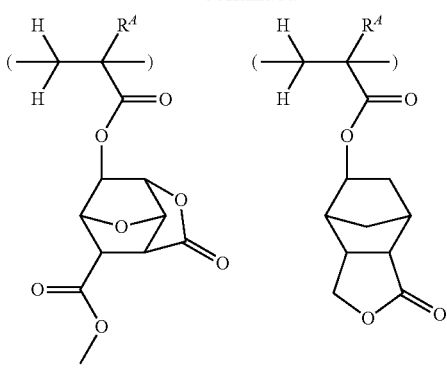
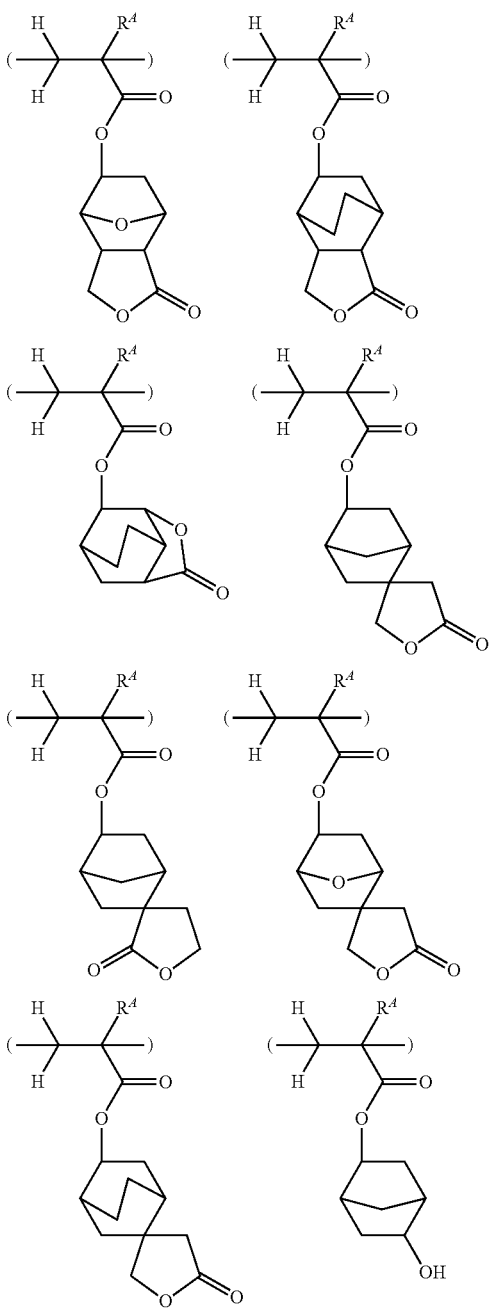

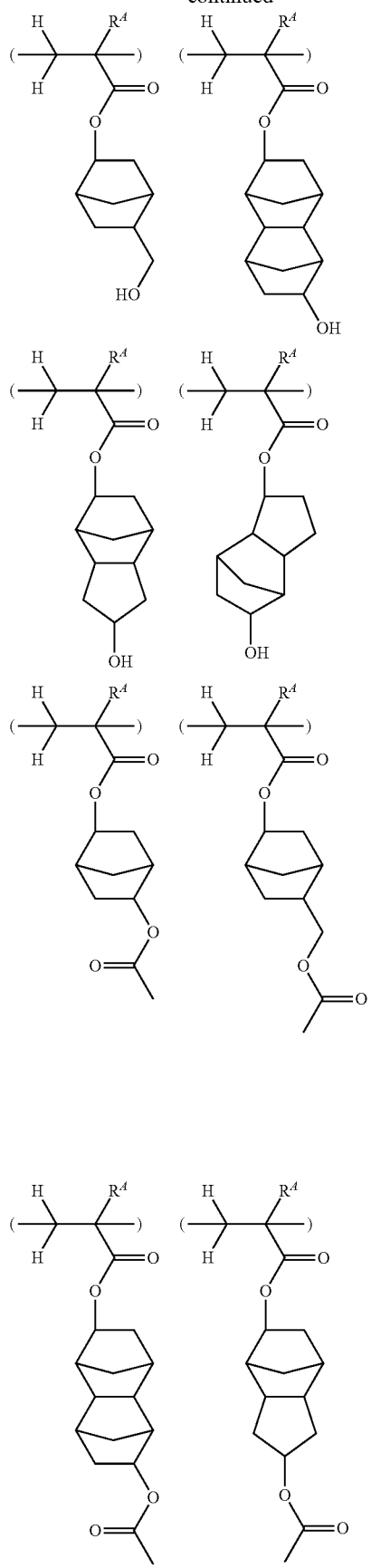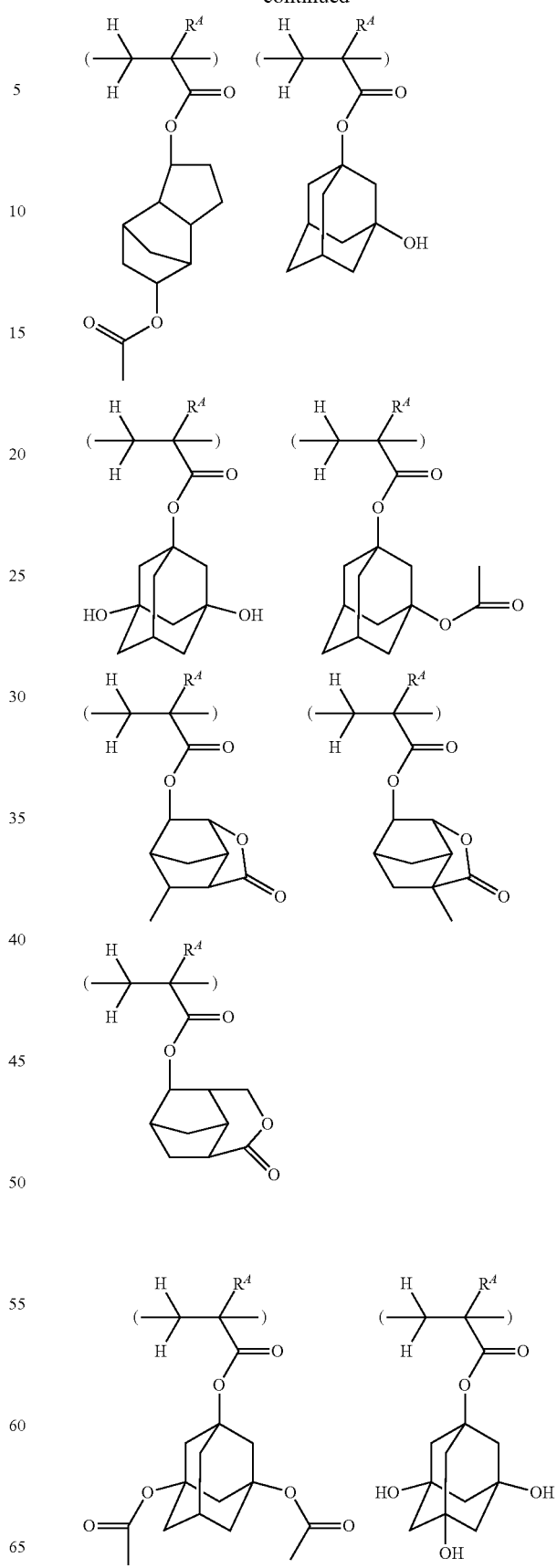

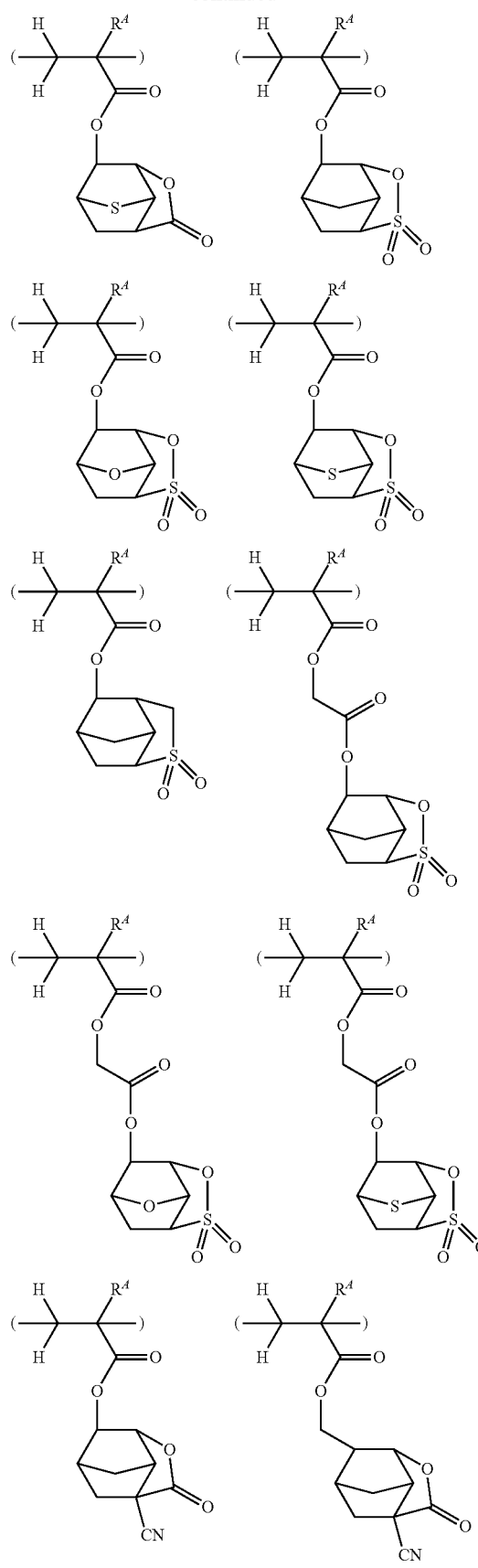
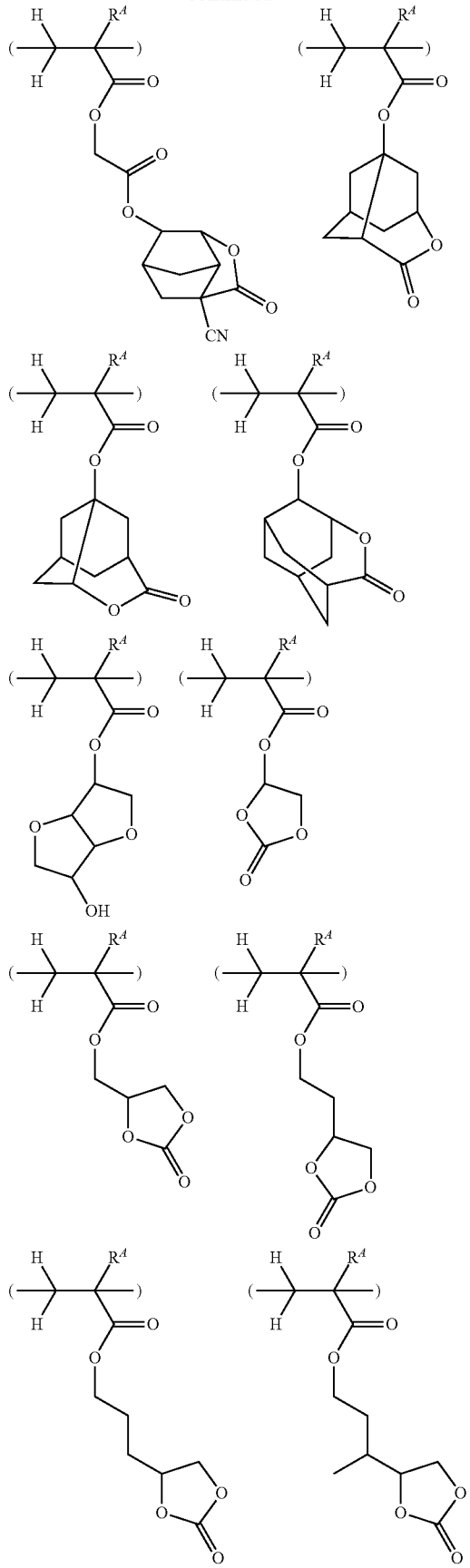

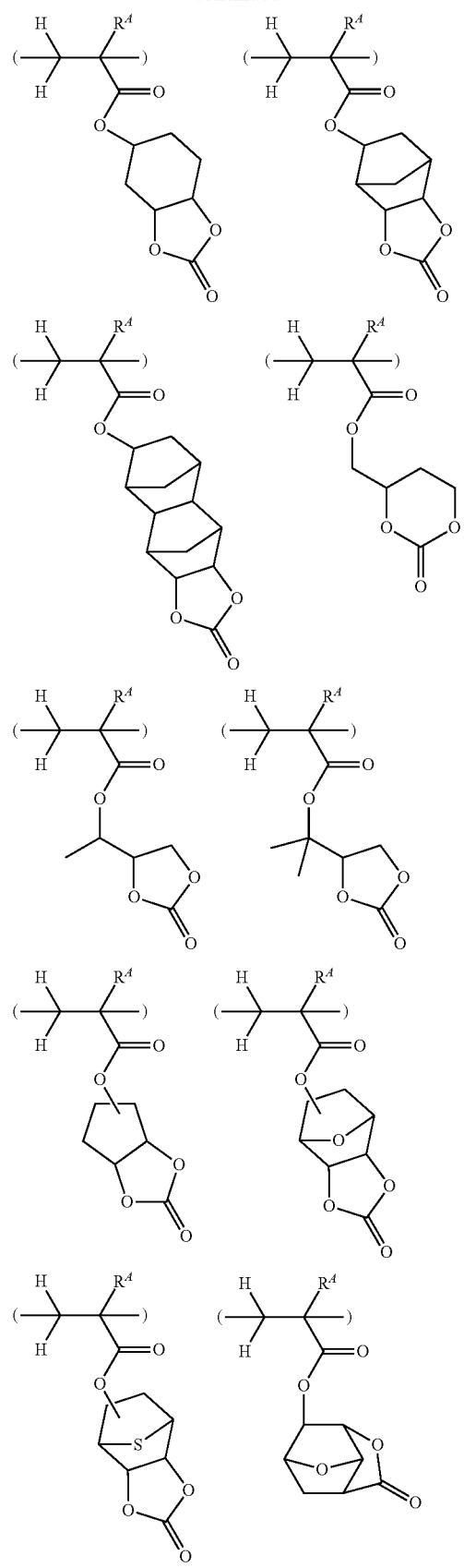
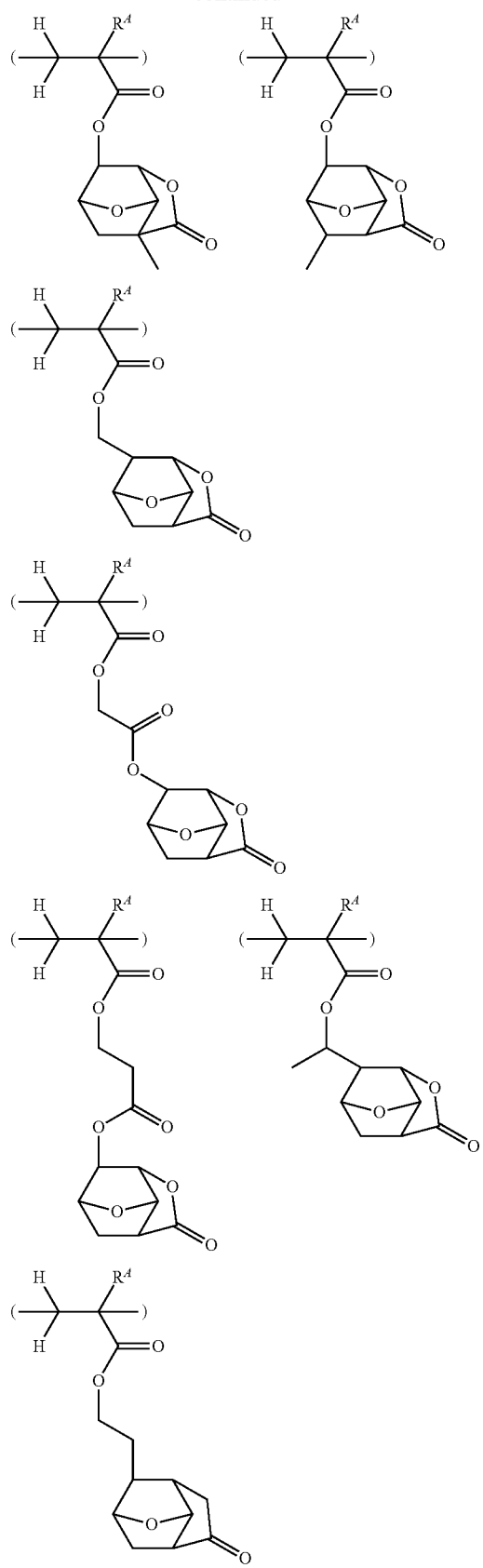

-continued
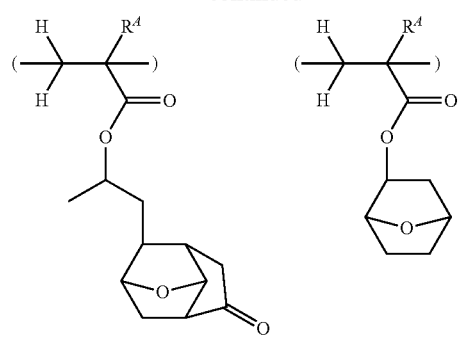
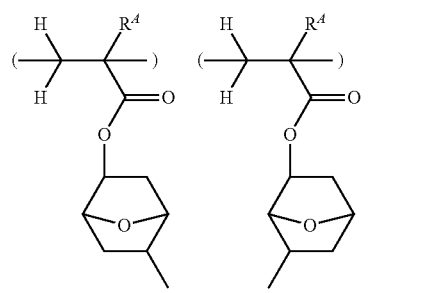
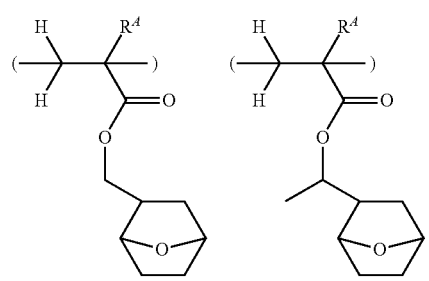
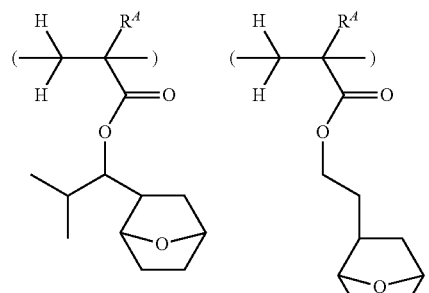
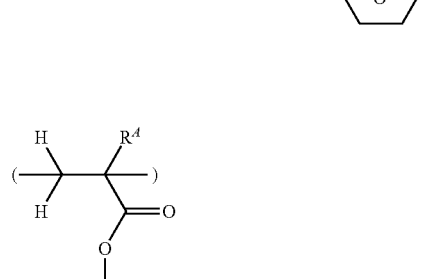
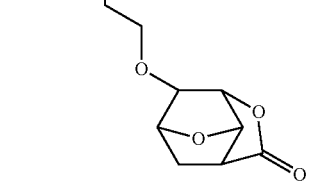
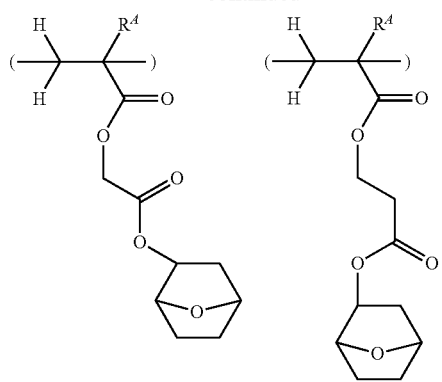
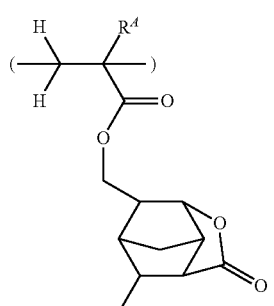
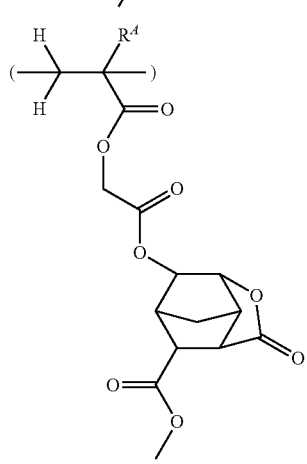
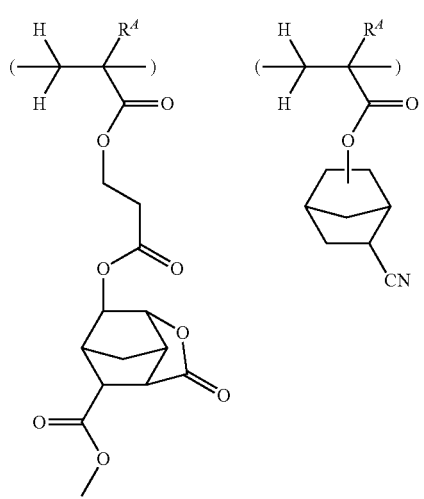

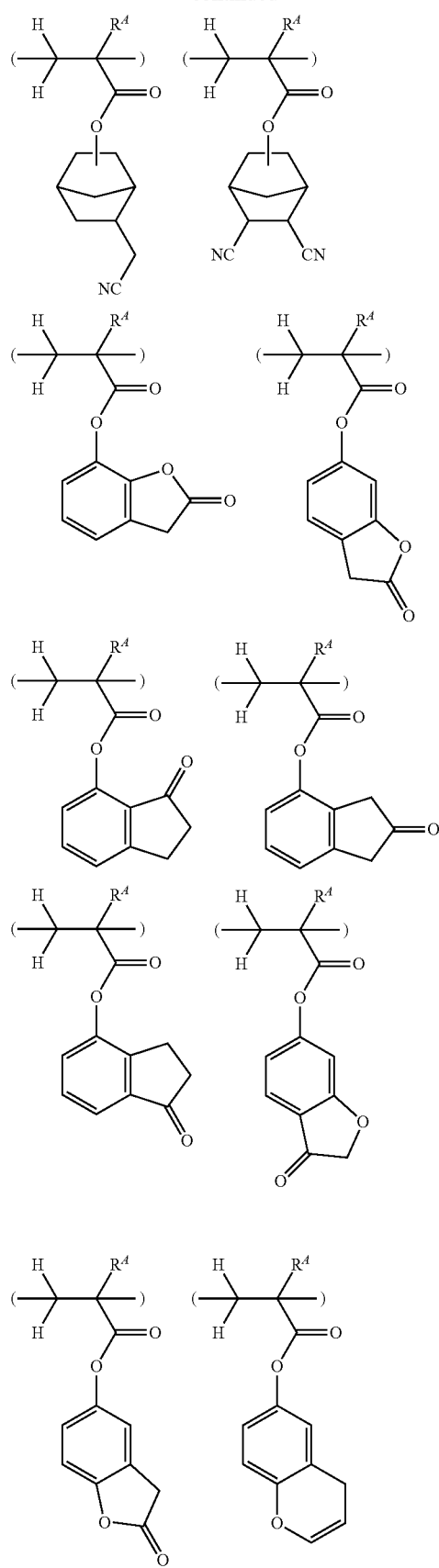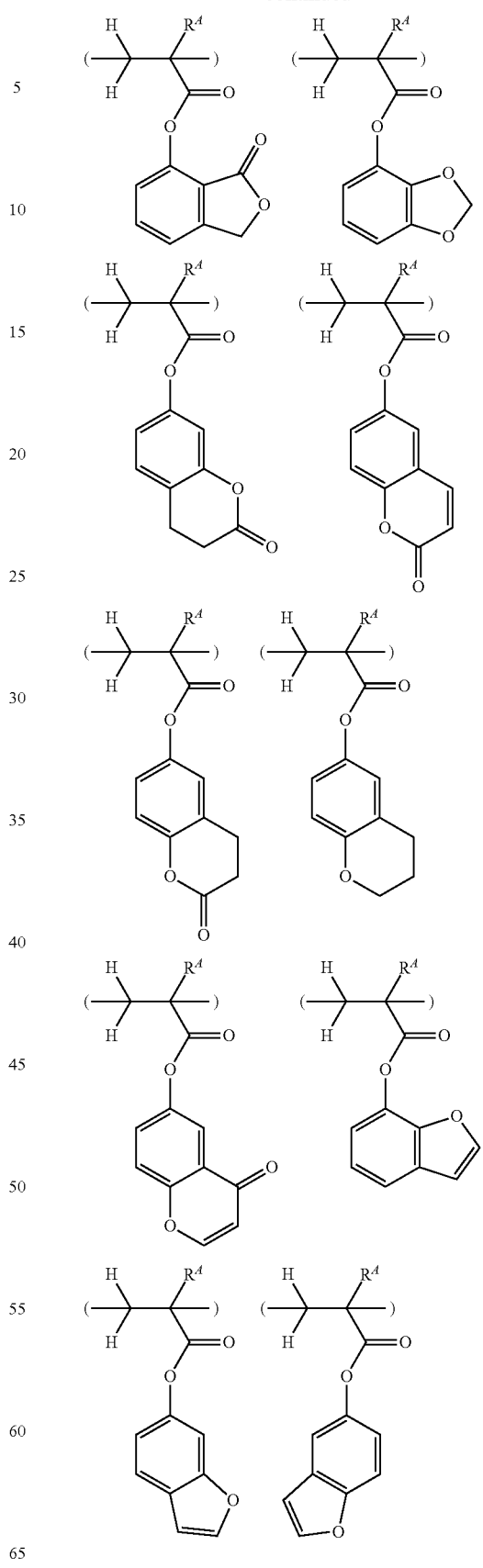

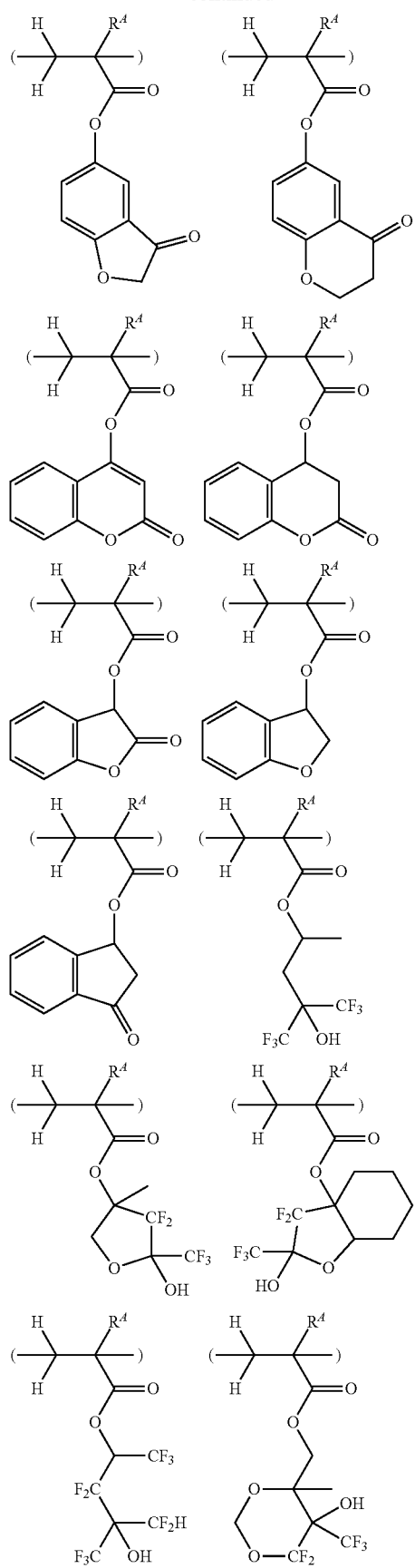
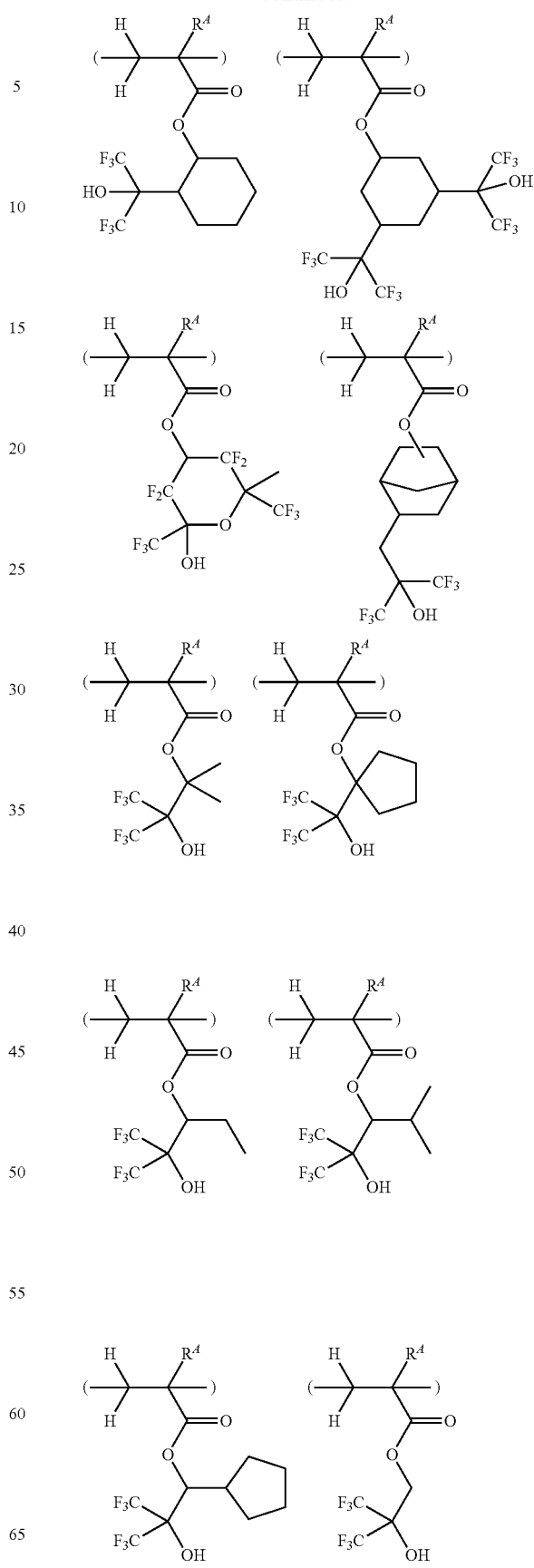

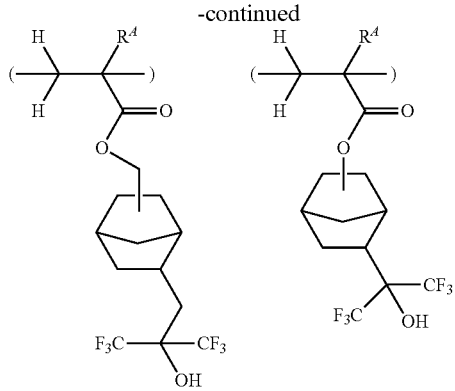
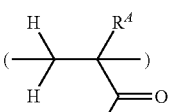
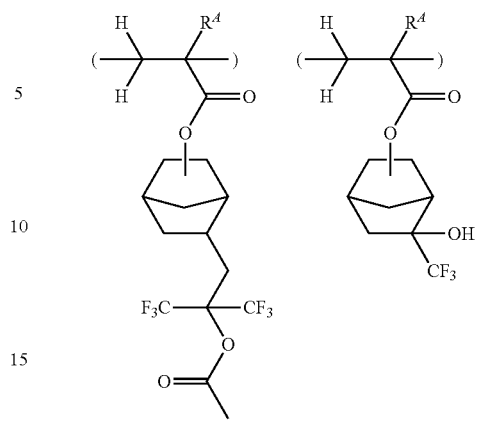
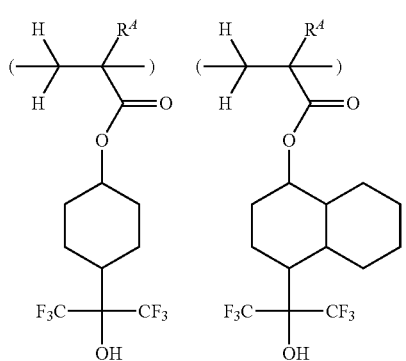
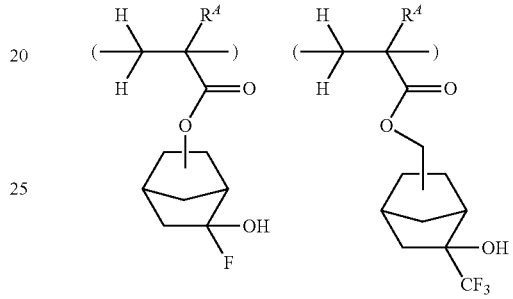
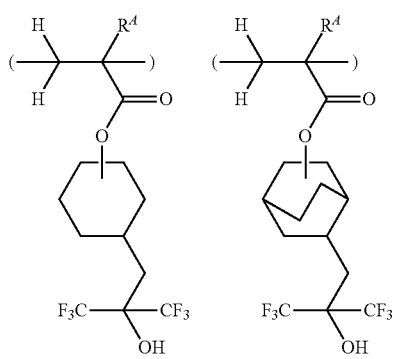
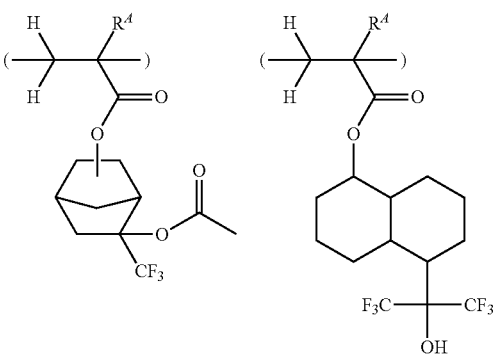
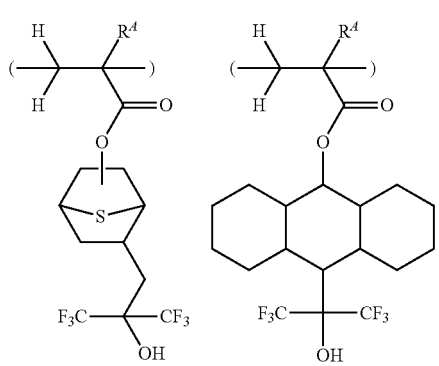
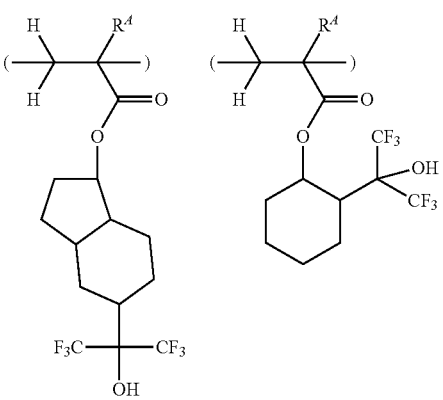

-continued
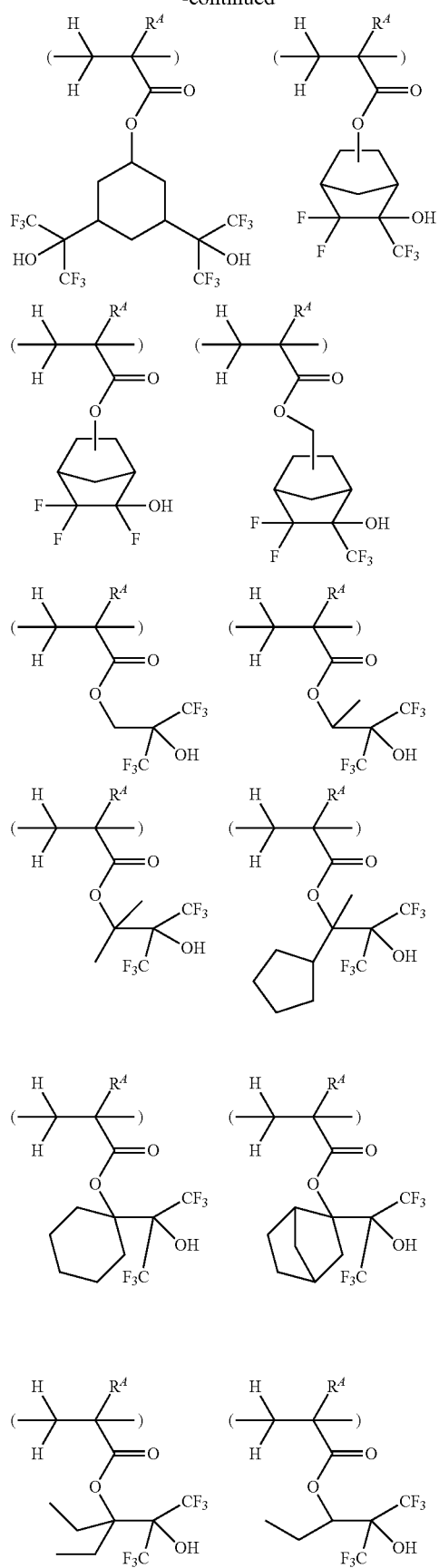
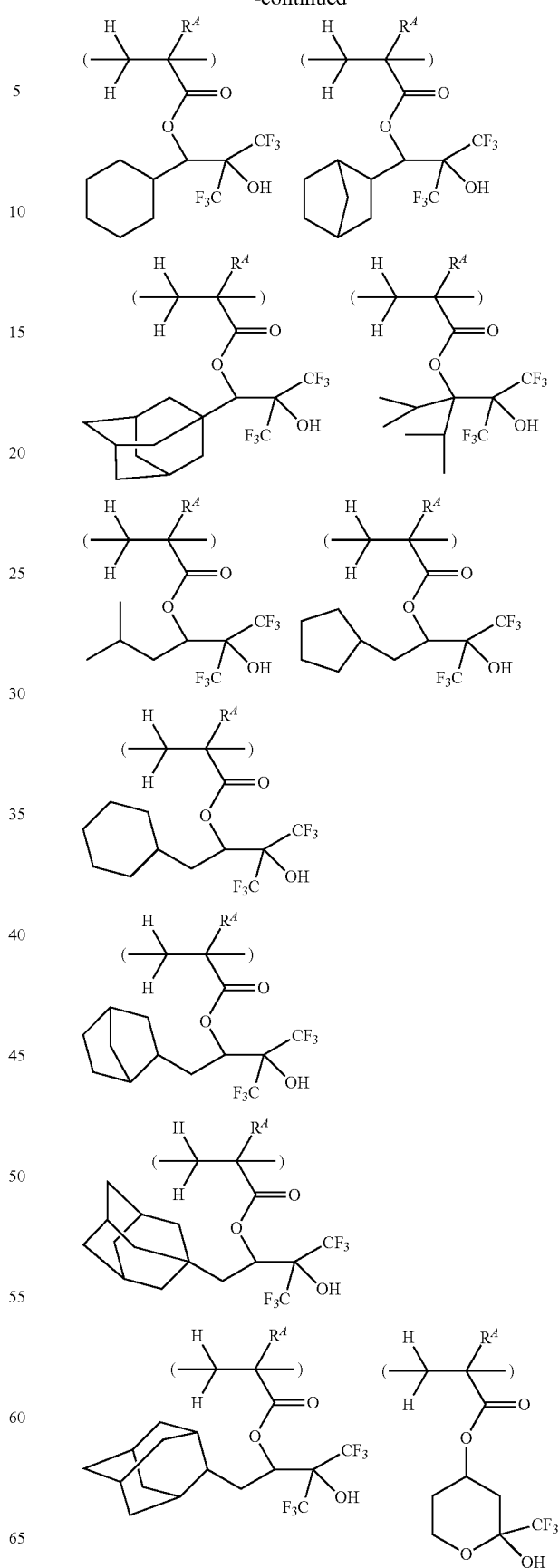

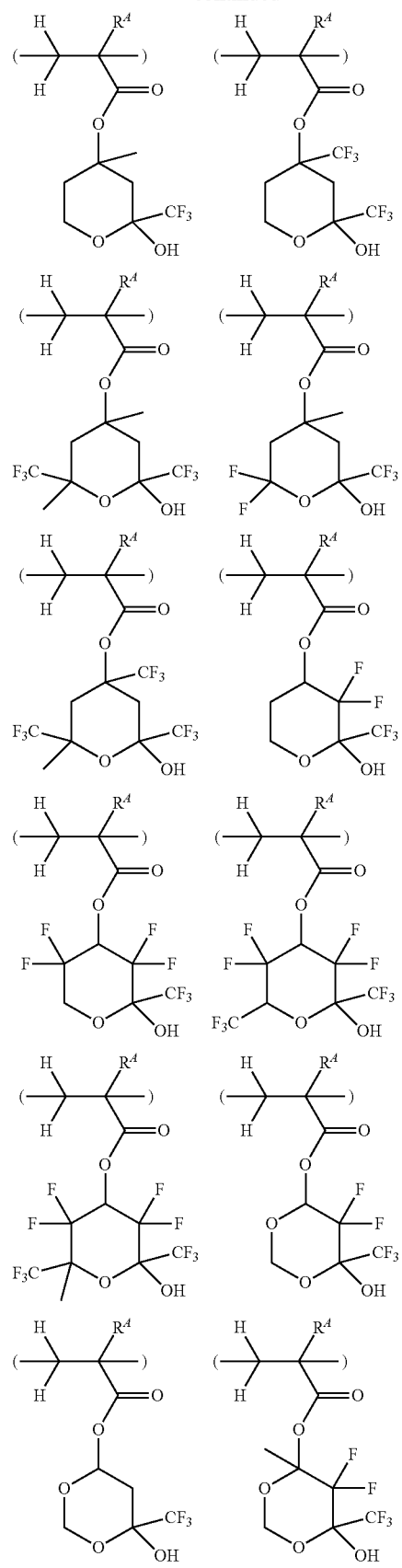
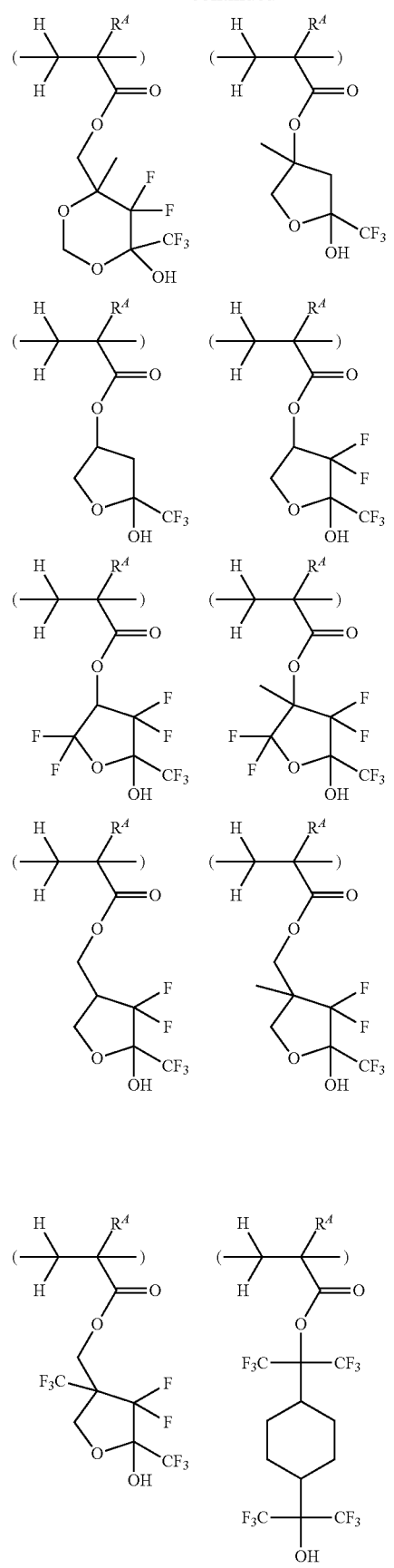

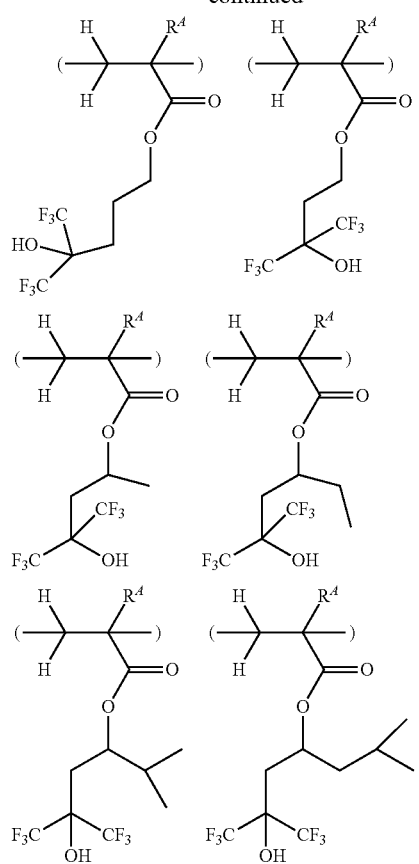
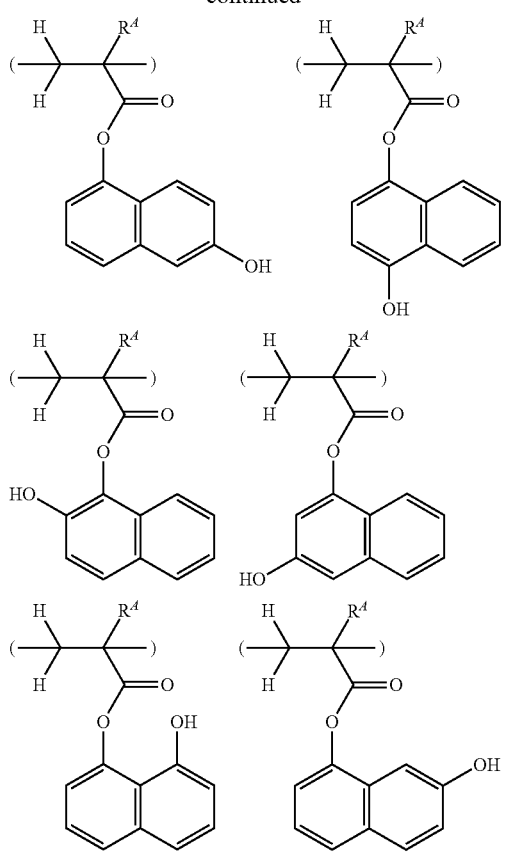
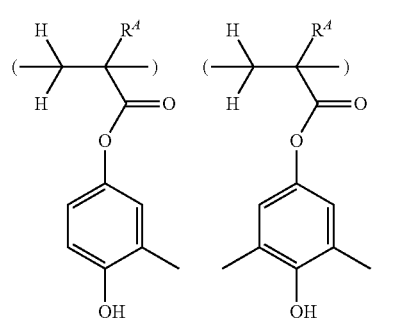
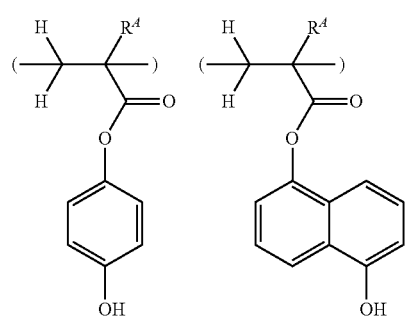

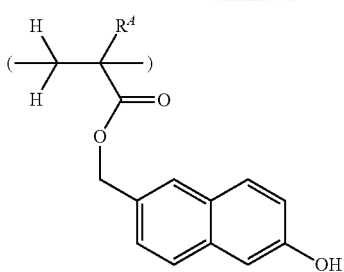
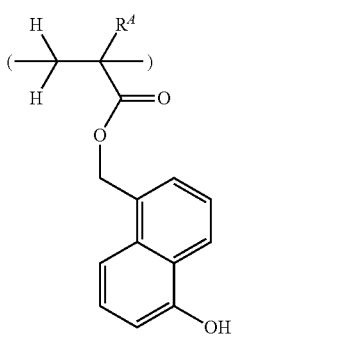
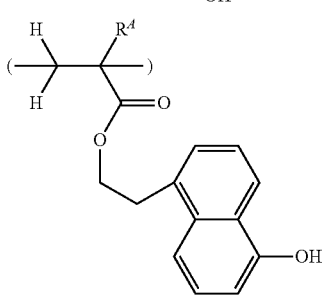
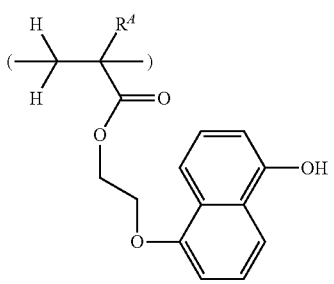
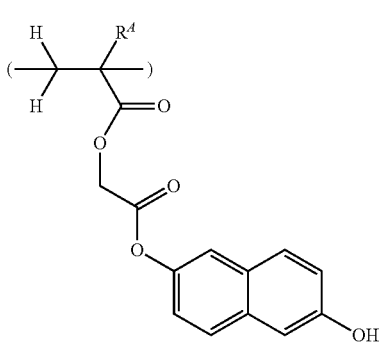

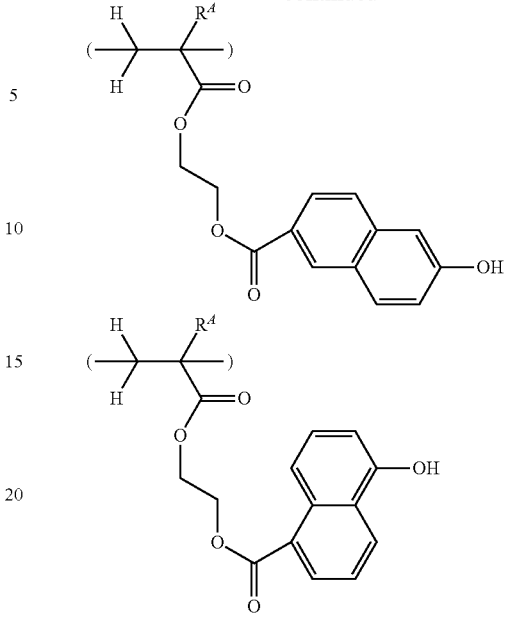

Among the recurring units of formula (b), units having lactone ring as the polar group are most preferred.

While the polymer is characterized by comprising recurring units having formulae (a) and (b), it may further comprise recurring units of at least one type selected from recurring units having the formulae (c1) to (c3).

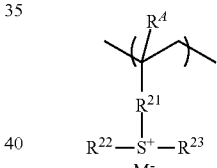 (c1)

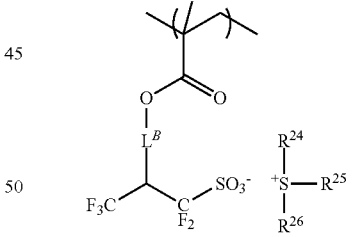 (c2)

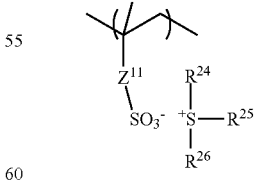 (c3)

Herein $R^A$ is as defined above. $R^{21}$ is a single bond, phenylene, —O—$R^{31}$—, or —C(=O)—$Z^{22}$—$R^{31}$—, wherein $Z^{22}$ is —O— or —NH—, and $R^{31}$ is a $C_1$-$C_6$ straight, branched or cyclic alkylene group, $C_2$-$C_6$ straight, branched or cyclic alkenylene group or phenylene group, which may contain a carbonyl (—CO—), ester (—COO—), ether (—O—) or hydroxyl moiety. $L^B$ is a single bond or —$Z^{33}$—C(=O)—O—, wherein $Z^{33}$ is a $C_1$-$C_{20}$ straight, branched or cyclic divalent hydrocarbon group which may contain a heteroatom. $Z^{11}$ is a single bond, methylene, ethylene, phenylene, fluorinated phenylene, —O—$R^{32}$—, or —C(=O)—$Z^{44}$—$R^{32}$ wherein $Z^{44}$ is —O— or —NH—, and $R^{32}$ is a $C_1$-$C_6$ straight, branched or cyclic alkylene, $C_2$-$C_6$ straight, branched or cyclic alkenylene or phenylene group, which may contain a carbonyl, ester, ether or hydroxyl moiety. $R^{22}$ to $R^{26}$ are each independently a $C_1$-$C_{20}$ straight, branched or cyclic monovalent hydrocarbon group which may contain a heteroatom, or any two of $R^{21}$, $R^{22}$ and $R^{23}$ may bond together to form a ring with the sulfur atom in the formula, any two of $R^{24}$, $R^{25}$ and $R^{26}$ may bond together to form a ring with the sulfur atom in the formula, $M^-$ is a non-nucleophilic counter ion.

Suitable monovalent hydrocarbon groups $R^{22}$ to $R^{26}$ include, but are not limited to, alkyl groups such as methyl, ethyl, n-propyl, isopropyl, n-butyl, t-butyl, cyclopropyl, cyclopentyl, cyclohexyl, cyclopropylmethyl, 4-methylcyclohexyl, cyclohexylmethyl, norbornyl, and adamantyl; alkenyl groups such as vinyl, allyl, propenyl, butenyl, hexenyl, and cyclohexenyl; aryl groups such as phenyl, naphthyl and thienyl; and aralkyl groups such as benzyl, 1-phenylethyl and 2-phenylethyl, with the aryl groups being preferred. In the foregoing groups, one or more hydrogen atoms may be substituted by a substituent containing a heteroatom such as oxygen, sulfur, nitrogen or halogen, or a substituent containing a heteroatom such as oxygen, sulfur or nitrogen may intervene between carbon atoms, so that the group may contain a hydroxyl, cyano, carbonyl, ether bond, ester bond, sulfonic acid ester bond, carbonate bond, lactone ring, sultone ring, carboxylic anhydride or haloalkyl moiety. Any two of $R^{21}$, $R^{22}$ and $R^{23}$ may bond together to form a ring with the sulfur atom in the formula, and any two of $R^{24}$, $R^{25}$ and $R^{26}$ may bond together to form a ring with the sulfur atom in the formula.

When $L^B$ is —$Z^{33}$—C(=O)—O—, examples of the optionally heteroatom-containing, $C_1$-$C_{20}$ straight, branched or cyclic divalent hydrocarbon group $Z^{33}$ are shown below, but not limited thereto.

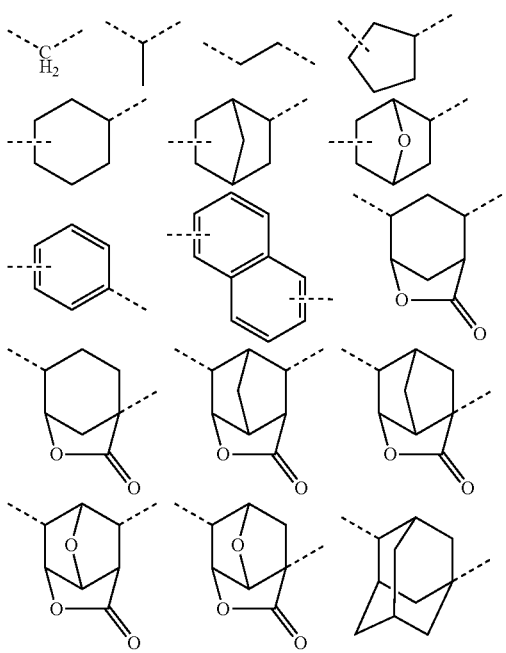

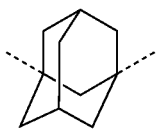

Any two of $R^{24}$, $R^{25}$ and $R^{26}$ may bond together to form a ring with the sulfur atom in the formula. Examples of the cation where two R's form a ring are shown below.

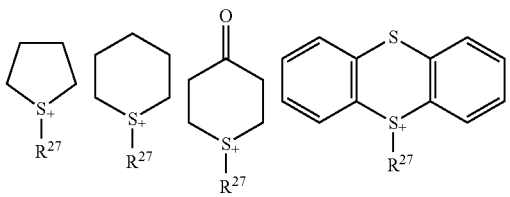

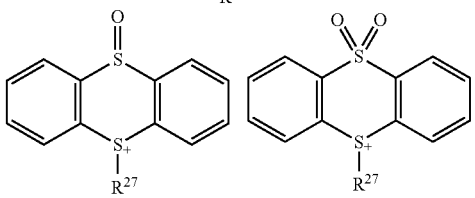

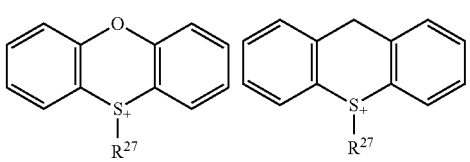

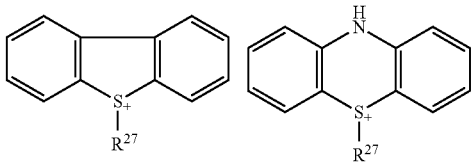

Herein $R^{27}$ is a $C_1$-$C_{20}$ straight, branched or cyclic monovalent hydrocarbon group which may contain a heteroatom. Examples of the monovalent hydrocarbon group are as exemplified above for $R^{22}$ to $R^{26}$.

Exemplary structures of the sulfonium cation in formulae (c2) and (c3) are shown below, but not limited thereto.

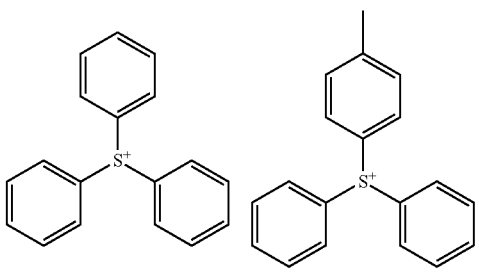

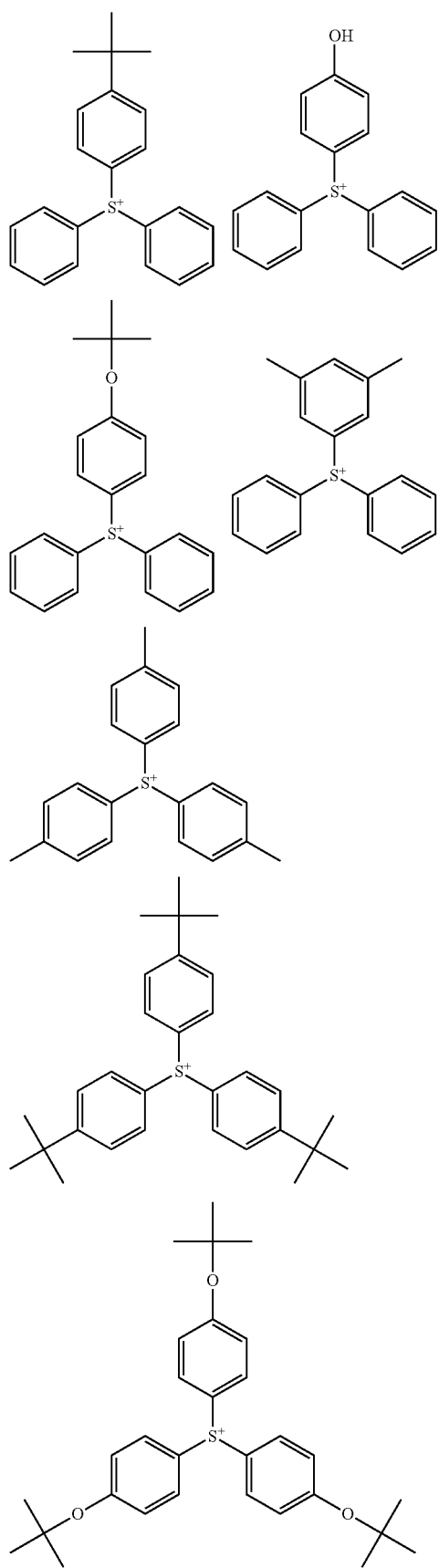
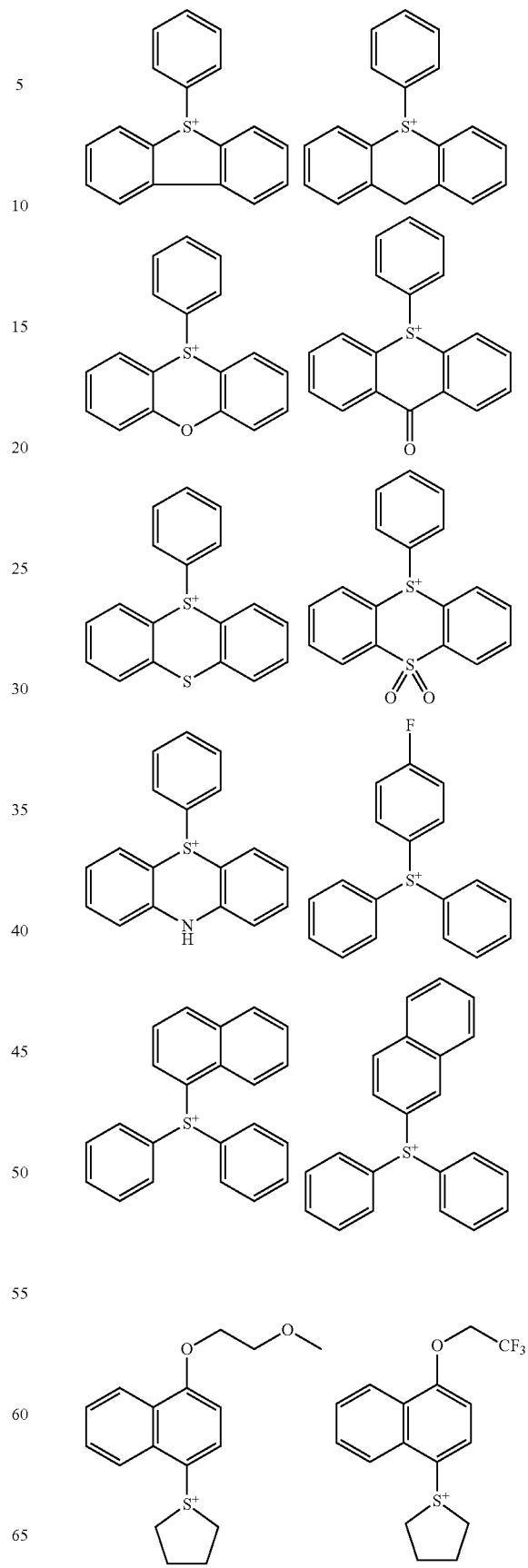

-continued

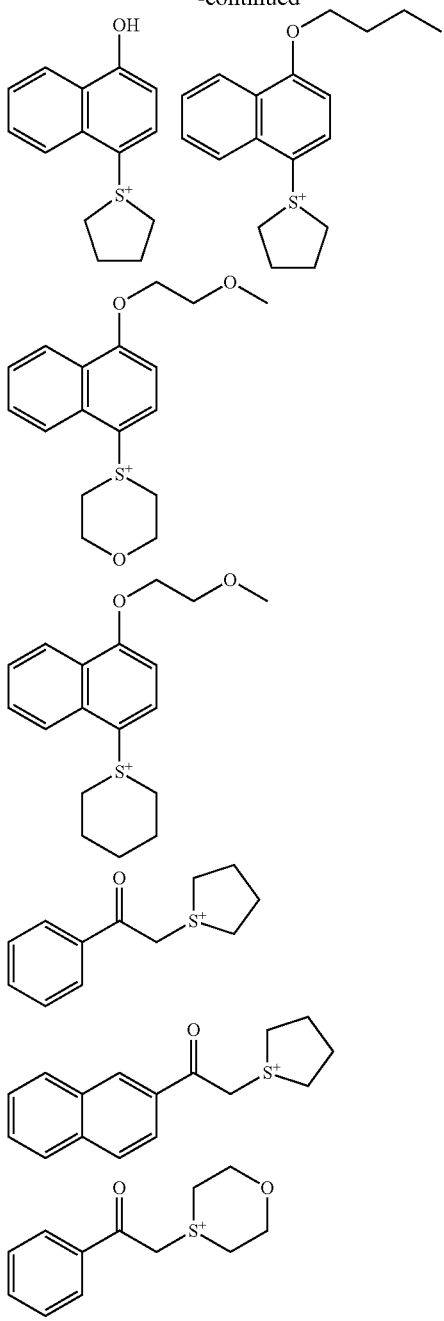

Examples of the non-nucleophilic counter ion M⁻ in formula (c1) include halide ions such as chloride and bromide ions; fluoroalkylsulfonate ions such as triflate, 1,1,1-trifluoroethanesulfonate, and nonafluorobutanesulfonate; arylsulfonate ions such as tosylate, benzenesulfonate, 4-fluorobenzenesulfonate, and 1,2,3,4,5-pentafluorobenzenesulfonate; alkylsulfonate ions such as mesylate and butanesulfonate; imidates such as bis(trifluoromethylsulfonyl)imide, bis(perfluoroethylsulfonyl)imide and bis(perfluorobutylsulfonyl)imide; methidates such as tris(trifluoromethylsulfonyl)methide and tris(perfluoroethylsulfonyl)methide.

Also included are a sulfonate anion which is fluorinated at α-position as represented by the formula (F-1) and a sulfonate anion which is fluorinated at α- and β-positions as represented by the formula (F-2).

In formula (F-1), $R^{51}$ is hydrogen, or a $C_1$-$C_{20}$ straight, branched or cyclic alkyl group, $C_2$-$C_{20}$ straight, branched or cyclic alkenyl group or $C_6$-$C_{20}$ aryl group, which may have an ether, ester, carbonyl moiety, lactone ring or fluorine atom. In formula (F-2), $R^{52}$ is hydrogen, or a $C_1$-$C_{30}$ straight, branched or cyclic alkyl group, $C_2$-$C_{30}$ straight, branched or cyclic acyl group, $C_2$-$C_{20}$ straight, branched or cyclic alkenyl group, $C_6$-$C_{20}$ aryl group, or $C_6$-$C_{20}$ aryloxy group, which may have an ether, ester, carbonyl moiety or lactone ring.

The polymer may further comprise recurring units of a structure having a hydroxyl group protected with an acid labile group. These recurring units are not particularly limited as long as at least one structure having a protected hydroxyl group is included and under the action of acid, the protective group is decomposed to generate a hydroxyl group. Units having the formula (d1) are preferred.

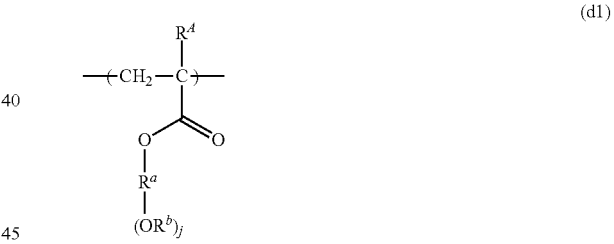

In formula (d1), $R^A$ is as defined above, $R^a$ is a $C_1$-$C_{30}$ straight, branched or cyclic, di- to penta-valent hydrocarbon group which may contain a heteroatom, $R^b$ is an acid labile group, and j is an integer of 1 to 4.

Examples of the recurring units having formula (d1) are shown below, but not limited thereto. $R^A$ and $R^b$ are as defined above.

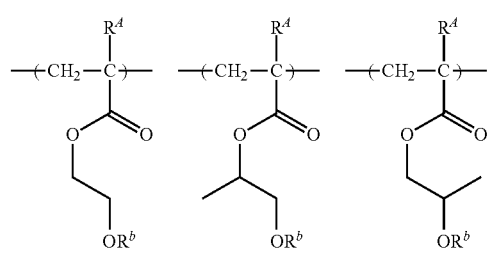

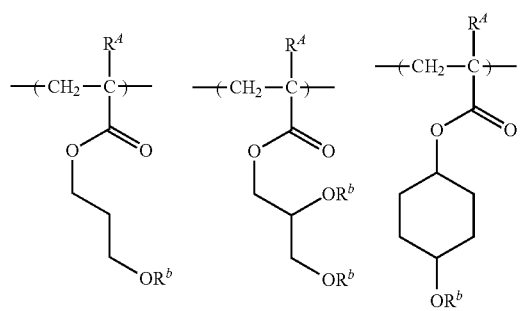
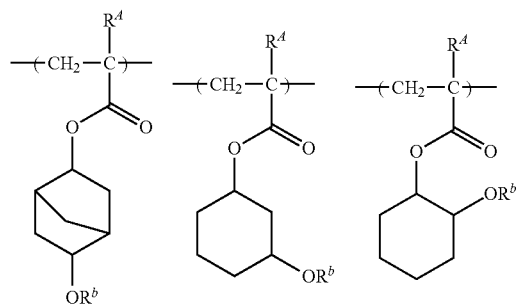
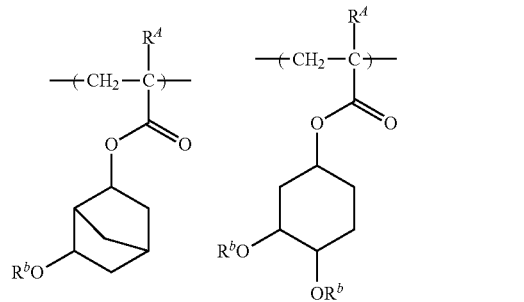
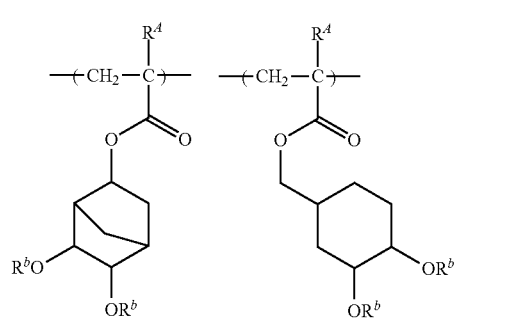
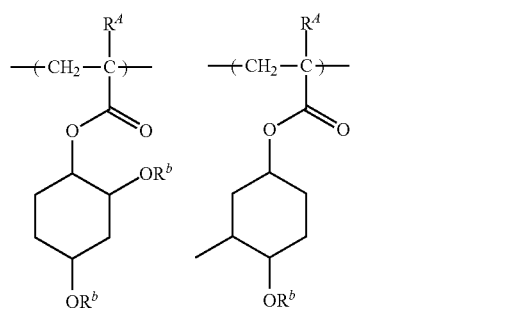
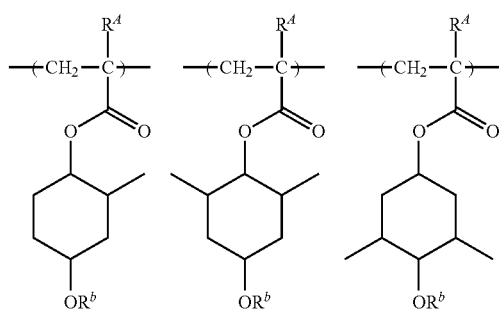
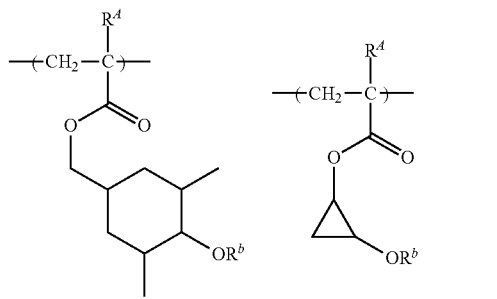
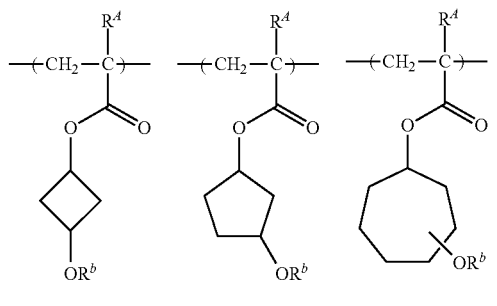
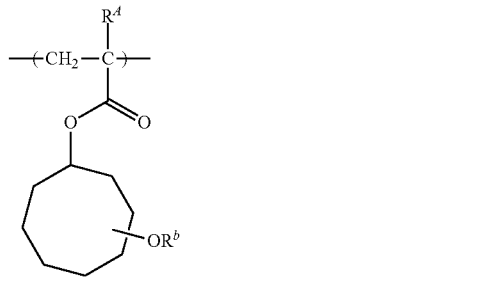
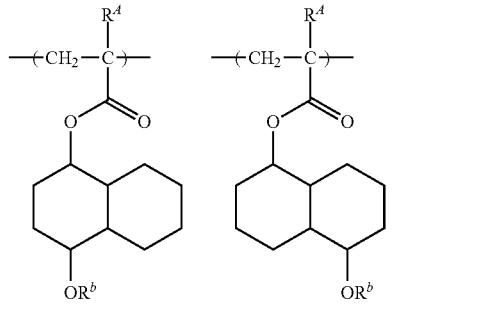

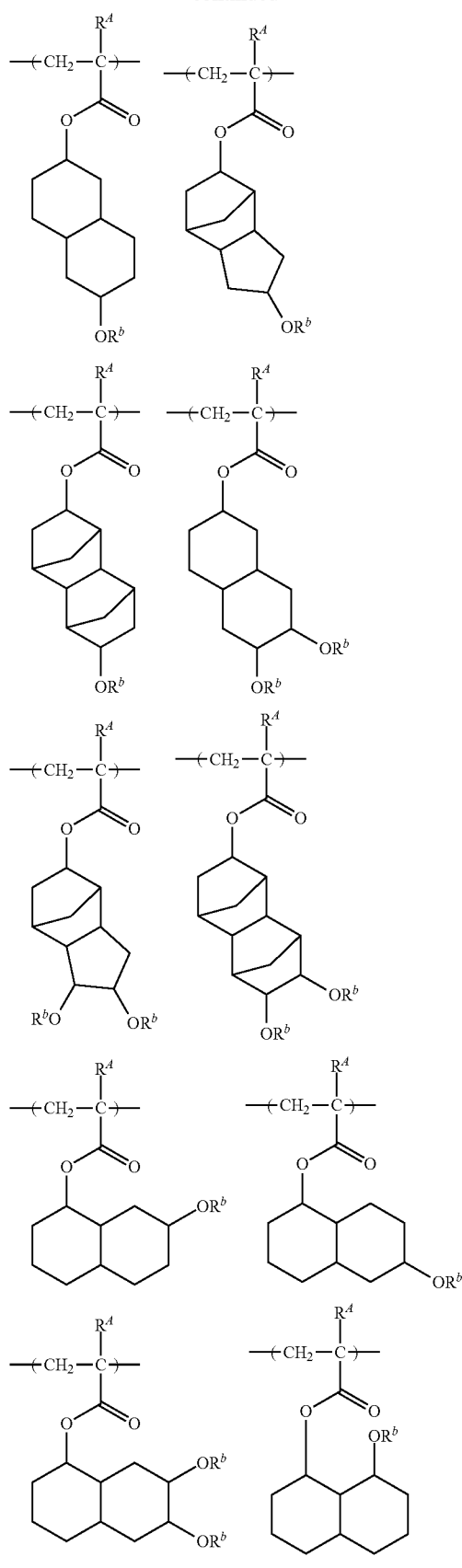
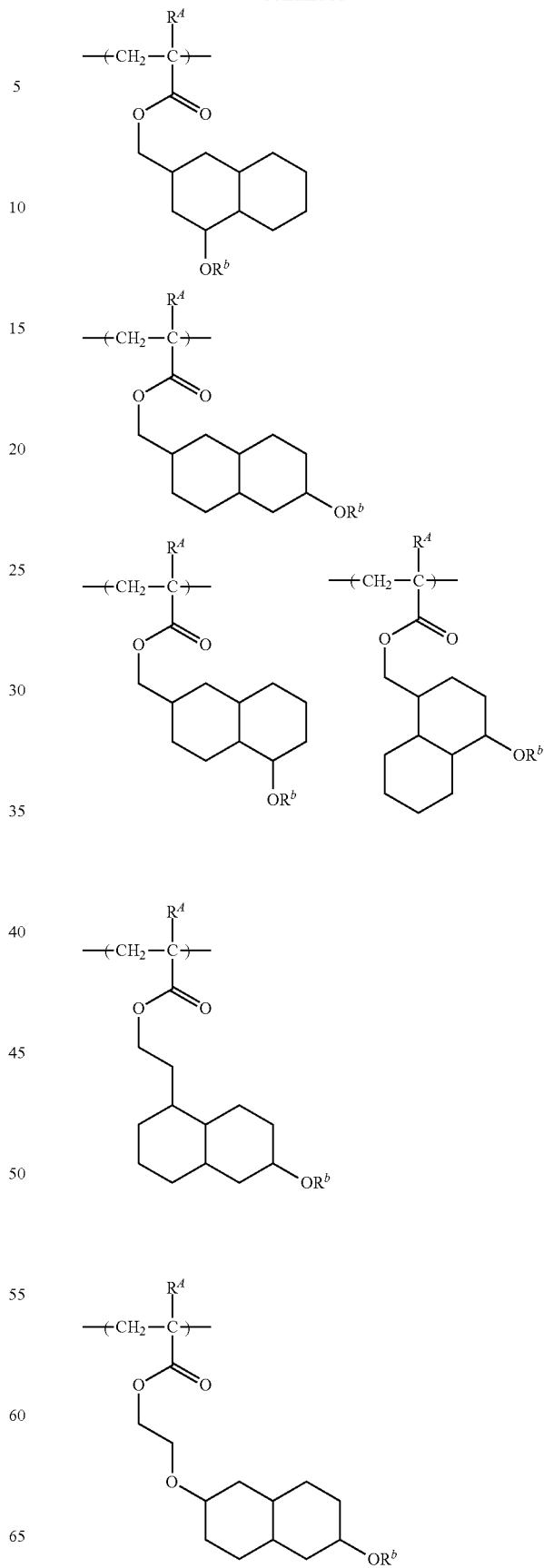

91
-continued
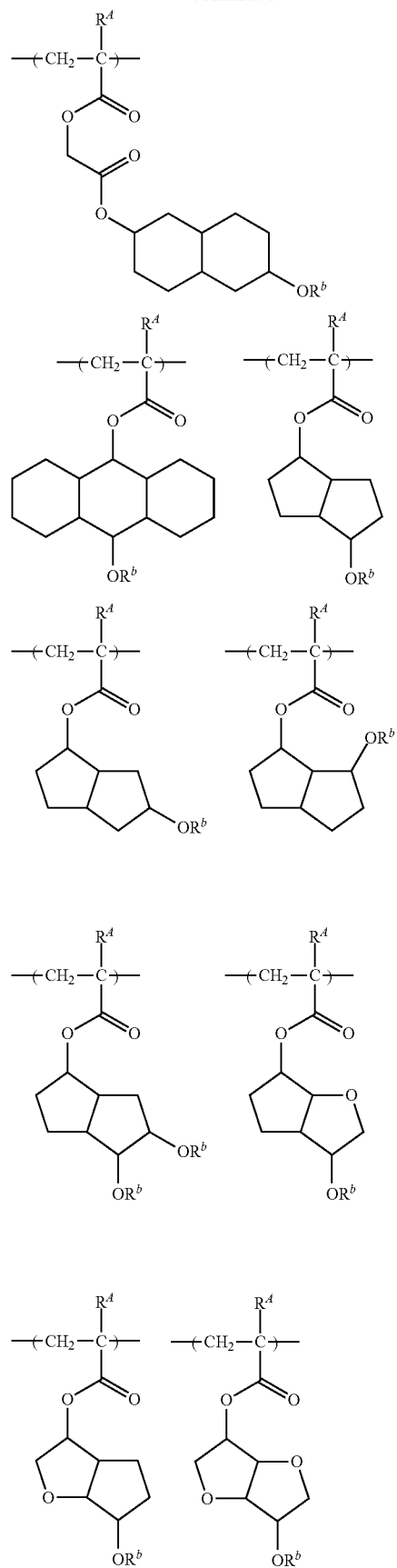
92
-continued
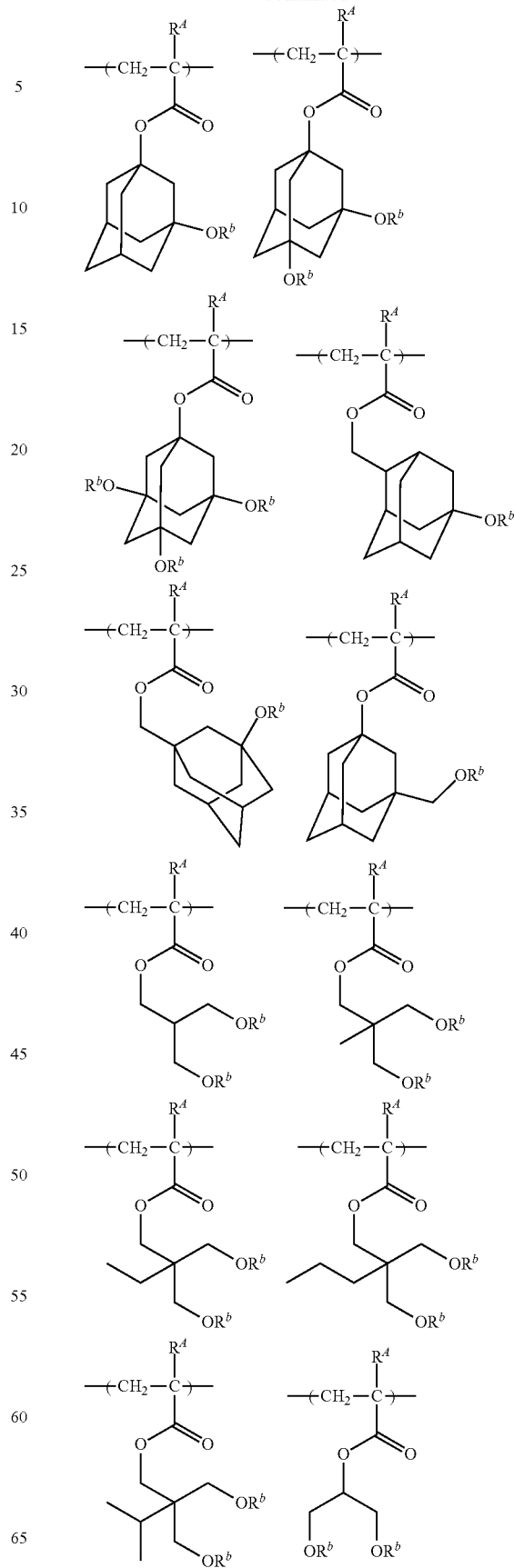

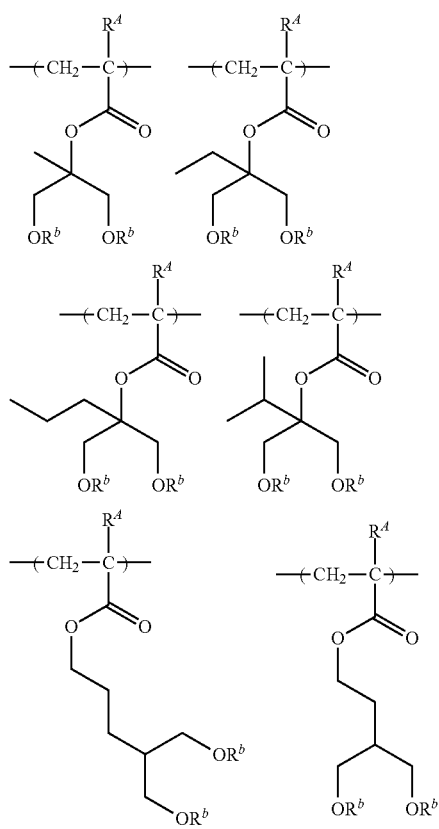

In formula (d1), the acid labile group $R^b$ is such that it may be deprotected to generate a hydroxyl group under the action of acid. Although the structure of the acid labile group $R^b$ is not particularly limited, it is preferably an acetal structure, ketal structure or alkoxycarbonyl group, examples of which are shown below.

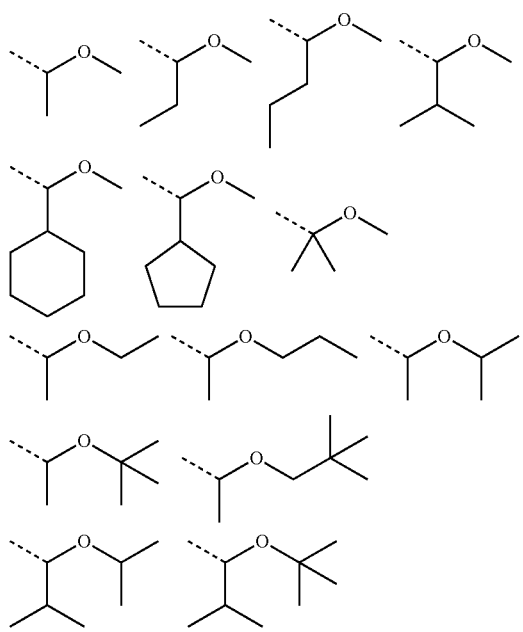

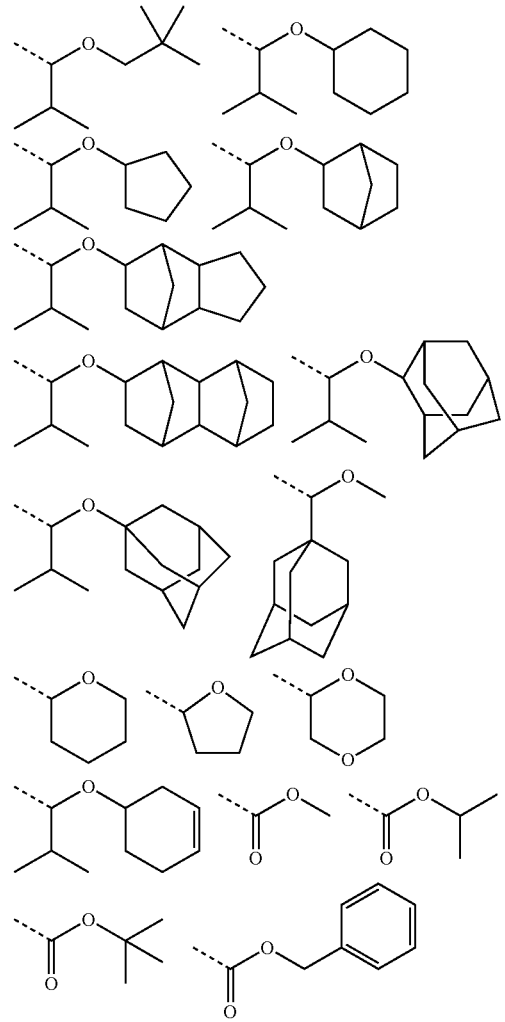

As the acid labile group $R^b$, alkoxymethyl groups having the formula (d2) are especially preferred.

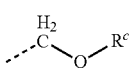

(d2)

Herein $R^c$ is a $C_1$-$C_{15}$ straight, branched or cyclic monovalent hydrocarbon group.

Examples of the acid labile group having formula (d2) are shown below, but not limited thereto.

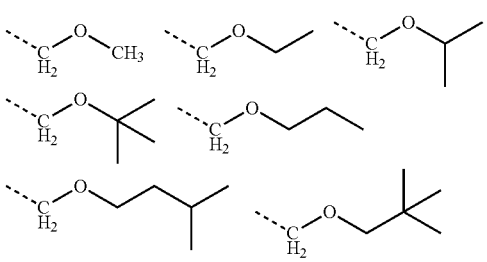

-continued
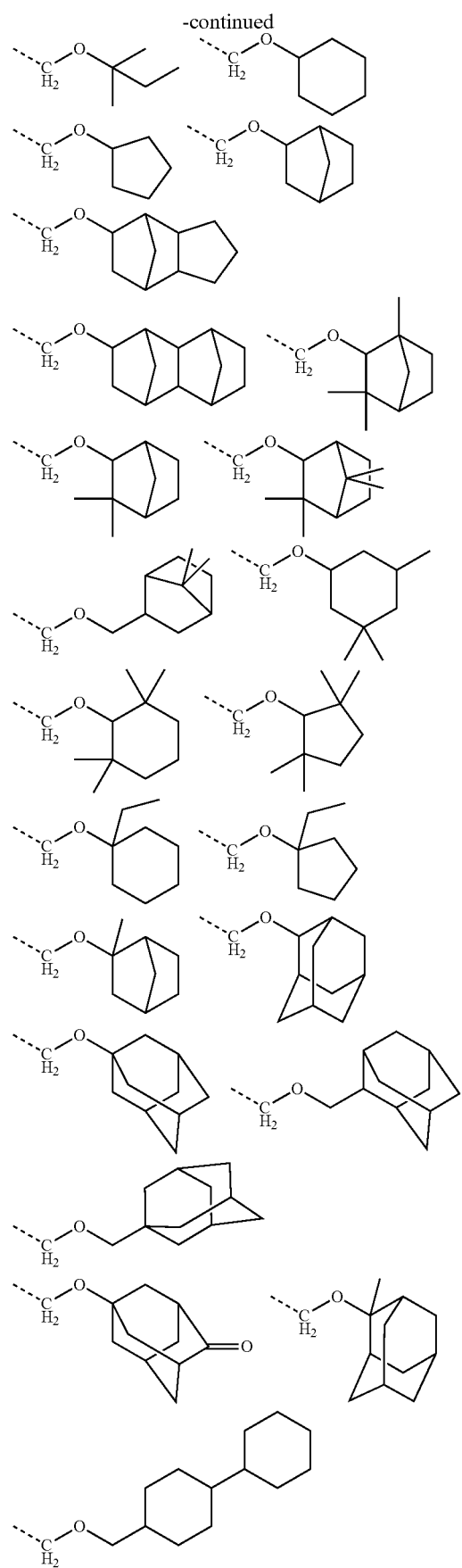
-continued
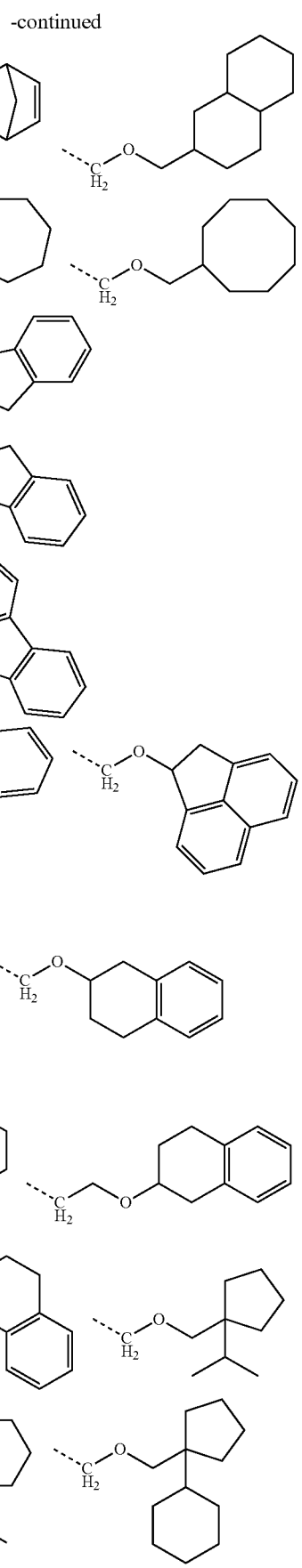

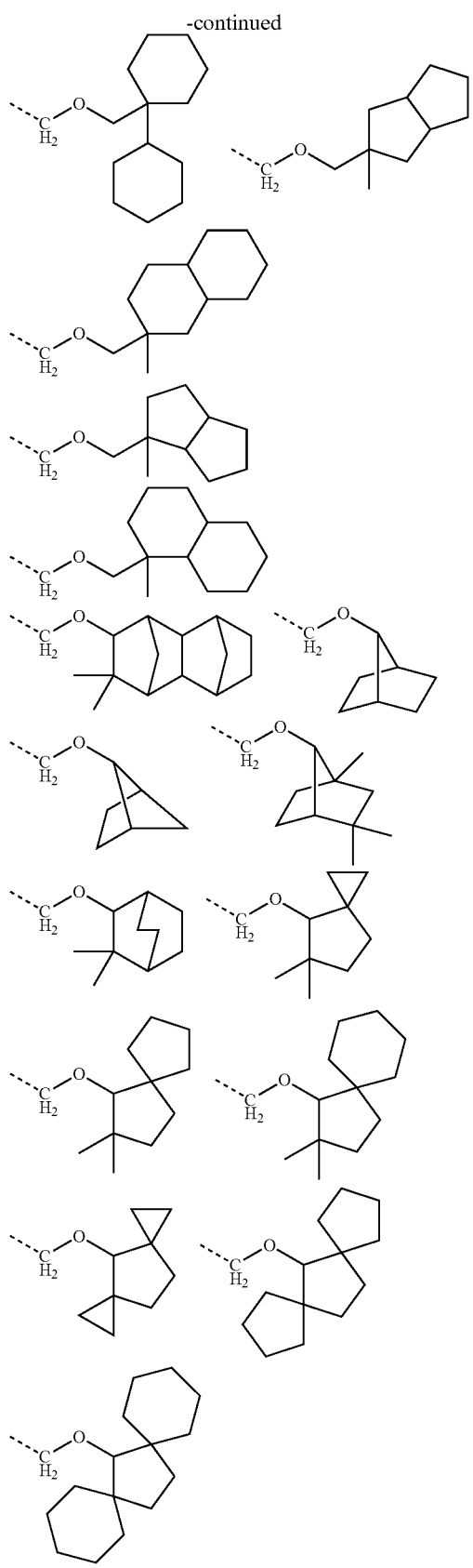

In addition to the foregoing units, the polymer may further comprise recurring units derived from, for example, substituted acrylic acid esters such as methyl methacrylate, methyl crotonate, dimethyl maleate and dimethyl itaconate, unsaturated carboxylic acids such as maleic acid, fumaric acid, and itaconic acid, cyclic olefins such as norbornene, norbornene derivatives, and tetracyclo[6.2.1.1$^{3,6}$.0$^{2,7}$]dodecene derivatives, unsaturated acid anhydrides such as itaconic anhydride, and other monomers.

The polymer should preferably have a weight average molecular weight (Mw) in the range of 1,000 to 500,000, and more preferably 3,000 to 100,000. A polymer with a Mw in the range has etching resistance and may not suffer a drop of resolution due to a failure to provide a difference in dissolution rate before and after exposure. The measurement of molecular weight may be performed by gel permeation chromatography (GPC) versus polystyrene standards using tetrahydrofuran (THF) solvent.

If a polymer has a wide molecular weight distribution or dispersity (Mw/Mu), which indicates the presence of lower and higher molecular weight polymer fractions, there is a possibility that foreign matter is left on the pattern or the pattern profile is degraded. The influences of molecular weight and dispersity become stronger as the pattern rule becomes finer. Therefore, the polymer should preferably have a narrow dispersity (Mw/Mn) of 1.0 to 2.0 in order to provide a resist composition suitable for micropatterning to a small feature size.

The polymer may be synthesized by any desired method, for example, by dissolving an unsaturated bond-containing monomer or monomers in an organic solvent, adding a radical initiator, and effecting heat polymerization. Suitable organic solvents used herein include toluene, benzene, tetrahydrofuran, diethyl ether, and dioxane. Examples of the polymerization initiator used herein include 2,2'-azobisisobutyronitrile (AIBN), 2,2'-azobis(2,4-dimethylvaleronitrile), dimethyl 2,2-azobis(2-methylpropionate), benzoyl peroxide, and lauroyl peroxide. Preferably the system is heated at 50 to 80° C. for polymerization to take place. The reaction time is 2 to 100 hours, preferably 5 to 20 hours. The acid labile group that has been incorporated in the monomer may be kept as such, or the polymer may be protected or partially protected therewith at the end of polymerization.

In the polymer, appropriate molar fractions (mol %) of the respective recurring units derived from the monomers are given below although the invention is not limited thereto. The polymer may comprise:

I) recurring units of at least one type having formula (a) in a fraction of 1 to 60 mol %, preferably 5 to 50 mol %, and more preferably 10 to 50 mol %, II) recurring units of at least one type having formula (b) in a fraction of 40 to 99 mol %, preferably 50 to 95 mol %, and more preferably 50 to 90 mol %, and optionally, III) recurring units of at least one type having formulae (c1) to (c3) in a fraction of 0 to 30 mol %, preferably 0 to 20 mol %, and more preferably 0 to 10 mol %, and optionally, IV) recurring units of at least one type derived from another monomer(s) in a fraction of 0 to 80 mol %, preferably 0 to 70 mol %, and more preferably 0 to 50 mol %.

The base resin (B) may also be a blend of the polymer defined above with another polymer, typically hydrogenated ROMP polymer as described in JP-A 2003-066612.

(C) Photoacid Generator

Component (C) is a photoacid generator which is not particularly limited as long as it generates an acid upon exposure to high-energy radiation. The preferred PAG has the formula (4).

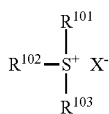
(4)

In formula (4), $R^{101}$, $R^{102}$ and $R^{103}$ are each independently a $C_1$-$C_{20}$ straight, branched or cyclic monovalent hydrocarbon group which may contain a heteroatom, any two of $R^{101}$, $R^{102}$ and $R^{103}$ may bond together to form a ring with the sulfur atom to which they are attached.

In formula (4), $X^-$ is an anion selected from the formulae (4A) to (4D):

(4A)

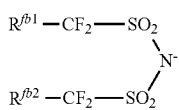
(4B)

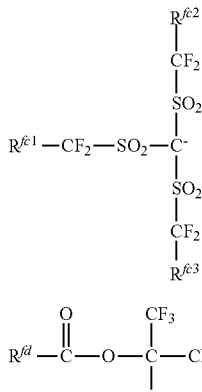
(4C)

(4D)

Herein $R^{fa}$ is fluorine or a $C_1$-$C_{40}$ straight, branched or cyclic monovalent hydrocarbon group which may contain a heteroatom.

Of the anions of formula (4A), a structure having formula (4A') is preferred.

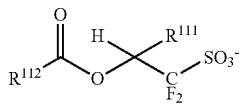
(4A')

In formula (4A'), $R^{111}$ is hydrogen or trifluoromethyl, preferably trifluoromethyl. $R^{112}$ is a $C_1$-$C_{38}$ straight, branched or cyclic monovalent hydrocarbon group which may contain a heteroatom. Suitable heteroatoms include oxygen, nitrogen, sulfur and halogen, with oxygen being preferred. Of the monovalent hydrocarbon groups, those of 6 to 30 carbon atoms are preferred because a high resolution is available in fine pattern formation. Suitable monovalent hydrocarbon groups include methyl, ethyl, propyl, isopropyl, butyl, isobutyl, s-butyl, t-butyl, pentyl, neopentyl, cyclopentyl, hexyl, cyclohexyl, 3-cyclohexenyl, heptyl, 2-ethylhexyl, nonyl, undecyl, tridecyl, pentadecyl, heptadecyl, 1-adamantyl, 2-adamantyl, 1-adamantylmethyl, norbornyl, norbornylmethyl, tricyclodecanyl, tetracyclododecanyl, tetracyclododecanylmethyl, dicyclohexylmethyl, icosanyl, allyl, benzyl, diphenylmethyl, tetrahydrofuryl, methoxymethyl, ethoxymethyl, methylthiomethyl, acetamidomethyl, trifluoroethyl, (2-methoxyethoxy)methyl, acetoxymethyl, 2-carboxy-1-cyclohexyl, 2-oxopropyl, 4-oxo-1-adamantyl, and 3-oxocyclohexyl. Also included are the foregoing groups in which at least one hydrogen is replaced by a substituent containing a heteroatom such as oxygen, sulfur, nitrogen or halogen, or in which a substituent containing a heteroatom such as oxygen, sulfur or nitrogen intervenes between carbon atoms, so that the group may contain a hydroxyl, cyano, carbonyl, ether bond, ester bond, sulfonic acid ester bond, carbonate bond, lactone ring, sultone ring, carboxylic acid anhydride or haloalkyl moiety.

With respect to the synthesis of the sulfonium salt having an anion of formula (4A'), reference is made to JP-A 2007-145797, JP-A 2008-106045, JP-A 2009-007327, and JP-A 2009-258695. Also useful are the sulfonium salts described in JP-A 2010-215608, JP-A 2012-041320, JP-A 2012-106986, and JP-A 2012-153644.

Examples of the sulfonium salt having an anion of formula (4A) are shown below, but not limited thereto.

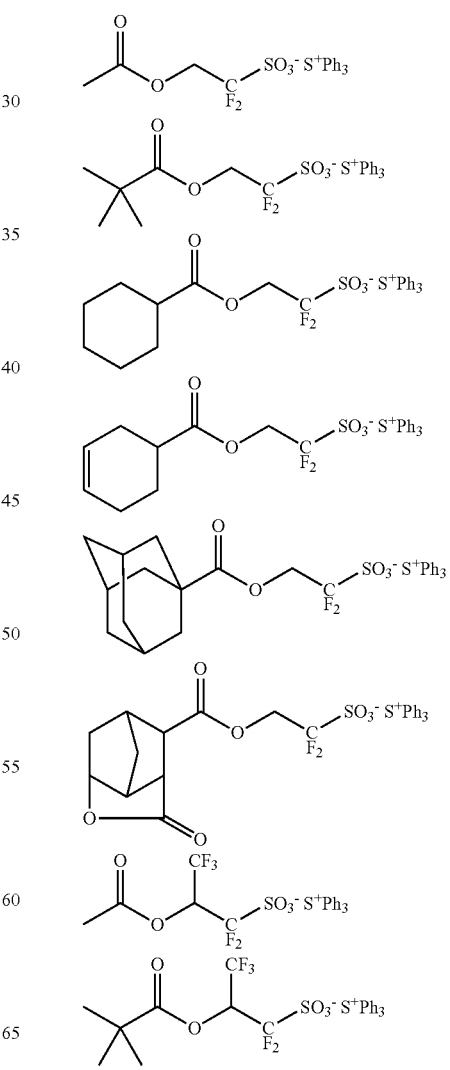

101
-continued
102
-continued
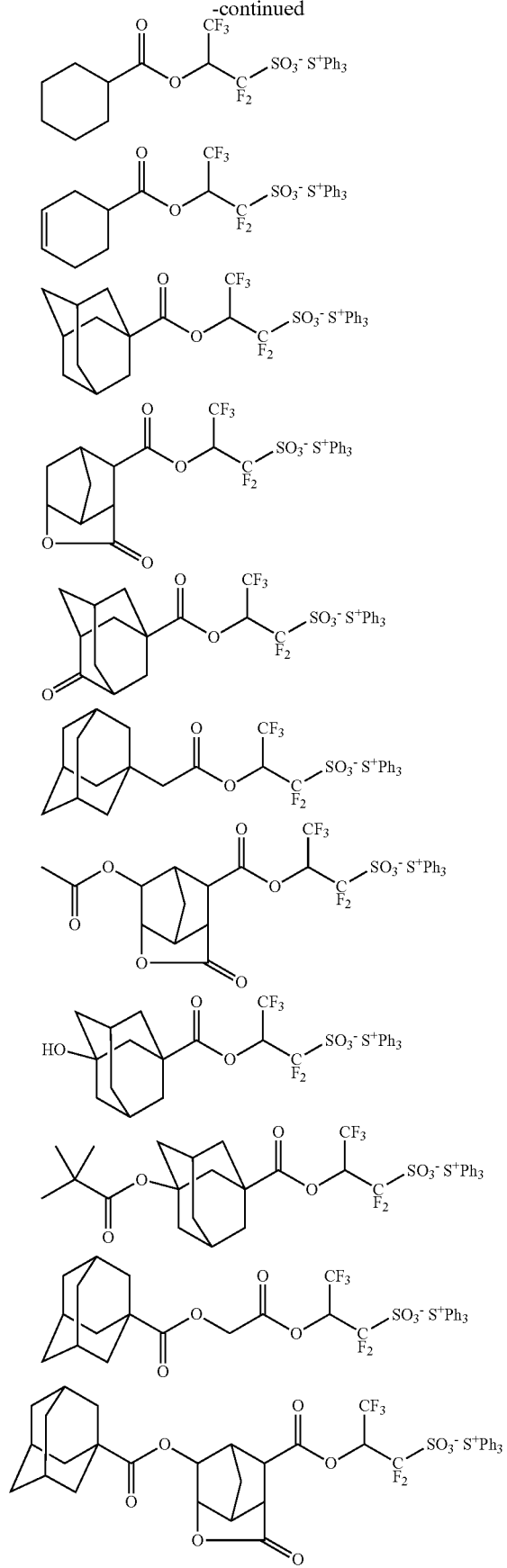
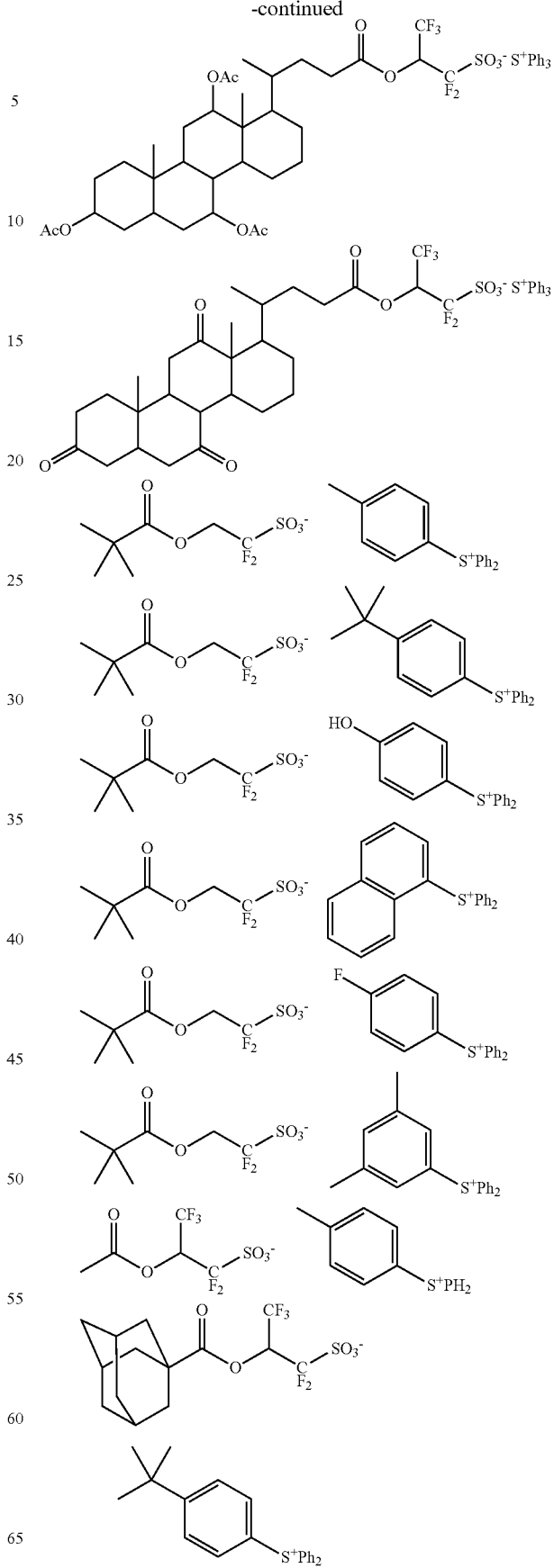

-continued
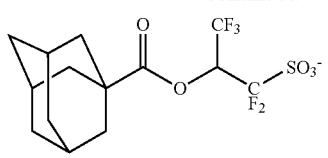
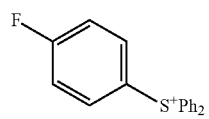
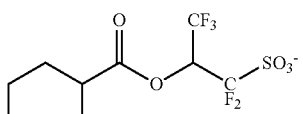
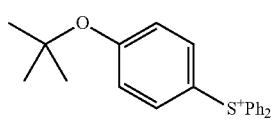
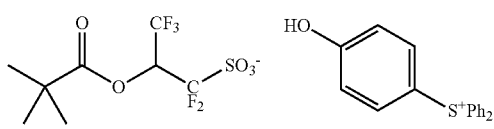
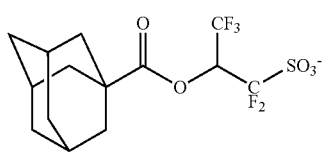
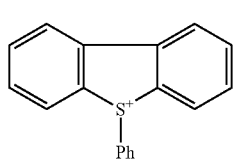
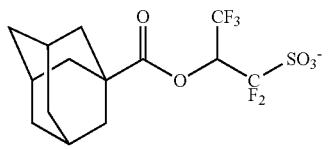
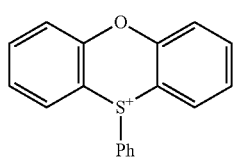
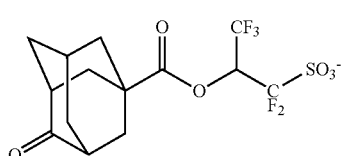
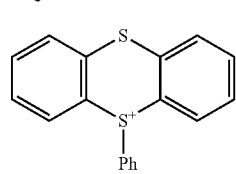
-continued
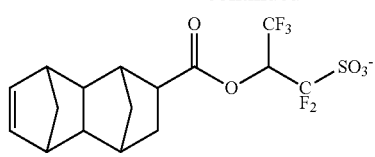
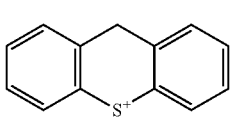
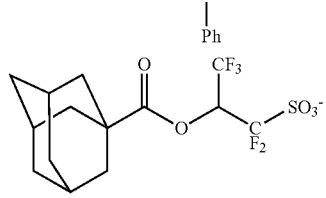
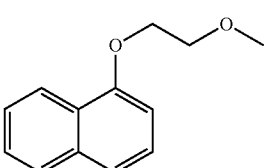
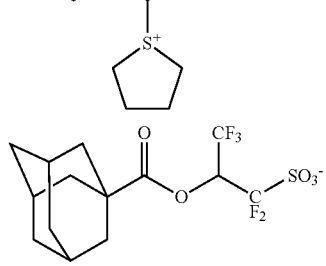
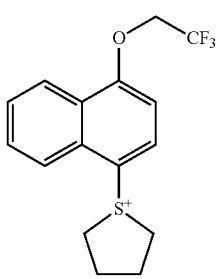
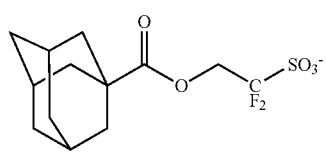
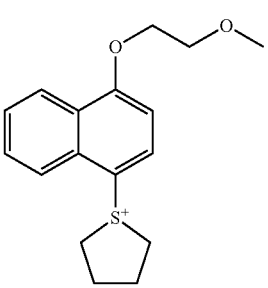

-continued

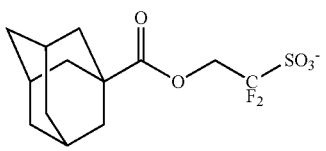

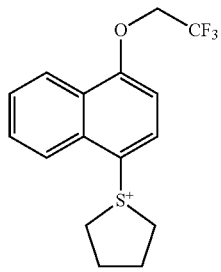

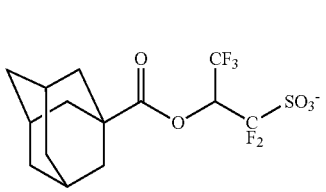

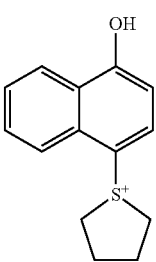

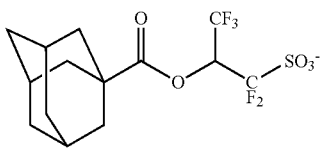

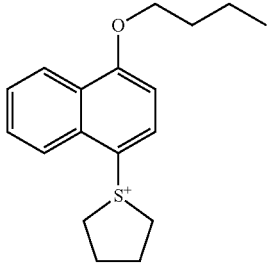

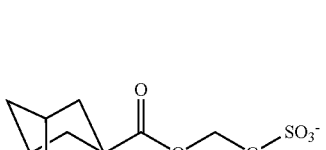

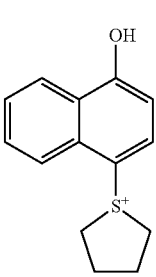

-continued

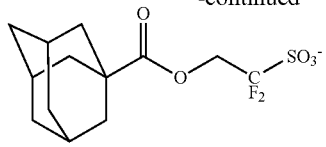

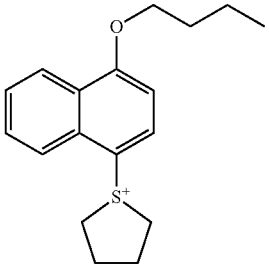

In formula (4B), $R^{fb1}$ and $R^{fb2}$ are each independently fluorine or a $C_1$-$C_{40}$ straight, branched or cyclic monovalent hydrocarbon group which may contain a heteroatom. Suitable monovalent hydrocarbon groups are as exemplified above for $R^{112}$. Preferably $R^{fb1}$ and $R^{fb2}$ each are fluorine or a $C_1$-$C_4$ straight fluorinated alkyl group. A pair of $R^{fb1}$ and $R^{fb2}$ may bond together to form a ring with the linkage (—$CF_2$—$SO_2$—$N^-$—$SO_2$—$CF_2$—) to which they are attached, and preferably the pair is a fluorinated ethylene or fluorinated propylene group forming a ring structure.

In formula (4C), $R^{fc1}$, $R^{fc2}$ and $R^{fc3}$ are each independently fluorine or a $C_1$-$C_{40}$ straight, branched or cyclic monovalent hydrocarbon group which may contain a heteroatom. Suitable monovalent hydrocarbon groups are as exemplified above for $R^{112}$. Preferably $R^{fc1}$, $R^{fc2}$ and $R^{fc3}$ each are fluorine or a $C_1$-$C_4$ straight fluorinated alkyl group. A pair of $R^{fc1}$ and $R^{fc2}$ may bond together to form a ring with the the linkage (—$CF_2$—$SO_2$—$C^-$—$SO_2$—$CF_2$—) to which they are attached, and preferably the pair is a fluorinated ethylene or fluorinated propylene group forming a ring structure.

In formula (4D), $R^{fd}$ is a $C_1$-$C_{40}$ straight, branched or cyclic monovalent hydrocarbon group which may contain a heteroatom. Suitable monovalent hydrocarbon groups are as exemplified above for $R^{112}$.

With respect to the synthesis of the sulfonium salt having an anion of formula (4D), reference is made to JP-A 2010-215608 and JP-A 2014-133723.

Examples of the sulfonium salt having an anion of formula (4D) are shown below, but not limited thereto.

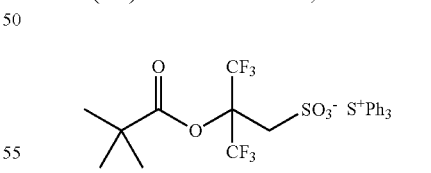

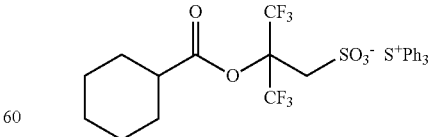

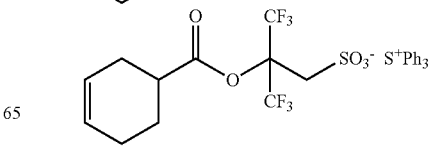

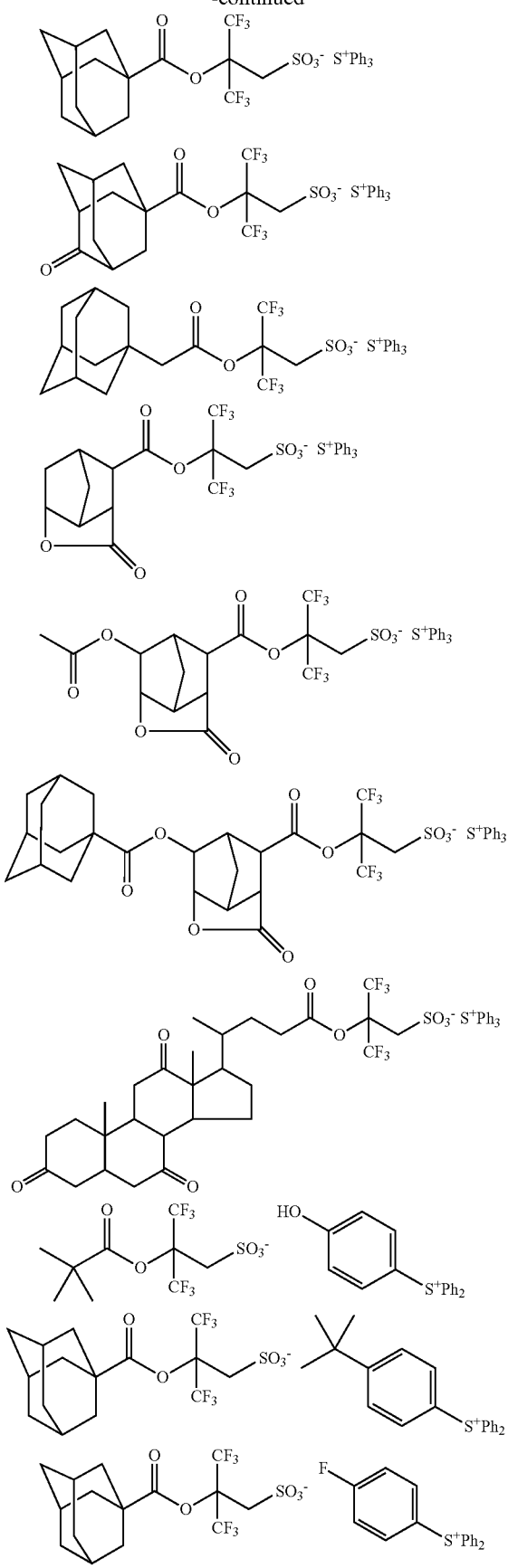

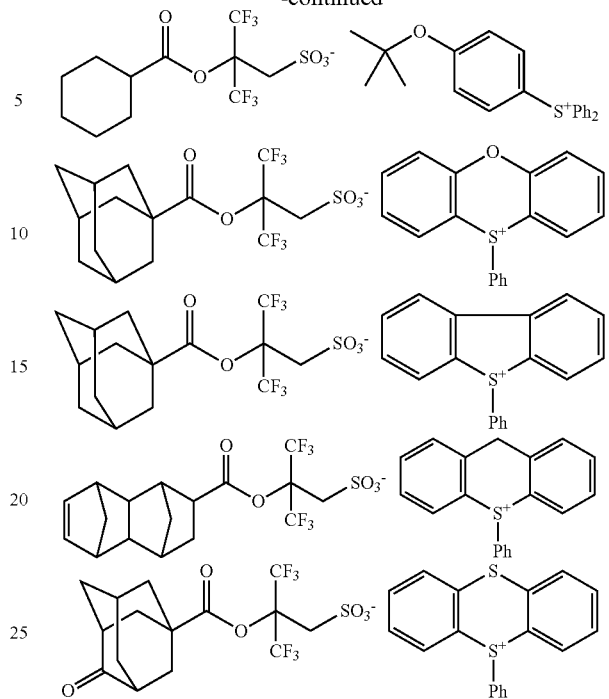

The compound having the anion of formula (4D) has a sufficient acid strength to cleave acid labile groups in the resist polymer because it is free of fluorine at α-position of sulfo group, but has two trifluoromethyl groups at β-position. Thus the compound is a useful PAG.

As the PAG (C), those compounds having the formula (5) are also preferred.

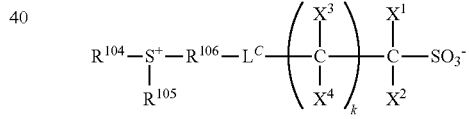

(5)

In formula (5), $R^{104}$ and $R^{105}$ are each independently a $C_1$-$C_{30}$ straight, branched or cyclic monovalent hydrocarbon group which may contain a heteroatom. $R^{106}$ is a $C_1$-$C_{30}$ straight, branched or cyclic divalent hydrocarbon group which may contain a heteroatom. Any two of $R^{104}$, $R^{105}$ and $R^{106}$ may bond together to form a ring with the sulfur atom to which they are attached. $L^C$ is a single bond, ether bond or a $C_1$-$C_{20}$ straight, branched or cyclic divalent hydrocarbon group which may contain a heteroatom. $X^1$, $X^2$, $X^3$ and $X^4$ are each independently hydrogen, fluorine or trifluoromethyl, with the proviso that at least one of $X^1$, $X^2$, $X^3$ and $X^4$ is a substituent group other than hydrogen, k is an integer of 1 to 3.

Suitable monovalent hydrocarbon groups include methyl, ethyl, propyl, isopropyl, n-butyl, s-butyl, t-butyl, t-pentyl, n-pentyl, n-hexyl, n-octyl, n-nonyl, n-decyl, cyclopentyl, cyclohexyl, 2-ethylhexyl, cyclopentylmethyl, cyclopentylethyl, cyclopentylbutyl, cyclohexylmethyl, cyclohexylethyl, cyclohexylbutyl, norbornyl, oxanorbornyl, tricyclo[5.2.1.$0^{2,6}$]decanyl, adamantyl, phenyl, naphthyl, and anthracenyl. Also included are the foregoing groups in which at least one hydrogen is replaced by a substituent containing a heteroatom such as oxygen, sulfur, nitrogen or halogen, or in which a substituent containing a heteroatom such as oxygen, sulfur or nitrogen intervenes between carbon atoms, so that the group may contain a hydroxyl, cyano, carbonyl, ether bond, ester bond, sulfonic acid ester bond, carbonate bond, lactone ring, sultone ring, carboxylic acid anhydride or haloalkyl moiety.

Suitable divalent hydrocarbon groups include linear alkane diyl groups such as methylene, ethylene, propane-1,3-diyl, butane-1,4-diyl, pentane-1,5-diyl, hexane-1,6-diyl, heptane-1,7-diyl, octane-1,8-diyl, nonane-1,9-diyl, decane-1,10-diyl, undecane-1,11-diyl, dodecane-1,12-diyl, tridecane-1,13-diyl, tetradecane-1,14-diyl, pentadecane-1,15-diyl, hexadecane-1,16-diyl, heptadecane-1,17-diyl; saturated cyclic divalent hydrocarbon groups such as cyclopentanediyl, cyclohexanediyl, norbornanediyl, and adamantanediyl; and unsaturated cyclic divalent hydrocarbon groups such as phenylene and naphthylene. Also included are the foregoing groups in which at least one hydrogen atom is replaced by an alkyl group such as methyl, ethyl, propyl, n-butyl or t-butyl, or in which at least one hydrogen atom is replaced by a substituent containing a heteroatom such as oxygen, sulfur, nitrogen or halogen, or in which a substituent containing a heteroatom such as oxygen, sulfur or nitrogen intervenes between carbon atoms, so that the group may contain a hydroxyl, cyano, carbonyl, ether bond, ester bond, sulfonic acid ester bond, carbonate bond, lactone ring, sultone ring, carboxylic acid anhydride or haloalkyl moiety. Suitable heteroatoms include oxygen, nitrogen, sulfur and halogen, with oxygen being preferred.

Of the PAGs having formula (5), those having formula (5') are preferred.

(5')

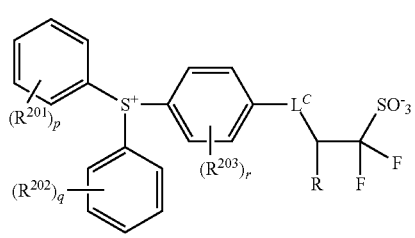

In formula (5'), $L^C$ is as defined above. R is hydrogen or trifluoromethyl, preferably trifluoromethyl. $R^{201}$, $R^{202}$ and $R^{203}$ are each independently hydrogen or a $C_1$-$C_{20}$ straight, branched or cyclic monovalent hydrocarbon group which may contain a heteroatom. Suitable monovalent hydrocarbon groups are as exemplified above for $R^{112}$. The subscripts p and q each are an integer of 0 to 5, and r is an integer of 0 to 4.

Examples of the PAG having formula (5) are shown below, but not limited thereto. Herein R is as defined above.

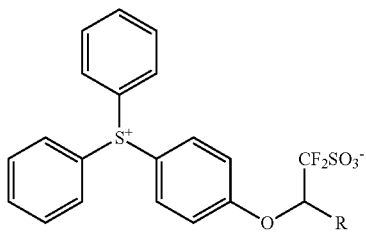

-continued

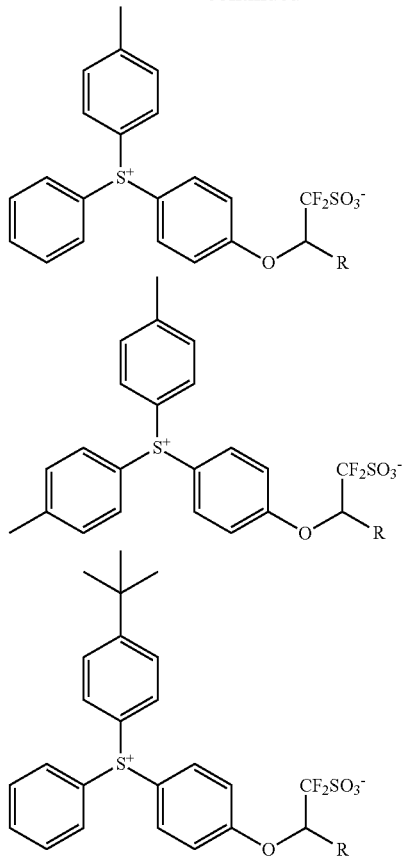

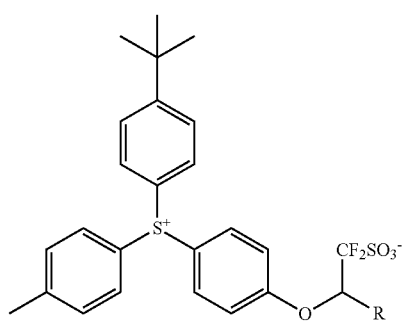

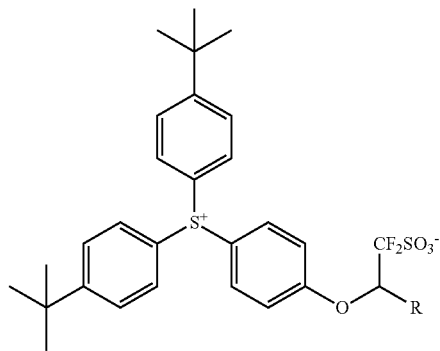

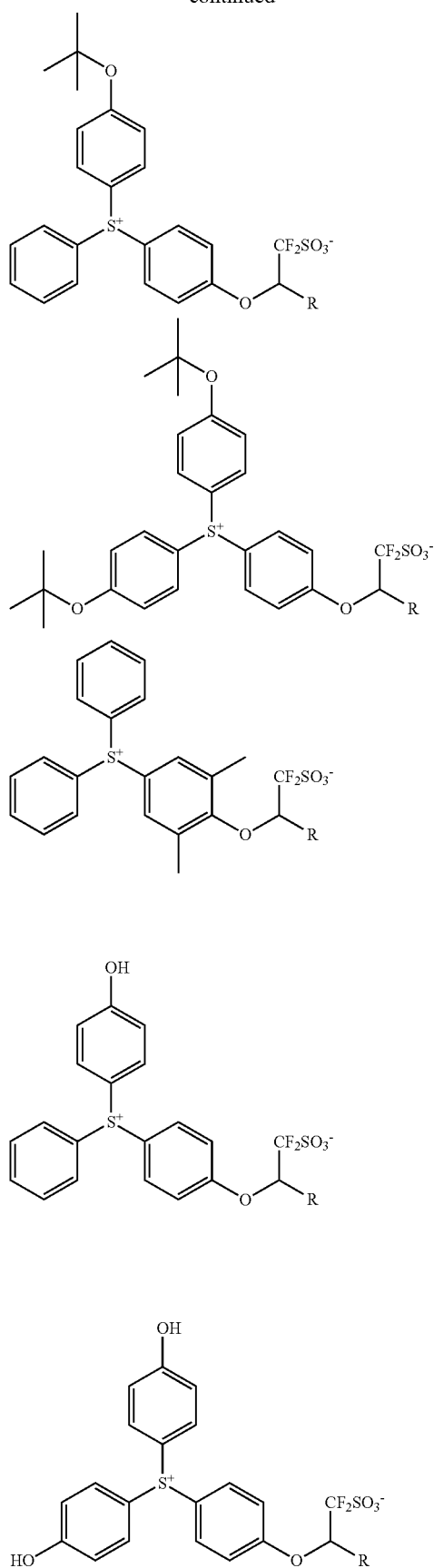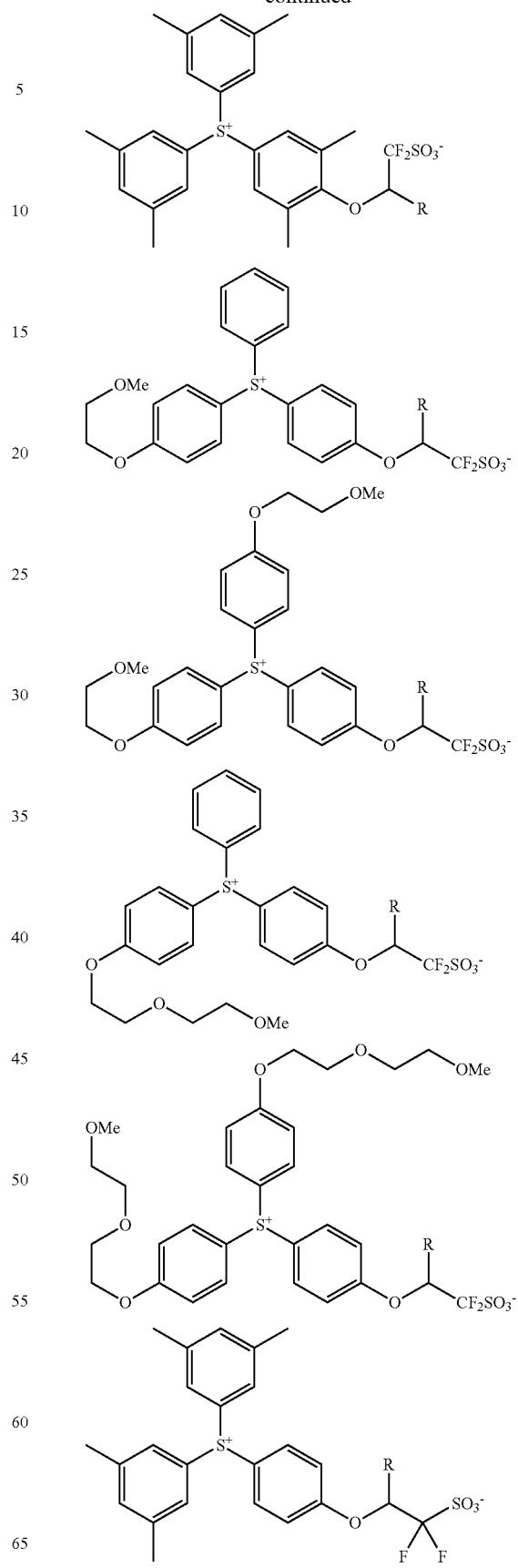

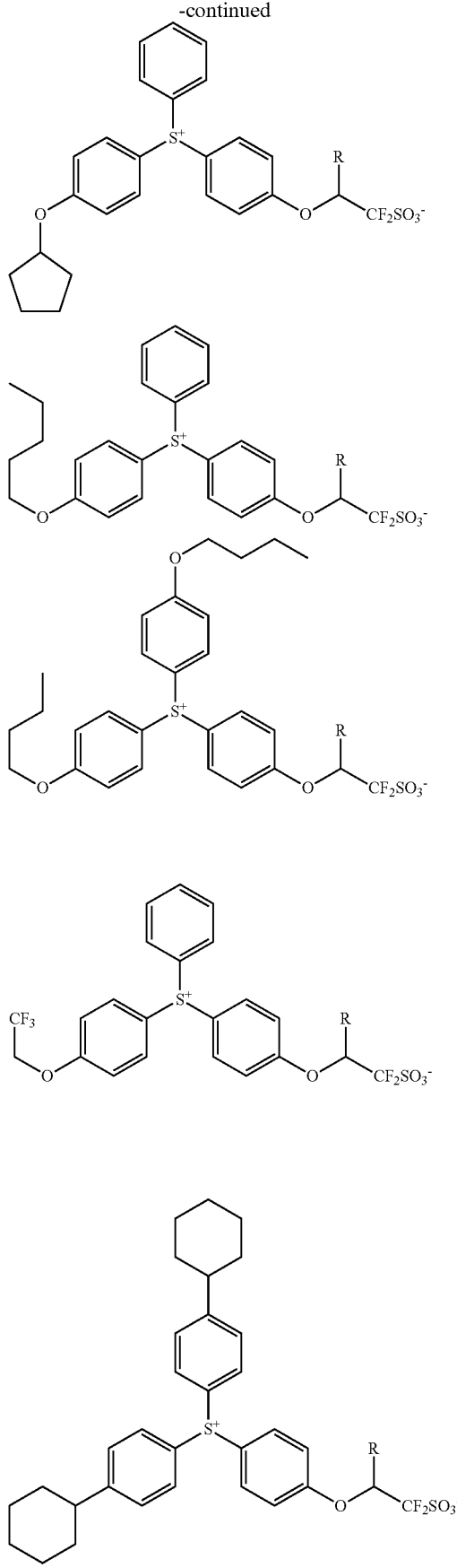
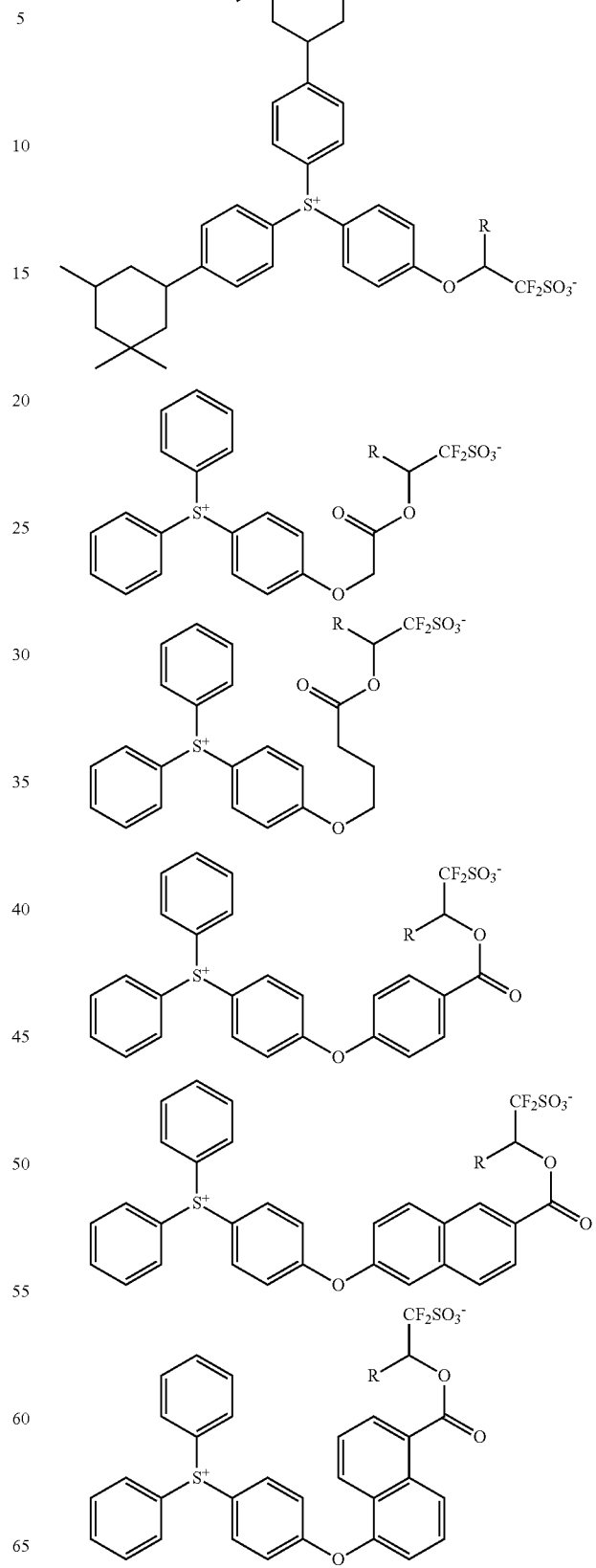

-continued

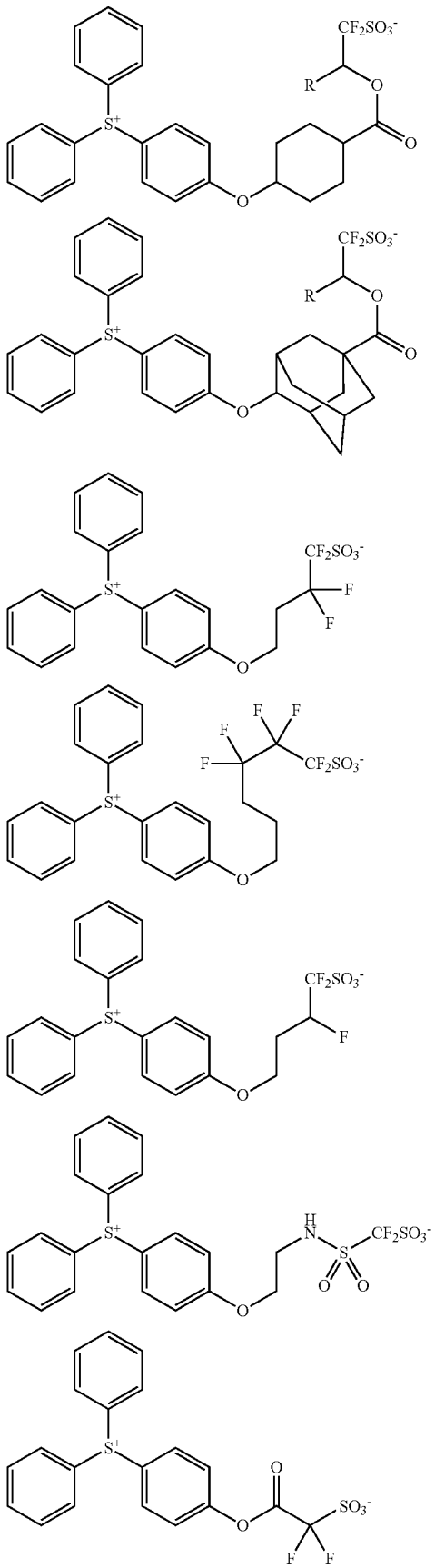

-continued

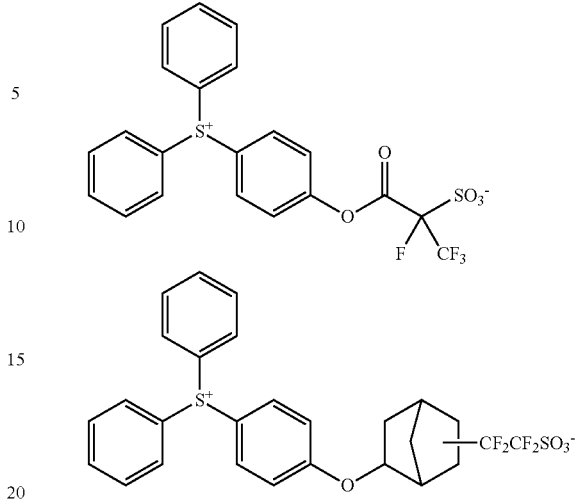

Of the foregoing PAGs, those compounds having an anion of formula (4A') or (4D) are especially preferred because of reduced acid diffusion and high solubility in resist solvent, and those compounds having an anion of formula (5') are especially preferred because of minimized acid diffusion.

An amount of the PAG (C) added is preferably 0.1 to 40 parts, and more preferably 0.5 to 20 parts by weight per 100 parts by weight of the base resin (B). An amount in the range ensures good resolution and leaves no foreign particles after resist development or during separation.

(D) Organic Solvent

Component (D) is an organic solvent, which is not particularly limited as long as the components are soluble therein. Examples of the organic solvent are described in JP-A 2008-111103, paragraphs [0144] to [0145] (U.S. Pat. No. 7,537,880). Specifically, exemplary solvents include ketones such as cyclohexanone and methyl-2-n-pentyl ketone; alcohols such as 3-methoxybutanol, 3-methyl-3-methoxybutanol, 1-methoxy-2-propanol, and 1-ethoxy-2-propanol; ethers such as propylene glycol monomethyl ether, ethylene glycol monomethyl ether, propylene glycol monoethyl ether, ethylene glycol monoethyl ether, propylene glycol dimethyl ether, and diethylene glycol dimethyl ether; esters such as propylene glycol monomethyl ether acetate (PGMEA), propylene glycol monoethyl ether acetate, ethyl lactate, ethyl pyruvate, butyl acetate, methyl 3-methoxypropionate, ethyl 3-ethoxypropionate, t-butyl acetate, t-butyl propionate, and propylene glycol mono-t-butyl ether acetate; and lactones such as γ-butyrolactone, and mixtures thereof. Where an acid labile group of acetal form is used, a high-boiling alcohol solvent such as diethylene glycol, propylene glycol, glycerol, 1,4-butanediol or 1,3-butanediol may be added for accelerating deprotection reaction of acetal. Of the above organic solvents, it is recommended to use 1-ethoxy-2-propanol, PGMEA, cyclohexanone, γ-butyrolactone, and mixtures thereof because the PAG (C) is most soluble therein.

An appropriate amount of the organic solvent (D) used is 200 to 5,000 parts, more preferably 400 to 3,000 parts by weight per 100 parts by weight of the base resin (B).

(E) Nitrogen-Containing Compound

While the acid diffusion controlling agent (A) is essential in the resist composition, a nitrogen-containing compound may also be added as the acid diffusion controlling agent. Suitable nitrogen-containing compounds include primary, secondary and tertiary amine compounds, specifically amine compounds having a hydroxyl group, ether bond, ester bond, lactone ring, cyano group or sulfonate bond, as described in JP-A 2008-111103, paragraphs [0146] to [0164] (U.S. Pat. No. 7,537,880). Also useful are compounds whose primary or secondary amine is protected with a carbamate group as described in JP 3790649.

Also, a sulfonium salt of sulfonic acid having a nitrogen-containing substituent may be used as component (E). This compound is a so-called photo-degradable base which functions as quencher in the unexposed region, but loses quencher ability through neutralization with the acid generated by itself, in the exposed region. The use of photo-degradable base is effective for enhancing the contrast between exposed and unexposed regions. With respect to the photo-degradable base, reference may be made to JP-A 2009-109595 and JP-A 2012-046501, for example.

The nitrogen-containing compounds may be used alone or in admixture of two or more. The nitrogen-containing compound (E) is preferably used in an amount of 0.001 to 12 parts, more preferably 0.01 to 8 parts by weight per 100 parts by weight of the base resin (B).

(F) Surfactant which is Insoluble or Substantially Insoluble in Water and Soluble in Alkaline Developer, and/or Surfactant which is Insoluble or Substantially Insoluble in Water and Alkaline Developer (Hydrophobic Resin)

To the resist composition, a surfactant which is insoluble or substantially insoluble in water and soluble in alkaline developer, and/or a surfactant which is insoluble or substantially insoluble in water and alkaline developer (hydrophobic resin) may be added as component (F). Reference should be made to those compounds described in JP-A 2010-215608 and JP-A 2011-16746.

While many examples of the surfactant which is insoluble or substantially insoluble in water and alkaline developer are described in these patent documents, preferred examples are FC-4430, Surflon S-381, Surfynol E1004, KH-20 and KH-30, which may be used alone or in admixture. Partially fluorinated oxetane ring-opened polymers having the structural formula (surf-1) are also useful.

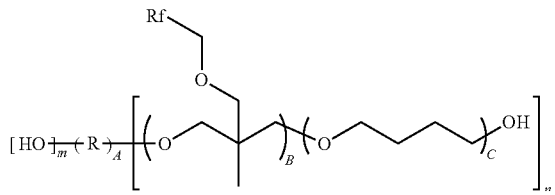

(surf-1)

It is provided herein that R, Rf, A, B, C, m, and n are applied to only formula (surf-1), independent of their descriptions other than for the surfactant. R is a di- to tetra-valent $C_2$-$C_5$ aliphatic group. Exemplary divalent groups include ethylene, 1,4-butylene, 1,2-propylene, 2,2-dimethyl-1,3-propylene and 1,5-pentylene. Exemplary tri- and tetra-valent groups are shown below.

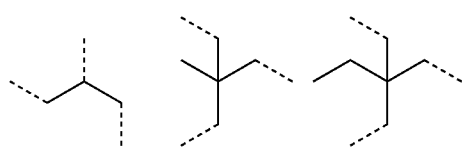

-continued

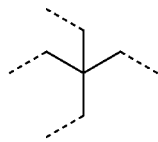

Herein the broken line denotes a valence bond. These formulae are partial structures derived from glycerol, trimethylol ethane, trimethylol propane, and pentaerythritol, respectively. Of these, 1,4-butylene and 2,2-dimethyl-1,3-propylene are preferably used.

Rf is trifluoromethyl or pentafluoroethyl, and preferably trifluoromethyl. The letter m is an integer of 0 to 3, n is an integer of 1 to 4, and the sum of m and n, which represents the valence of R, is an integer of 2 to 4. A is equal to 1, B is an integer of 2 to 25, and C is an integer of 0 to 10. Preferably, B is an integer of 4 to 20, and C is 0 or 1. Note that the above structural formula does not prescribe the arrangement of respective constituent units while they may be arranged either blockwise or randomly. For the preparation of surfactants in the form of partially fluorinated oxetane ring-opened polymers, reference should be made to U.S. Pat. No. 5,650,483, for example.

The surfactant which is insoluble or substantially insoluble in water and soluble in alkaline developer is useful when ArF immersion lithography is applied to the resist composition in the absence of a resist protective film. In this embodiment, the surfactant has a propensity to segregate on the resist surface after spin coating for achieving a function of minimizing water penetration or leaching. The surfactant is also effective for preventing water-soluble components from being leached out of the resist film for minimizing any damage to the exposure tool. The surfactant becomes solubilized during alkaline development following exposure and PEB, and thus forms few or no foreign particles which become defects. The preferred surfactant is a polymeric surfactant which is insoluble or substantially insoluble in water, but soluble in alkaline developer, also referred to as "hydrophobic resin" in this sense, and especially which is water repellent and enhances water slippage.

Suitable polymeric surfactants are shown below.

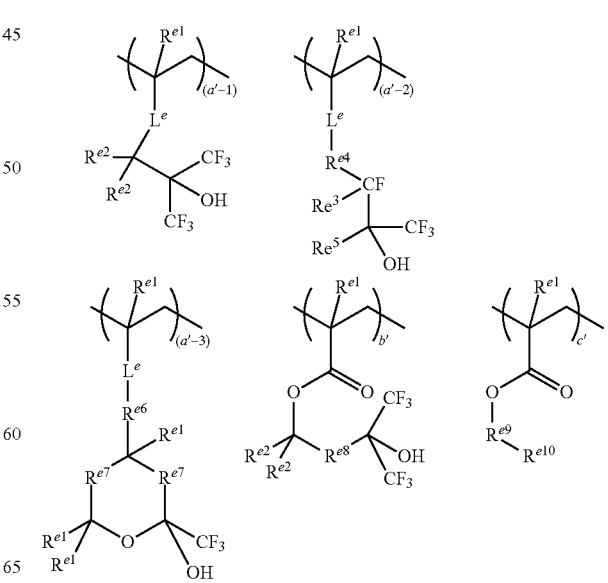

Herein $R^{e1}$ is each independently hydrogen, fluorine, methyl or trifluoromethyl. Re is each independently hydrogen or a $C_1$-$C_{20}$ straight, branched or cyclic alkyl or fluoroalkyl group, or two $R^{e2}$ in a common monomer may bond together to form a ring with the carbon atom to which they are attached, and in this event, they together represent a $C_2$-$C_{20}$ straight, branched or cyclic alkylene or fluoroalkylene group. $R^{e3}$ is fluorine or hydrogen, or $R^{e3}$ may bond with $R^{e4}$ to form a non-aromatic ring of 3 to 10 carbon atoms in total with the carbon atom to which they are attached. $R^{e4}$ is a $C_1$-$C_6$ straight, branched or cyclic alkylene group in which at least one hydrogen atom may be substituted by a fluorine atom. $R^{e5}$ is a $C_1$-$C_{10}$ straight or branched alkyl group in which at least one hydrogen atom is substituted by a fluorine atom. Alternatively, $R^{e4}$ and $R^{e5}$ may bond together to form a non-aromatic ring with the carbon atoms to which they are attached. In this event, $R_{e4}$, $R^{e5}$ and the carbon atoms to which they are attached together represent a trivalent organic group of 3 to 12 carbon atoms in total. $R^{e6}$ is a single bond or a $C_1$-$C_4$ alkylene.

$R^{e7}$ is each independently a single bond, —O—, or —$CR^{e1}R^{e1}$—. $R^{e8}$ is a $C_1$-$C_4$ straight or $C_3$-$C_4$ branched alkylene group, or may bond with $R^2$ within a common monomer to form a $C_3$-$C_6$ non-aromatic ring with the carbon atom to which they are attached.

$R^{e9}$ is 1,2-ethylene, 1,3-propylene, or 1,4-butylene. $R^{e10}$ is a $C_3$-$C_6$ linear perfluoroalkyl group, typically 3H-perfluoropropyl, 4H-perfluorobutyl, 5H-perfluoropentyl or 6H-perfluorohexyl. $L^e$ is each independently —C(=O)—O—, —O—, or —C(=O)—$R^{e11}$—C(=O)—O— wherein $R^{e11}$ is a $C_1$-$C_{10}$ straight, branched or cyclic alkylene group. The subscripts are in the range: $0 \leq (a'-1) \leq 1$, $0 \leq (a'-2) \leq 1$, $0 \leq (a'-3) \leq 1$, $0 < (a'-1)+(a'-2)+(a'-3) \leq 1$, $0 \leq b' \leq 1$, $0 \leq c' \leq 1$, and $0 < (a'-1)+(a'-2)+(a'-3)+b'+c' \leq 1$.

Exemplary non-limiting units are shown below. $R^{e1}$ is as defined above.

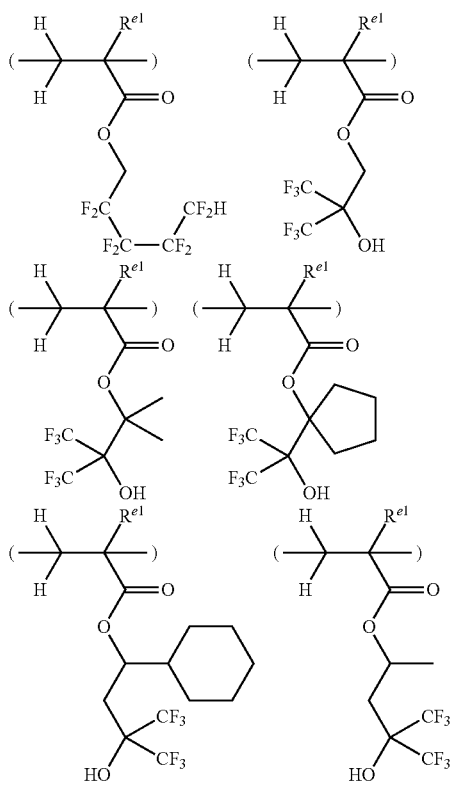

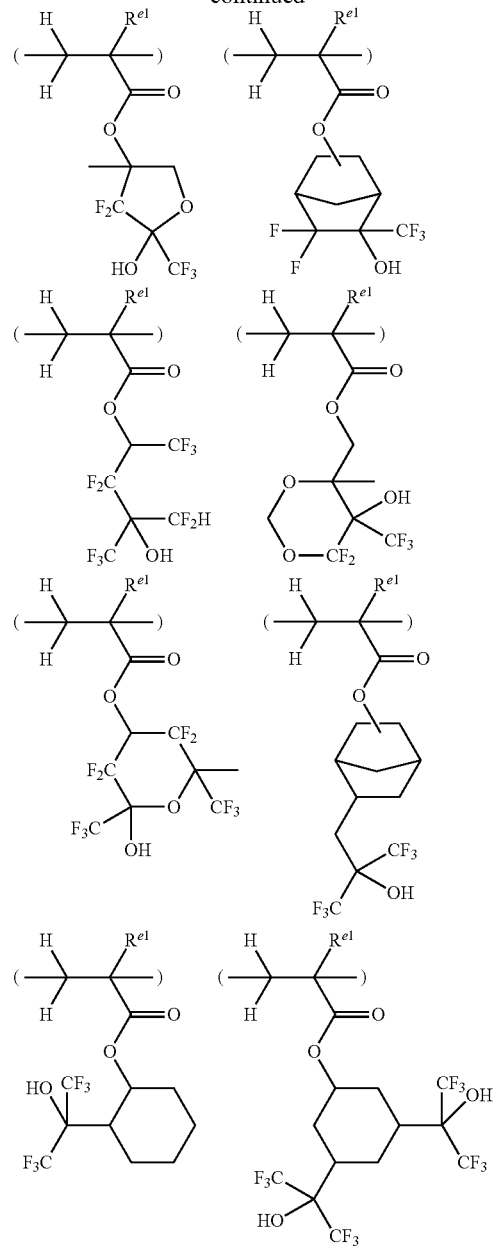

For the surfactant which is insoluble or substantially insoluble in water and soluble in alkaline developer, reference may be made to JP-A 2008-122932, 2010-134012, 2010-107695, 2009-276363, 2009-192784, 2009-191151, 2009-098638, 2011-250105, and 2011-042789.

The polymeric surfactant preferably has a Mw of 1,000 to 50,000, more preferably 2,000 to 20,000 as measured by GPC versus polystyrene standards. A surfactant with a Mw in the range is effective for surface modification and causes least development defects.

Component (F) is preferably formulated in an amount of 0 to 20 parts by weight per 100 parts by weight of the base resin (B). When added, the amount of component (F) is preferably at least 0.001 part, more preferably at least 0.01 part and also preferably up to 15 parts, more preferably up to 10 parts by weight.

(G) Other Components

To the resist composition, there may be added a compound which is decomposed with an acid to generate another acid (i.e., acid amplifier compound), an organic acid derivative, a fluorinated alcohol, and a compound having a Mw of up to 3,000 which changes its solubility in alkaline developer under the action of an acid (i.e., dissolution inhibitor). For the acid amplifier compound, reference should be made to JP-A 2009-269953 and 2010-215608. In the resist composition, an appropriate amount of the acid amplifier compound is 0 to 5 parts, and more preferably 0 to 3 parts by weight per 100 parts by weight of the base resin (B). Excessive amounts of the acid amplifier compound make diffusion control difficult, leading to degradation of resolution and pattern profile. For the organic acid derivative, fluorinated alcohol, and dissolution inhibitor, reference may be made to JP-A 2009-269953 and 2010-215608.

Process

A further embodiment of the invention is a pattern forming process using the resist composition defined above. A pattern may be formed from the resist composition using any well-known lithography process. The preferred process includes at least the steps of forming a resist film on a substrate, exposing it to high-energy radiation, and developing it in a developer.

Specifically, the resist composition is applied onto a substrate for integrated circuit fabrication (e.g., Si, $SiO_2$, SiN, SiON, TiN, WSi, BPSG, SOG or organic antireflective coating) or substrate for mask circuit fabrication (e.g., Cr, CrO, CrON or MoSi) by a suitable coating technique such as spin coating. The coating is prebaked on a hot plate at a temperature of 60 to 150° C. for 1 to 10 minutes, preferably 80 to 140° C. for 1 to 5 minutes, to form a resist film of 0.05 to 2 μm thick. Through a mask with the desired pattern placed over the resist film, the resist film is exposed to high-energy radiation, typically KrF excimer laser, ArF excimer laser or EUV radiation in a dose of 1 to 200 $mJ/cm^2$, and preferably 10 to 100 $mJ/cm^2$. The exposure may be performed by conventional lithography whereas the immersion lithography of holding a liquid between the projection lens and the resist film may be employed if desired. In this case, a protective film which is insoluble in water may be applied on the resist film. The resist film is then baked (PEB) on a hot plate at 60 to 150° C. for 1 to 5 minutes, preferably 80 to 140° C. for 1 to 3 minutes. Thereafter the resist film is developed with a developer in the form of an aqueous base solution, for example, 0.1 to 5 wt %, preferably 2 to 3 wt % aqueous solution of tetramethylammonium hydroxide (TMAH) for 0.1 to 3 minutes, preferably 0.5 to 2 minutes by conventional techniques such as dip, puddle and spray techniques. In this way, a desired resist pattern is formed on the substrate.

The water-insoluble protective film which is used in the immersion lithography is to prevent any components from being leached out of the resist film and to improve water slippage at the film surface and is generally divided into two types. The first type is an organic solvent-strippable protective film which must be stripped, prior to alkaline development, with an organic solvent in which the resist film is not dissolvable. The second type is an alkali-soluble protective film which is soluble in an alkaline developer so that it can be removed simultaneously with the removal of solubilized regions of the resist film. The protective film of the second type is preferably of a material comprising a polymer having a 1,1,1,3,3,3-hexafluoro-2-propanol residue (which is insoluble in water and soluble in an alkaline developer) as a base in an alcohol solvent of at least 4 carbon atoms, an ether solvent of 8 to 12 carbon atoms or a mixture thereof. Alternatively, the aforementioned surfactant which is insoluble in water and soluble in an alkaline developer may be dissolved in an alcohol solvent of at least 4 carbon atoms, an ether solvent of 8 to 12 carbon atoms or a mixture thereof to form a material from which the protective film of the second type is formed.

Any desired step may be added to the pattern forming process. For example, after a photoresist film is formed, a step of rinsing with pure water (post-soaking) may be introduced to extract the acid generator or the like from the film surface or wash away particles. After exposure, a step of rinsing (post-soaking) may be introduced to remove any water remaining on the film after exposure.

Also a double patterning process may be used for pattern formation. The double patterning process includes a trench process of processing an underlay to a 1:3 trench pattern by a first step of exposure and etching, shifting the position, and forming a 1:3 trench pattern by a second step of exposure for forming a 1:1 pattern; and a line process of processing a first underlay to a 1:3 isolated left pattern by a first step of exposure and etching, shifting the position, processing a second underlay formed below the first underlay by a second step of exposure through the 1:3 isolated left pattern, for forming a half-pitch 1:1 pattern.

Although the pattern forming process often uses an alkaline aqueous solution as the developer, the negative tone development technique wherein the unexposed region is developed and dissolved in an organic solvent is also applicable.

In the organic solvent development, the organic solvent used as the developer is preferably selected from 2-octanone, 2-nonanone, 2-heptanone, 3-heptanone, 4-heptanone, 2-hexanone, 3-hexanone, diisobutyl ketone, methylcyclohexanone, acetophenone, methylacetophenone, propyl acetate, butyl acetate, isobutyl acetate, pentyl acetate, isopentyl acetate, butenyl acetate, phenyl acetate, propyl formate, butyl formate, isobutyl formate, pentyl formate, isopentyl formate, methyl valerate, methyl pentenoate, methyl crotonate, ethyl crotonate, methyl lactate, ethyl lactate, propyl lactate, butyl lactate, isobutyl lactate, pentyl lactate, isopentyl lactate, methyl 2-hydroxyisobutyrate, ethyl 2-hydroxyisobutyrate, methyl benzoate, ethyl benzoate, benzyl acetate, methyl phenylacetate, benzyl formate, phenylethyl formate, methyl 3-phenylpropionate, benzyl propionate, ethyl phenylacetate, and 2-phenylethyl acetate. These organic solvents may be used alone or in admixture of two or more.

EXAMPLE

Examples of the invention are given below by way of illustration and not by way of limitation. The abbreviation "pbw" is parts by weight. MIBK stands for methyl isobutyl ketone, and PGMEA for propylene glycol monomethyl ether acetate. Analytic instruments are as shown below.

IR: NICOLET 6700 by Thermo Fisher Scientific Inc.

$^1$H-NMR: ECA-500 by JEOL Ltd.

$^{19}$F-NMR: ECA-500 by JEOL Ltd.

MALDI-TOF-MS: S3000 by JEOL Ltd.

1) Synthesis of Carboxylic Acid Onium Salts

Synthesis Example 1

Synthesis of Intermediate A

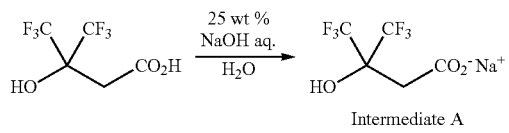

Intermediate A

A 100-ml three-necked flask was charged with 2.3 g of 3,3-bis(trifluoromethyl)-3-hydroxypropionic acid (Synquest Laboratories), 1.6 g of 25 wt % sodium hydroxide aqueous solution, and 5 g of water, which were stirred at room temperature for 30 minutes. MIBK, 50 g, was added to the reaction solution, which was concentrated, obtaining 2.4 g of Intermediate A as white solid (crude yield 96%). Intermediate A was used in the subsequent reaction without further purification.

Example 1-1

Synthesis of Carboxylic Acid Onium Salt Q-1

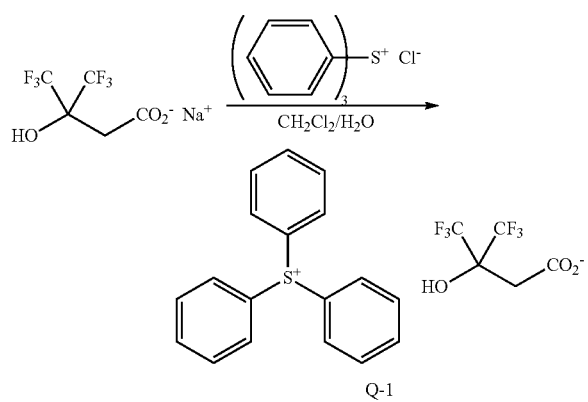

Q-1

A 100-ml three-necked flask was charged with 2.4 g of Intermediate A, 20 g of an aqueous solution of triphenylsulfonium chloride, and 20 g of methylene chloride, which were stirred for 30 minutes. The organic layer was separated, washed with water, and concentrated under reduced pressure. MIBK was added to the concentrate, which was concentrated by azeotroping off water. To the concentrate, diisopropyl ether was added for washing, obtaining the target compound, carboxylic acid onium salt Q-1, as oily matter (amount 4.2 g, yield 87%).

Figure 2:
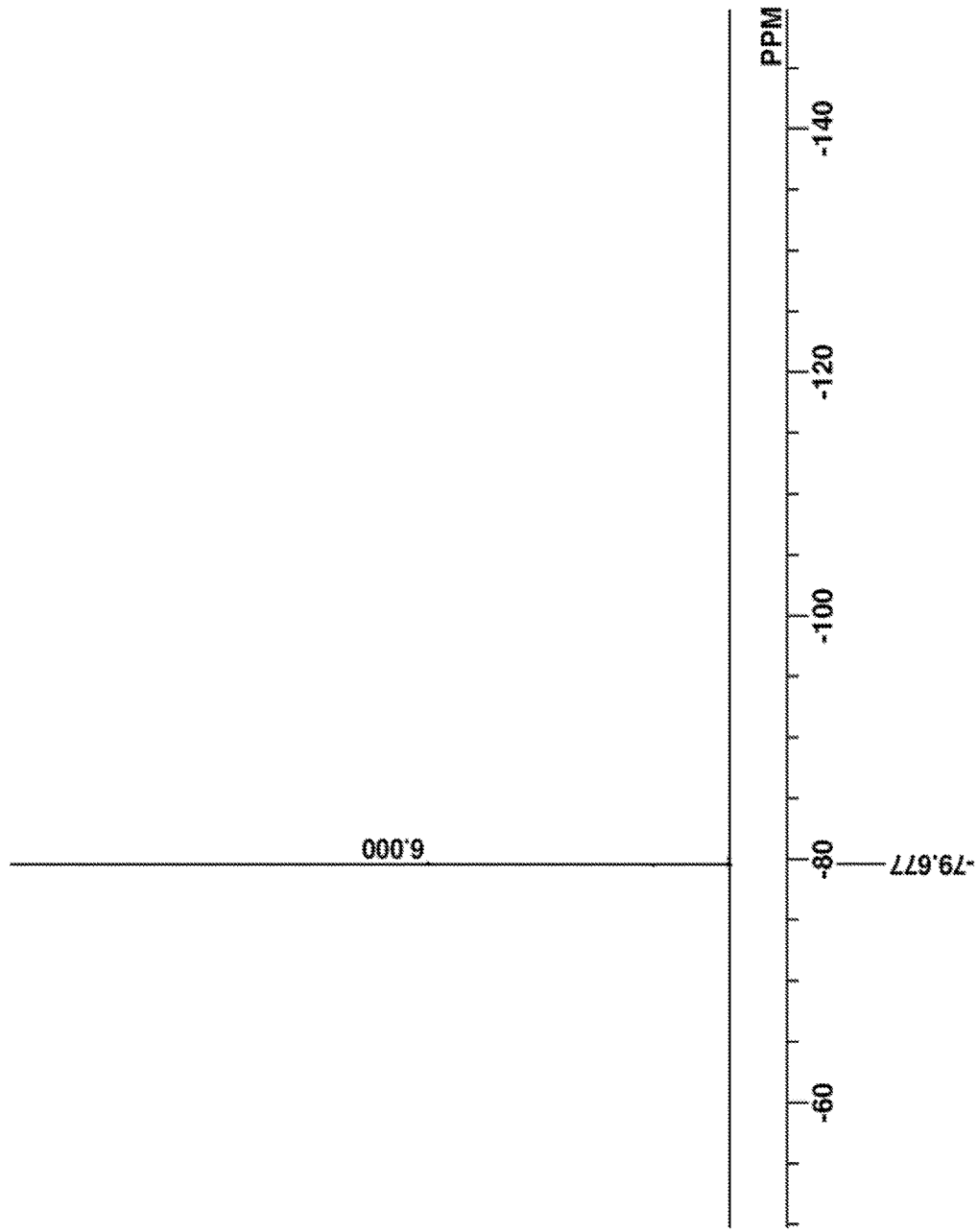
FIG. 2 is a diagram of ¹⁹F-NMR spectrum of the compound obtained in Synthesis Example 1-2.

The target compound was analyzed by spectroscopy. The NMR spectra, $^1$H and $^{19}$F-NMR in DMSO-$d_6$, are shown in FIGS. 1 and 2. In $^1$H-NMR analysis, minute amounts of residual solvents (methylene chloride, diisopropyl ether, MIBK, water) were observed.

Infrared absorption spectrum (IR (D-ATR)):
  $\nu$=3400, 3060, 1650, 1582, 1476, 1448, 1329, 1294, 1274, 1226, 1195, 1139, 1066, 1032, 999, 905, 882, 749, 703, 684, 613 cm$^{-1}$ Time-of-flight mass spectrometry (TOFMS; MALDI)
  Positive M$^+$ 263 (corresponding to $C_{18}H_{15}S^+$)
  Negative M$^-$ 225 (corresponding to $C_5H_3F_6O_3^-$)

Example 1-2

Synthesis of carboxylic acid onium salt Q-2

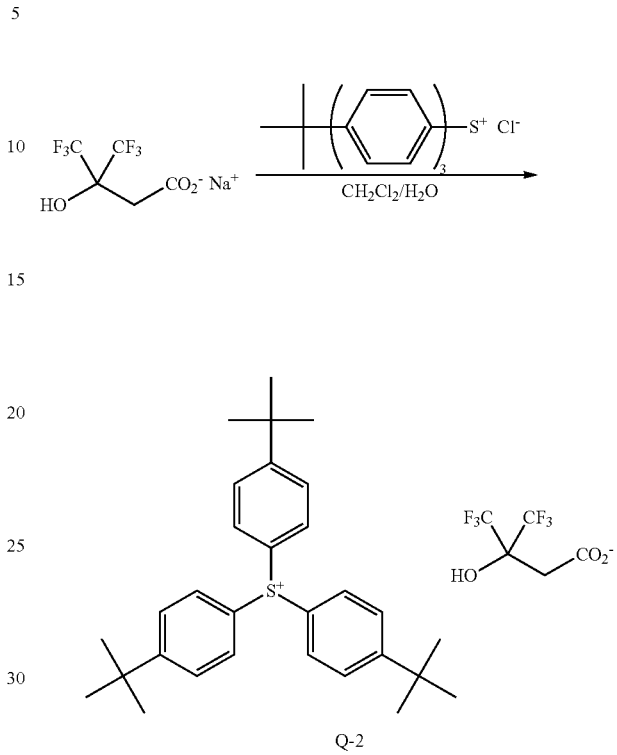

Q-2

Carboxylic acid onium salt Q-2 was synthesized according to the same formulation as in Example 1-1 aside from using tris(4-tert-butylphenyl)sulfonium chloride instead of triphenylsulfonium chloride. Yield 75%.

Figure 3:
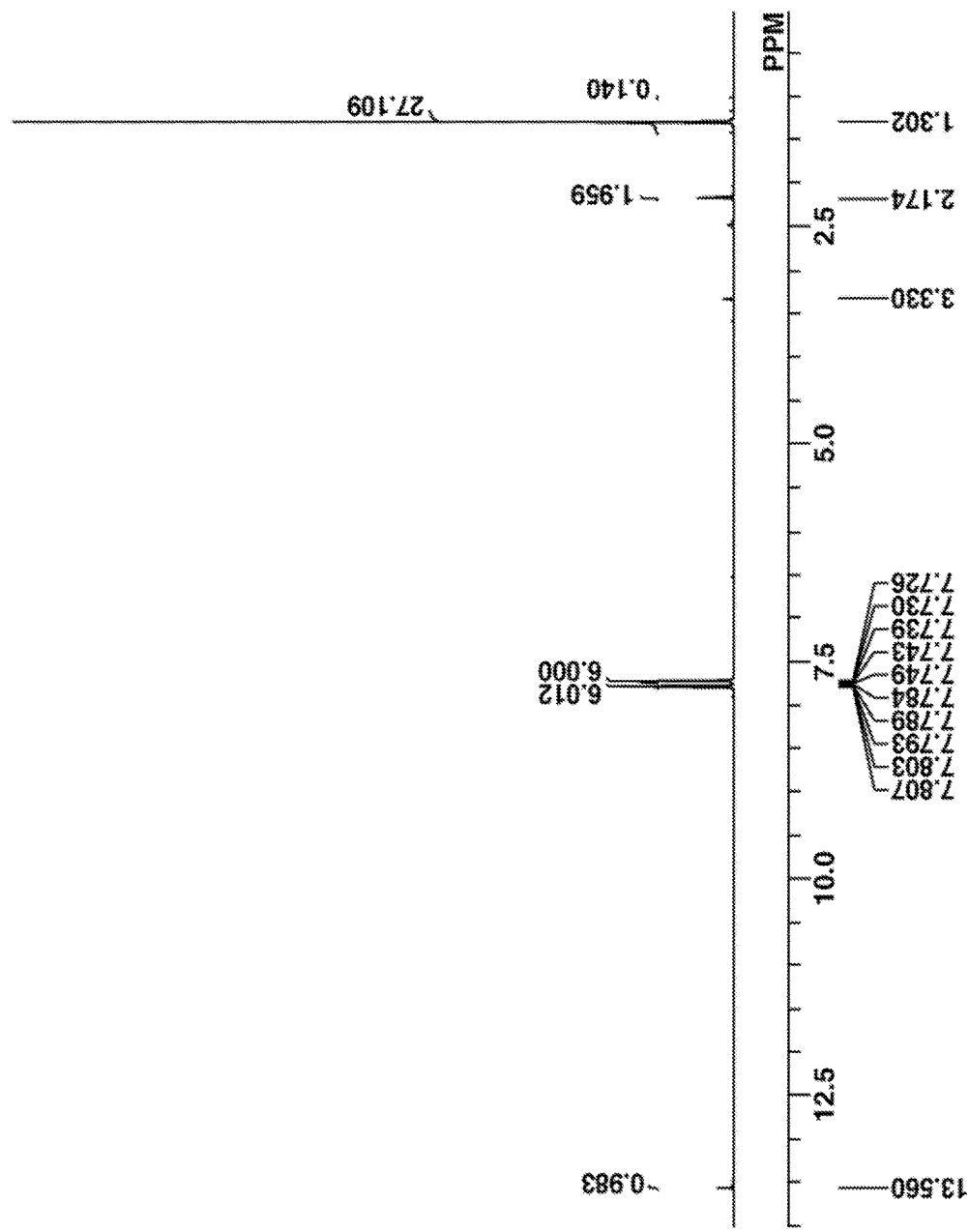
FIGS. 3 and 4 are diagrams of ¹H- and ¹⁹F-NMR spectra of the compound obtained in Synthesis Example 1-3, respectively.
Figure 4:
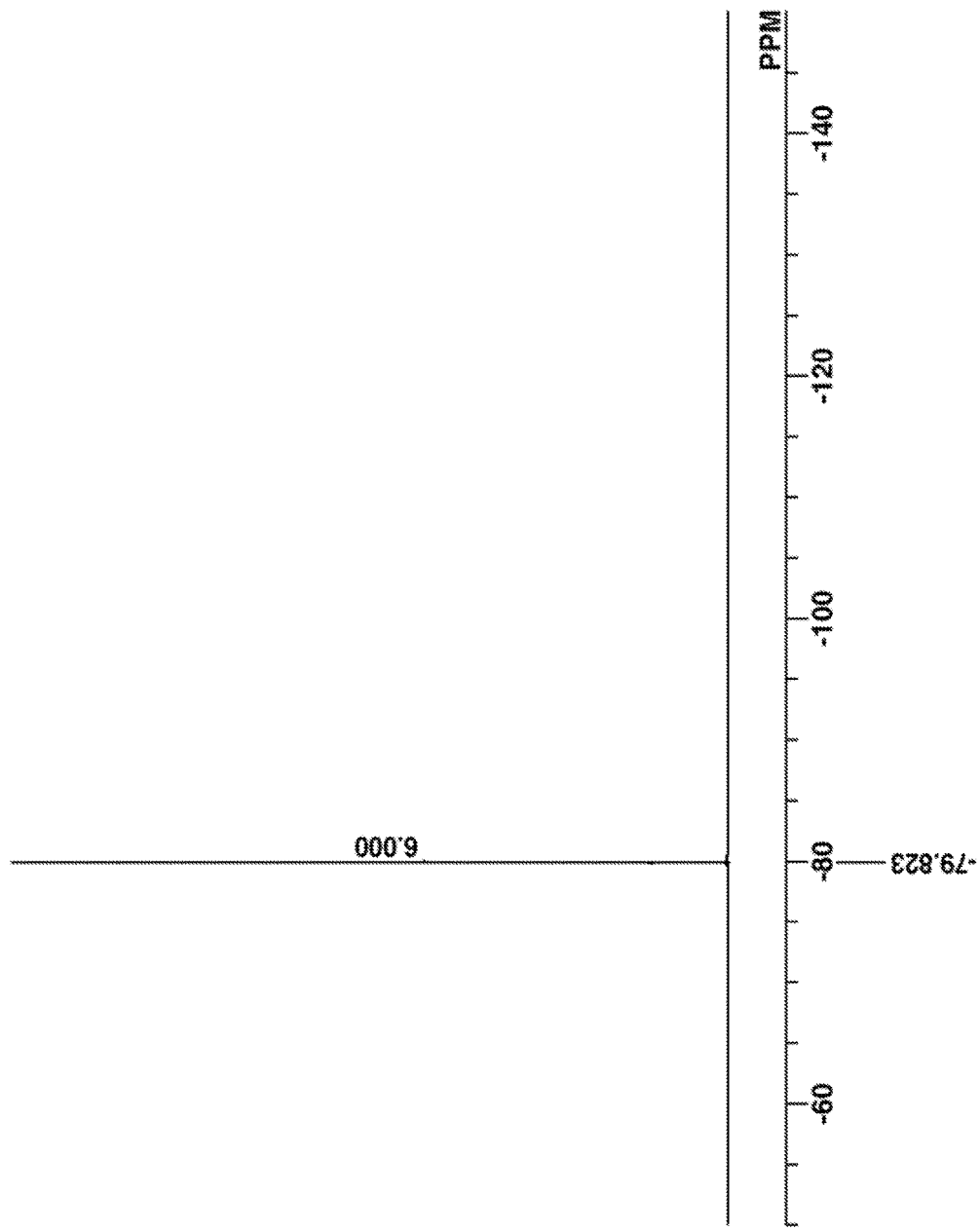

The target compound was analyzed by spectroscopy. The NMR spectra, $^1$H and $^{19}$F-NMR in DMSO-$d_6$, are shown in FIGS. 3 and 4. In $^1$H-NMR analysis, minute amounts of residual solvents (diisopropyl ether, MINK, water) were observed.

IR (D-ATR):
  $\nu$=3469, 3060, 2965, 2908, 2871, 1653, 1588, 1468, 1402, 1366, 1328, 1293, 1272, 1222, 1191, 1138, 1112, 1072, 1032, 1000, 902, 833, 725, 702, 682, 636, 597 cm$^{-1}$

TOFMS; MALDI
  Positive M$^+$ 431 (corresponding to $C_{30}HF_{39}S^+$)
  Negative M$^-$ 225 (corresponding to $C_5H_3F_6O_3^-$)

Example 1-3

Synthesis of Carboxylic Acid Onium Salt Q-3

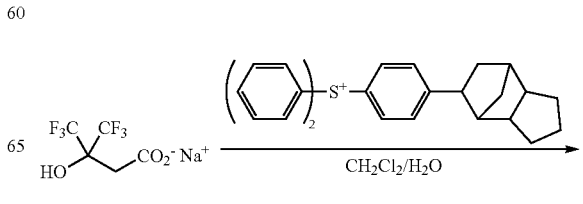

-continued

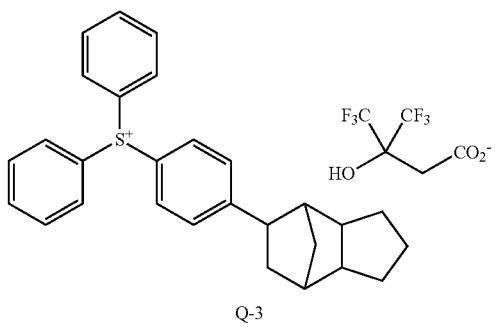

Q-3

Carboxylic acid onium salt Q-3 was synthesized according to the same formulation as in Example 1-1 aside from using [4-(octahydro-4,7-methanoinden-5-yl)phenyl]-diphenylsulfonium chloride instead of triphenylsulfonium chloride. Yield 89%.

Figure 5:
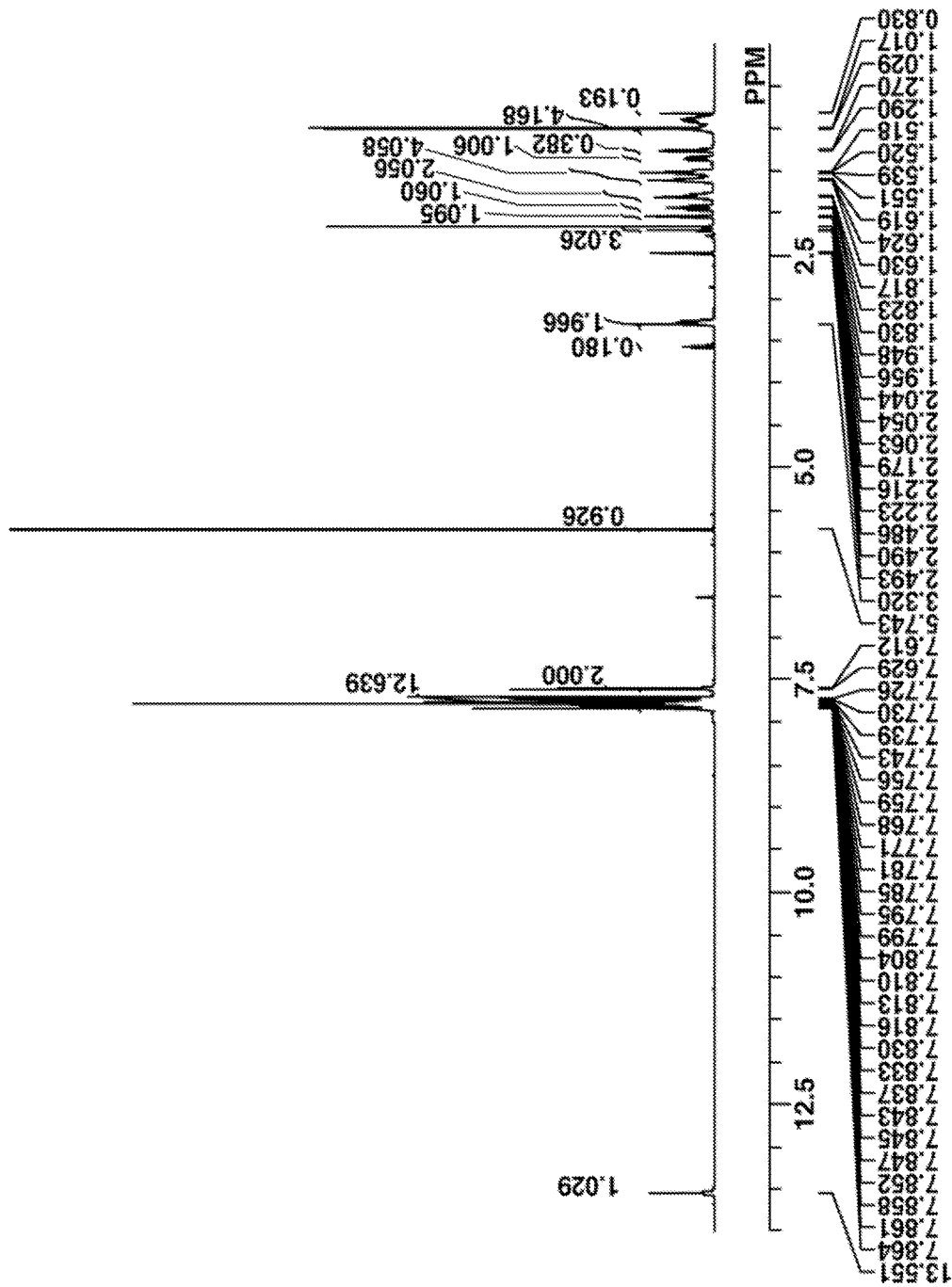
FIGS. 5 and 6 are diagrams of $^1$H- and $^{19}$F-NMR spectra of the compound obtained in Synthesis Example 1-4, respectively.
Figure 6:
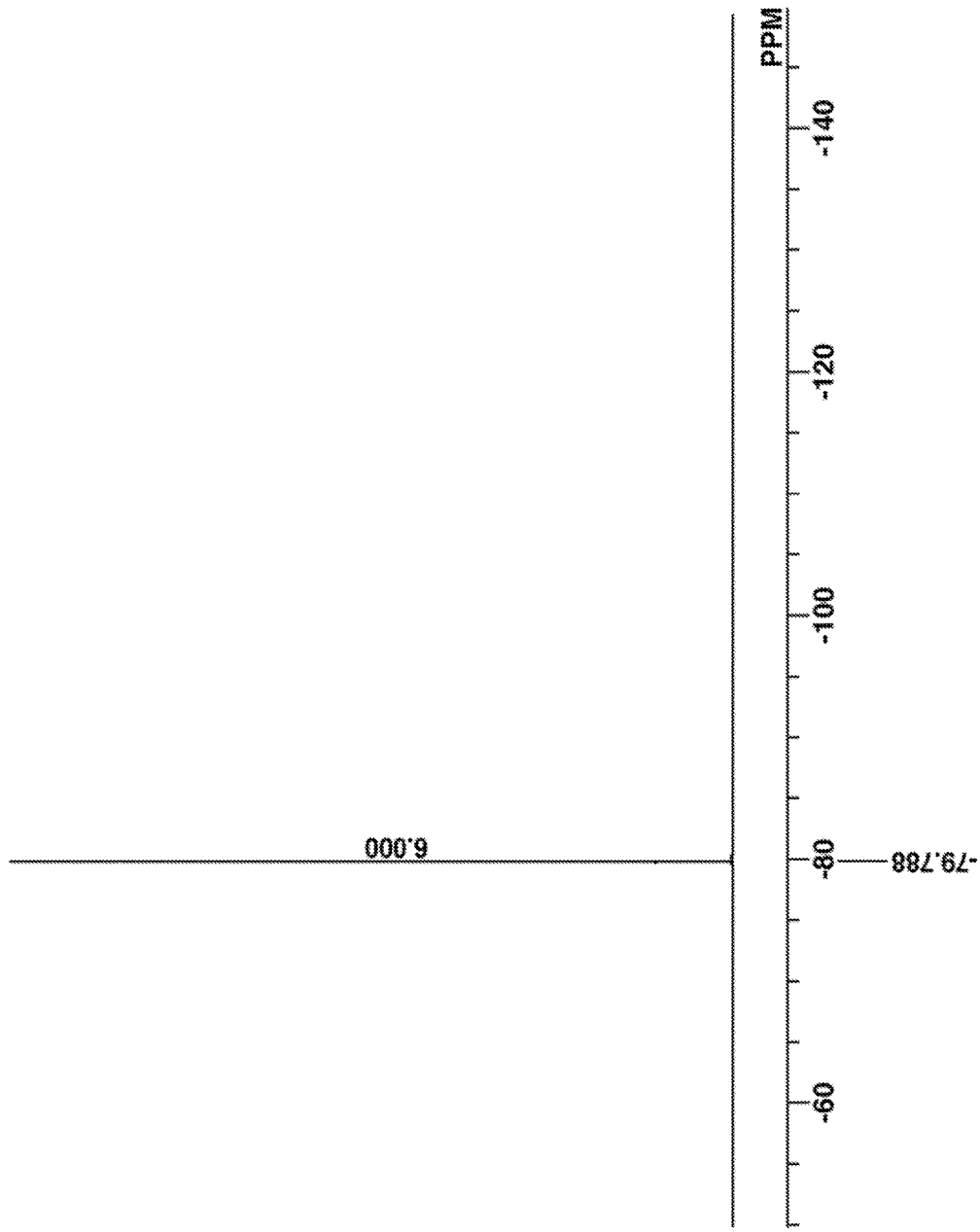

The target compound was analyzed by spectroscopy. The NMR spectra, $^1$H and $^{19}$F-NMR in DMSO-$d_6$, are shown in FIGS. 5 and 6. In $^1$H-NMR analysis, minute amounts of residual solvents (methylene chloride, diisopropyl ether, MIBK, water) were observed.

IR (D-ATR):
  v=3394, 3059, 2947, 2864, 1645, 1589, 1476, 1447, 1329, 1294, 1274, 1227, 1195, 1140, 1069, 1033, 1000, 906, 883, 854, 831, 787, 749, 703, 684, 628, 613, 571, 556 cm$^{-1}$

TOFMS; MALDI
  Positive M$^+$ 397 (corresponding to $C_{28}H_{29}S^+$)
  Negative M$^-$ 225 (corresponding to $C_5H_3F_6O_3^-$)

Examples 1-4 to 1-6

Synthesis of Carboxylic Acid Onium Salts Q-4 to Q-6

Carboxylic acid onium salts Q-4 to Q-6 of the following formulae were synthesized from corresponding reactants by well-known organic chemistry reactions.

Q-4

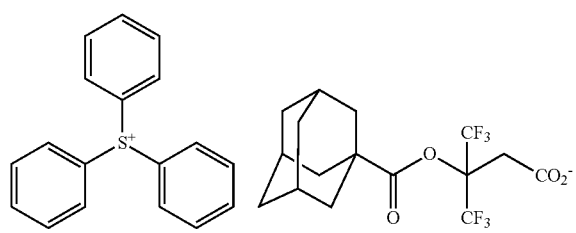

-continued

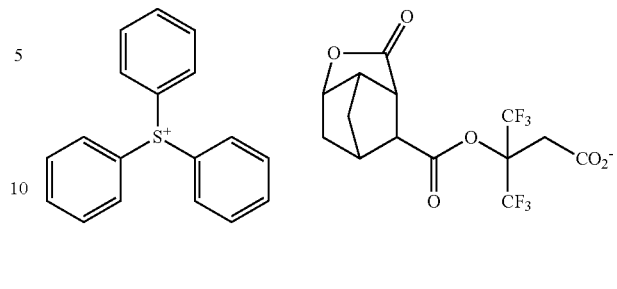

2) Synthesis of Polymers

Polymers for use in resist compositions were synthesized according to the following formulation. Notably, Mw is measured by GPC versus polystyrene standards using tetrahydrofuran solvent, and Mw/Mn is a polydispersity index.

Synthesis Example 2-1

Synthesis of Polymer P1

Under a nitrogen blanket, a flask was charged with 4.7 g of 3-hydroxy-1-adamantyl methacrylate, 16.9 g of α-methacryloxy-γ-butyrolactone, 10.4 g of 3-ethyl-3-exo-tetracyclo [4.4.0.1$^{2,5}$.1$^{7,10}$]dodecyl methacrylate, 10.4 g of 1-tert-butylcyclopentyl methacrylate, 0.46 g of dimethyl 2,2'-azobis (2-methylpropionate) (V-601 by Wako Pure Chemical Industries, Ltd.), 0.39 g of 2-mercaptoethanol, and 79 g of PGMEA to form a monomer/initiator solution. Another flask under a nitrogen blanket was charged with 26 g of PGMEA and heated at 80° C. with stirring, after which the monomer/initiator solution was added dropwise over 4 hours. After the completion of dropwise addition, the polymerization solution was continuously stirred for 2 hours while keeping the temperature of 80° C. It was then cooled to room temperature. With vigorous stirring, the polymerization solution was added dropwise to 640 g of methanol where a copolymer precipitated. The copolymer was collected by filtration, washed twice with 240 g of methanol, and vacuum dried at 50° C. for 20 hours, obtaining 35.3 g of the copolymer in white powder form (yield 88%). The copolymer (designated Polymer P1) was analyzed for composition. On GPC analysis, the copolymer had a Mw of 6,480 and a Mw/Mn of 1.74.

Polymer P1

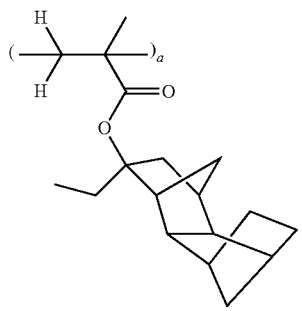
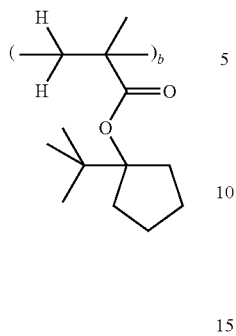

(a = 0.15, b = 0.25, c = 0.50, d = 0.10)

Synthesis Examples 2-2 to 2-14

Synthesis of Polymers P2 to P14

Polymers P2 to P14 were prepared by the same procedure as in Synthesis Example 2-1 except that the type and amount of monomers used were changed.

The compositional proportions of the polymers thus prepared are shown in Table 1 where values are molar ratios of monomer units incorporated. The structures of units in Table 1 are shown in Tables 2 to 4.

TABLE 1

| Polymer | Unit 1 | (ratio) | Unit 2 | (ratio) | Unit 3 | (ratio) | Unit 4 | (ratio) | Mw | Mw/Mn |
|---|---|---|---|---|---|---|---|---|---|---|
| P1 | A-1 | 0.15 | A-3 | 0.25 | B-4 | 0.50 | B-6 | 0.10 | 6,480 | 1.74 |
| P2 | A-1 | 0.15 | A-2 | 0.25 | B-4 | 0.50 | B-6 | 0.10 | 6,520 | 1.72 |
| P3 | A-1 | 0.15 | A-4 | 0.25 | B-4 | 0.50 | B-6 | 0.10 | 6,350 | 1.69 |
| P4 | A-1 | 0.15 | A-5 | 0.25 | B-4 | 0.50 | B-6 | 0.10 | 6,450 | 1.70 |
| P5 | A-1 | 0.15 | A-6 | 0.25 | B-4 | 0.50 | B-6 | 0.10 | 6,530 | 1.68 |
| P6 | A-1 | 0.15 | A-3 | 0.25 | B-1 | 0.50 | B-6 | 0.10 | 6,270 | 1.74 |
| P7 | A-1 | 0.15 | A-3 | 0.25 | B-2 | 0.50 | B-6 | 0.10 | 6,810 | 1.67 |
| P8 | A-1 | 0.15 | A-3 | 0.25 | B-3 | 0.50 | B-6 | 0.10 | 6,530 | 1.72 |
| P9 | A-1 | 0.15 | A-3 | 0.25 | B-5 | 0.50 | B-6 | 0.10 | 6,410 | 1.65 |
| P10 | A-1 | 0.40 | B-4 | 0.50 | B-6 | 0.10 | — | | 6,380 | 1.71 |
| P11 | A-2 | 0.20 | A-3 | 0.20 | B-2 | 0.50 | B-6 | 0.10 | 6,600 | 1.69 |
| P12 | A-4 | 0.20 | A-6 | 0.20 | B-3 | 0.50 | B-6 | 0.10 | 6,590 | 1.64 |
| P13 | A-1 | 0.15 | A-3 | 0.32 | B-4 | 0.50 | C-1 | 0.03 | 6,910 | 1.75 |
| P14 | A-1 | 0.15 | A-3 | 0.32 | B-4 | 0.50 | C-2 | 0.03 | 6,870 | 1.71 |

TABLE 2

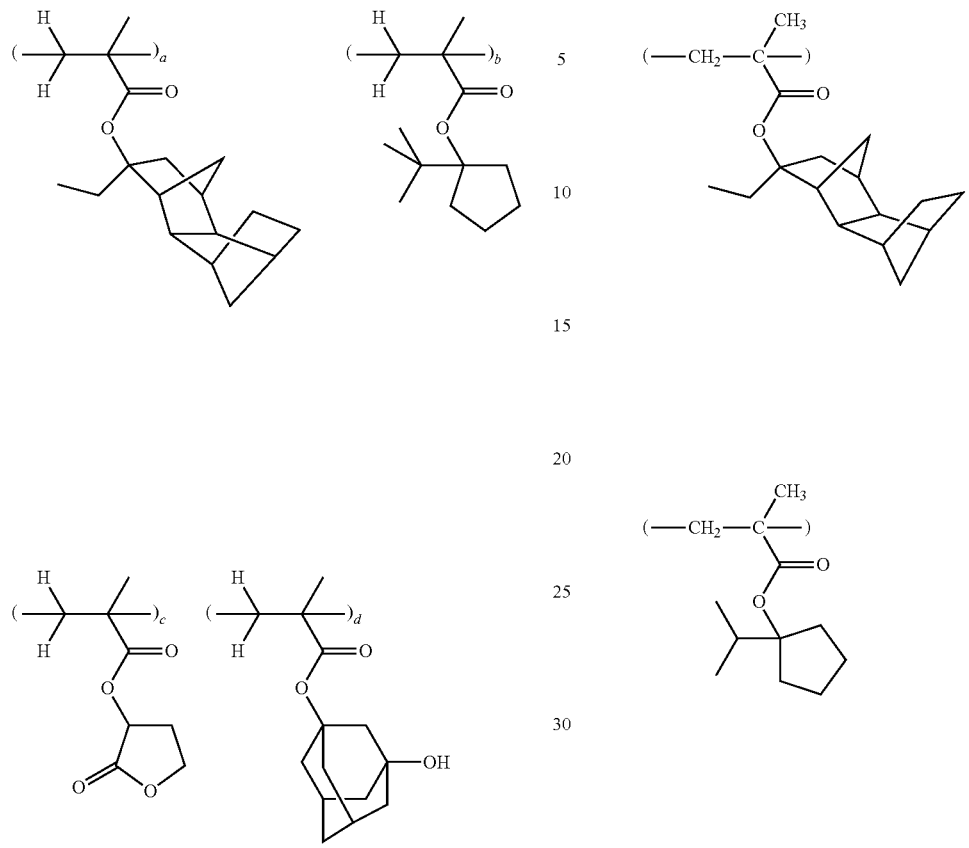

TABLE 2-continued
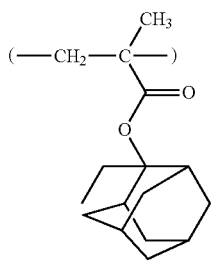 [SMILES: CCC(C)(C)C(=O)OC1(CC)C2CC3CC(C2)CC1C3]
A-4
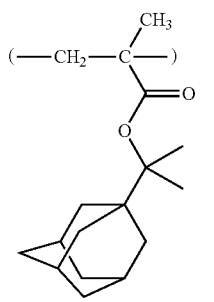 [SMILES: CCC(C)(C)C(=O)OC(C)(C)C12CC3CC(CC(C3)C1)C2]
A-5
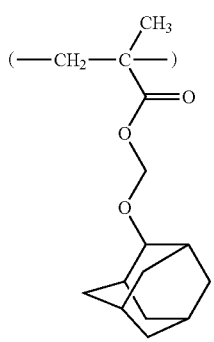 [SMILES: CCC(C)(C)C(=O)OCOC1C2CC3CC(C2)CC1C3]
A-6
TABLE 3
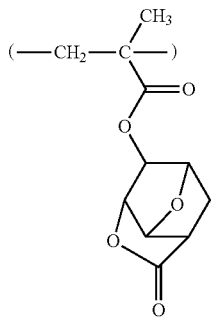 [SMILES: CCC(C)(C)C(=O)OC1C2CC3C(=O)OC1C3O2]
B-1
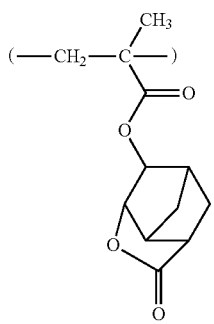 [SMILES: CCC(C)(C)C(=O)OC1C2CC3C(=O)OC1C3C2]
B-2
TABLE 3-continued
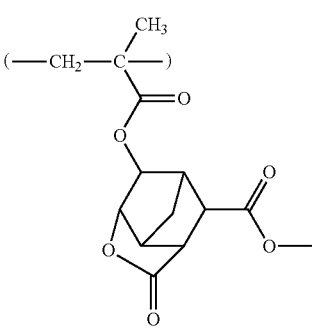 [SMILES: CCC(C)(C)C(=O)OC1C2CC3C1OC(=O)C3C2C(=O)OC]
B-3
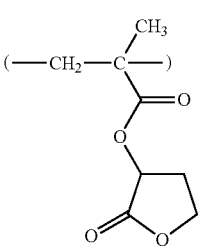
B-4
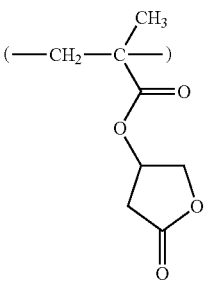
B-5
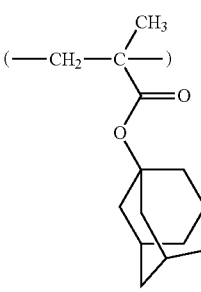
B-6

TABLE 4

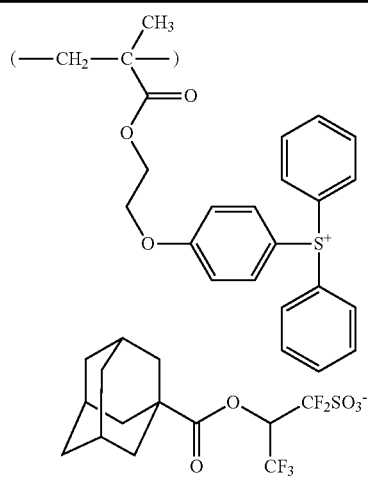
C-1

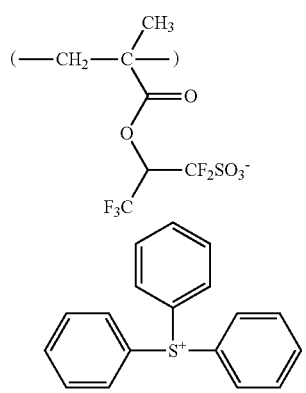
C-2

3) Preparation of Resist Compositions

Examples 2-1 to 2-19 and Comparative Examples 1-1 to 1-8

A resist solution was prepared by selecting an acid diffusion inhibitor (Q-1 to Q-6) or comparative acid diffusion inhibitor (Q-A to Q-H), polymer (P1 to P14), PAG, and alkali-soluble surfactant SF-1 in accordance with the formulation shown in Tables 5 and 6, dissolving the components in a solvent, and filtering through a Teflon® filter having a pore size of 0.2 μm. The solvent contained 0.01 wt % of surfactant A.

The solvent, PAG, alkali-soluble surfactant SF-1, surfactant A, and comparative acid diffusion inhibitors (Q-A to Q-H) in Tables 5 and 6 are identified below.

Solvent:
  PGMBA (propylene glycol monomethyl ether acetate)
  GBL (γ-butyrolactone)

PAG:
  compounds of the following formulae

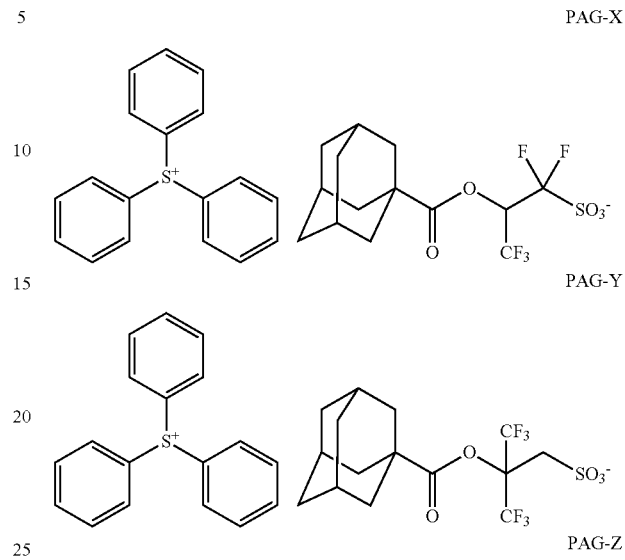

PAG-X

PAG-Y

PAG-Z

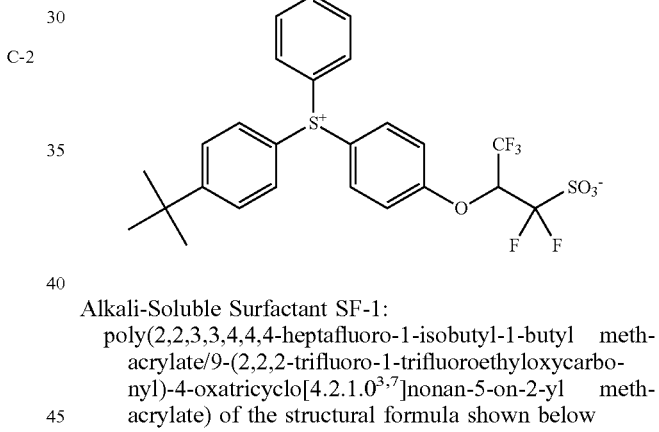

Alkali-Soluble Surfactant SF-1:
  poly(2,2,3,3,4,4,4-heptafluoro-1-isobutyl-1-butyl methacrylate/9-(2,2,2-trifluoro-1-trifluoroethyloxycarbonyl)-4-oxatricyclo[4.2.1.0$^{3,7}$]nonan-5-on-2-yl methacrylate) of the structural formula shown below
  Mw=7,700
  Mw/Mn=1.82

SF-1

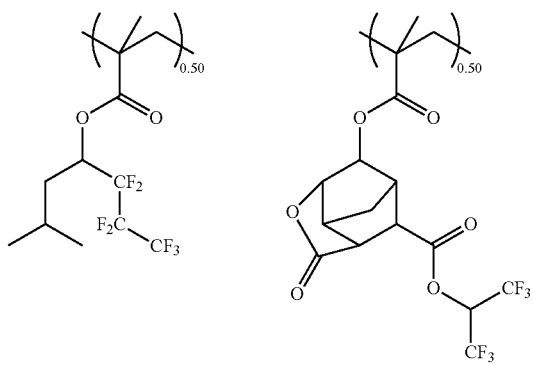

Comparative Acid Diffusion Inhibitors:
Onium salts of the following formulae
Q-A
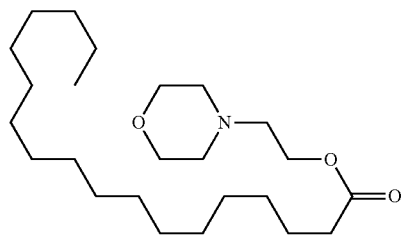
Q-B
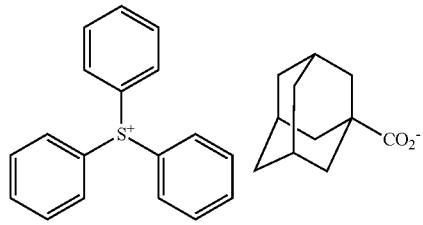
Q-C
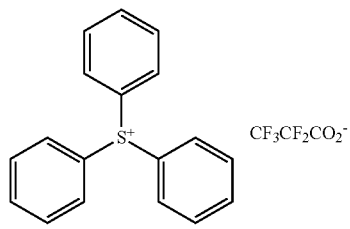
Q-D
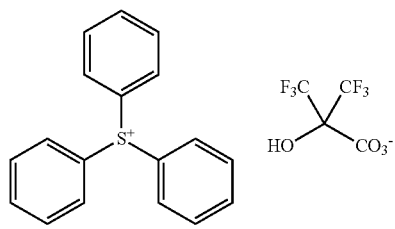
Q-E
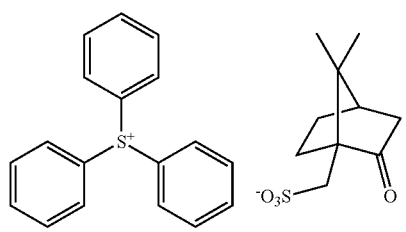
Q-F
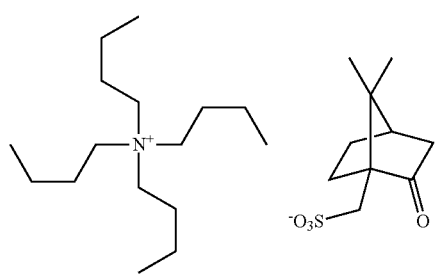
Q-G
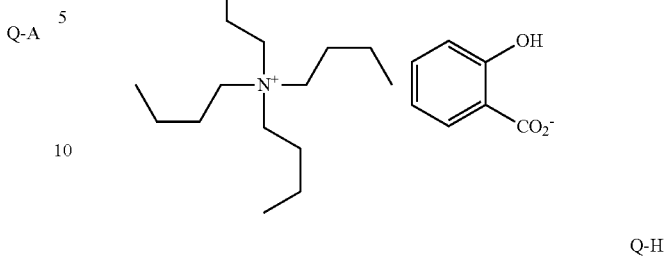
Q-H
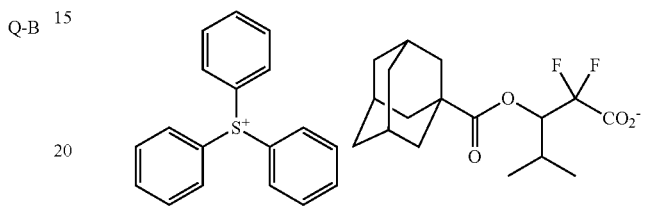
Surfactant A:
3-methyl-3-(2,2,2-trifluoroethoxymethyl)oxetane/tetrahydrofuran/2,2-dimethyl-1,3-propanediol copolymer (Omnova Solutions, Inc.) of the structural formula shown below
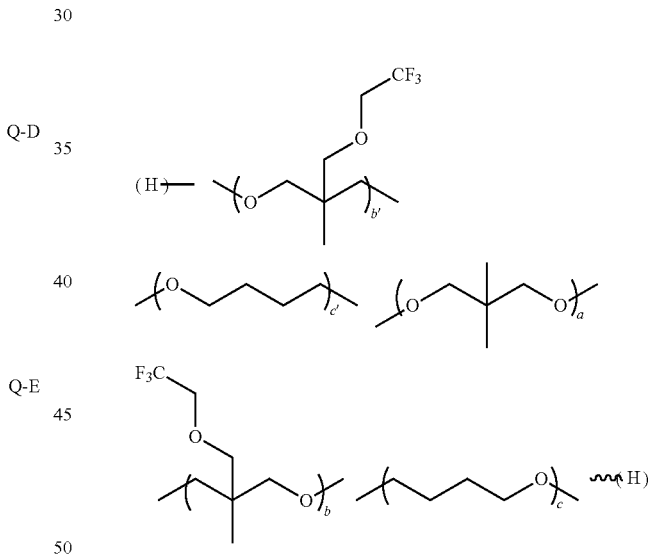
a:(b+b'):(c+c')=1:4-7:0.01-1 (molar ratio)
Mw=1,500

TABLE 5

| | Resist | Resin (pbw) | PAG (pbw) | Acid diffusion inhibitor (pbw) | Surfactant (pbw) | Solvent 1 (pbw) | Solvent 2 (pbw) |
|---|---|---|---|---|---|---|---|
| Example 2-1 | R-1 | P-1 (80) | PAG-Z (7.6) | Q-1 (3.5) | SF-1 (3.0) | PGMEA (1,728) | GBL (192) |
| Example 2-2 | R-2 | P-1 (80) | PAG-Z (7.6) | Q-2 (3.5) | SF-1 (3.0) | PGMEA (1,728) | GBL (192) |
| Example 2-3 | R-3 | P-1 (80) | PAG-Z (7.6) | Q-3 (3.5) | SF-1 (3.0) | PGMEA (1,728) | GBL (192) |
| Example 2-4 | R-4 | P-1 (80) | PAG-Z (7.6) | Q-4 (3.5) | SF-1 (3.0) | PGMEA (1,728) | GBL (192) |
| Example 2-5 | R-5 | P-1 (80) | PAG-Z (7.6) | Q-5 (3.5) | SF-1 (3.0) | PGMEA (1,728) | GBL (192) |
| Example 2-6 | R-6 | P-1 (80) | PAG-Z (7.6) | Q-6 (3.5) | SF-1 (3.0) | PGMEA (1,728) | GBL (192) |
| Example 2-7 | R-7 | P-2 (80) | PAG-X (7.6) | Q-2 (3.5) | SF-1 (3.0) | PGMEA (1,728) | GBL (192) |
| Example 2-8 | R-8 | P-3 (80) | PAG-X (5.0) | Q-4 (3.5) | SF-1 (3.0) | PGMEA (1,728) | GBL (192) |
| Example 2-9 | R-9 | P-4 (80) | PAG-X (5.0) | Q-2 (3.5) | SF-1 (3.0) | PGMEA (1,728) | GBL (192) |
| Example 2-10 | R-10 | P-5 (80) | PAG-X (5.0) | Q-2 (0.5) | SF-1 (3.0) | PGMEA (1,728) | GBL (192) |
| Example 2-11 | R-11 | P-6 (80) | PAG-X (5.0) | Q-2 (3.5) | SF-1 (3.0) | PGMEA (1,728) | GBL (192) |
| Example 2-12 | R-12 | P-7 (80) | PAG-X (5.0) | Q-2 (3.5) | SF-1 (3.0) | PGMEA (1,728) | GBL (192) |
| Example 2-13 | R-13 | P-8 (80) | PAG-X (5.0) | Q-2 (3.5) | SF-1 (3.0) | PGMEA (1,728) | GBL (192) |
| Example 2-14 | R-14 | P-9 (80) | PAG-X (5.0) | Q-4 (3.5) | SF-1 (3.0) | PGMEA (1,728) | GBL (192) |
| Example 2-15 | R-15 | P-10 (80) | PAG-X (5.0) | Q-6 (3.5) | SF-1 (3.0) | PGMEA (1,728) | GBL (192) |
| Example 2-16 | R-16 | P-11 (80) | PAG-X (5.0) | Q-2 (3.5) | SF-1 (3.0) | PGMEA (1,728) | GBL (192) |
| Example 2-17 | R-17 | P-12 (80) | PAG-Y (11.2) | Q-5 (3.5) | SF-1 (3.0) | PGMEA (1,728) | GBL (192) |
| Example 2-18 | R-18 | P43 (80) | — | Q-2 (3.5) | SF-1 (3.0) | PGMEA (1,728) | GBL (192) |
| Example 2-19 | R-19 | P-14 (80) | — | Q-2 (3.5) | SF-1 (3.0) | PGMEA (1,728) | GBL (192) |

TABLE 6

| | Resist | Resin (pbw) | PAG (pbw) | Acid diffusion inhibitor (pbw) | Surfactant (pbw) | Solvent 1 (pbw) | Solvent 2 (pbw) |
|---|---|---|---|---|---|---|---|
| Comparative Example 1-1 | R-20 | P-1 (80) | PAG-Z (7.6) | Q-A (3.5) | SF-1 (3.0) | PGMEA (1,728) | GBL (192) |
| Comparative Example 1-2 | R-21 | P-1 (80) | PAG-Z (7.6) | Q-B (3.5) | SF-1 (3.0) | PGMEA (1,728) | GBL (192) |
| Comparative Example 1-3 | R-22 | P-1 (80) | PAG-Z (7.6) | Q-C (3.5) | SF-1 (3.0) | PGMEA (1,728) | GBL (192) |
| Comparative Example 1-4 | R-23 | P-1 (80) | PAG-Z (7.6) | Q-D (3.5) | SF-1 (3.0) | PGMEA (1,728) | GBL (192) |
| Comparative Example 1-5 | R-24 | P-1 (80) | PAG-Z (7.6) | Q-E (3.5) | SF-1 (3.0) | PGMEA (1,728) | GBL (192) |
| Comparative Example 1-6 | R-25 | P-1 (80) | PAG-Z (7.6) | Q-F (3.5) | SF-1 (3.0) | PGMEA (1,728) | GBL (192) |
| Comparative Example 1-7 | R-26 | P-1 (80) | PAG-Z (7.6) | Q-G (3.5) | SF-1 (3.0) | PGMEA (1,728) | GBL (192) |
| Comparative Example 1-8 | R-27 | P-1 (80) | PAG-Z (7.6) | Q-H (3.5) | SF-1 (3.0) | PGMEA (1,728) | GBL (192) |

4) Evaluation of Resist Composition: ArF Lithography Test 1

Examples 3-1 to 3-19 and Comparative Examples 2-1 to 2-8

An antireflective coating solution (ARC-29A by Nissan Chemical Industries, Ltd.) was coated onto a silicon substrate and baked at 200° C. for 60 seconds to form an ARC film of 100 nm thick. The resist solution (R-1 to R-27) in Table 5 or 6 was spin coated onto the ARC and baked on a hot plate at 100° C. for 60 seconds to form a resist film of 90 nm thick. The resist film was exposed according to the ArF immersion lithography using an ArF excimer laser scanner (model NSR-S610C, Nikon Corp., NA 1.30, dipole illumination, Cr mask). The resist film was baked (PEB) at 80° C. for 60 seconds and developed in a 2.38 wt % tetramethylammonium hydroxide aqueous solution for 60 seconds.

Evaluation Method

The resist was evaluated by observing a 40-nm 1:1 line-and-space pattern under an electron microscope. The optimum dose (Eop) was a dose (mJ/cm$^2$) which provided a line width of 40 nm. The profile of a pattern at the optimum dose was compared and judged good or poor.

The width of lines of a 40-nm 1:1 line-and-space pattern was measured under SEM to determine a line width variation (30 points measured, 3σ value computed), which was reported as line width roughness (LWR). A smaller value of LWR indicates a line pattern with a less fluctuation and of better profile. In this test, the sample is rated good when LWR is less than 3.3 nm and poor when LWR is equal to or more than 3.3 nm.

Defects in the pattern as developed were inspected by a flaw detector KLA2800 (KLA-Tencor). A defect density (count/cm$^2$) was computed by dividing the total number of detected defects by a detection area. The pattern formed was an iterated 40-nm 1:1 line-and-space pattern. The defect inspection conditions included light source UV, inspected pixel size 0.28 μm, and cell-to-cell mode. In this test, the sample was rated good for a defect density of less than 0.05 defect/cm$^2$ and poor for a density of equal to or more than 0.05 defect/cm$^2$.

The collapse limit was a minimum width (nm) of lines which could be resolved without collapse when the line width was reduced by increasing the exposure dose. A smaller value indicates better collapse resistance.

The test results of the resist compositions are shown in Tables 7 and 8.

TABLE 7

| | Resist | $E_{op}$ (mJ/cm$^2$) | Pattern Profile | LWR (nm) | Defect density (count/cm$^2$) | Collapse limit (nm) |
|---|---|---|---|---|---|---|
| Example 3-1 | R-1 | 40 | rectangular | 3.2 | 0.02 | 29 |
| Example 3-2 | R-2 | 41 | rectangular | 3.1 | 0.01 | 30 |
| Example 3-3 | R-3 | 39 | rectangular | 3.1 | 0.03 | 28 |
| Example 3-4 | R-4 | 40 | rectangular | 3.0 | 0.02 | 29 |
| Example 3-5 | R-5 | 41 | rectangular | 3.0 | 0.01 | 30 |
| Example 3-6 | R-6 | 40 | rectangular | 2.9 | 0.03 | 31 |
| Example 3-7 | R-7 | 40 | rectangular | 3.1 | 0.02 | 32 |
| Example 3-8 | R-8 | 40 | rectangular | 3.0 | 0.02 | 31 |
| Example 3-9 | R-9 | 42 | rectangular | 2.9 | 0.03 | 30 |
| Example 3-10 | R-10 | 38 | rectangular | 2.9 | 0.02 | 30 |
| Example 3-11 | R-11 | 39 | rectangular | 3.0 | 0.01 | 29 |
| Example 3-12 | R-12 | 41 | rectangular | 3.2 | 0.02 | 28 |
| Example 3-13 | R-13 | 40 | rectangular | 3.1 | 0.01 | 31 |
| Example 3-14 | R-14 | 41 | rectangular | 3.0 | 0.02 | 30 |
| Example 3-15 | R-15 | 38 | rectangular | 3.1 | 0.01 | 29 |
| Example 3-16 | R-16 | 41 | rectangular | 2.9 | 0.03 | 30 |
| Example 3-17 | R-17 | 39 | rectangular | 3.1 | 0.02 | 31 |
| Example 3-18 | R-18 | 40 | rectangular | 2.9 | 0.02 | 28 |
| Example 3-19 | R-19 | 40 | rectangular | 2.8 | 0.03 | 29 |

TABLE 8

| | Resist | $E_{op}$ (mJ/cm$^2$) | Pattern Profile | LWR (nm) | Defect density (count/cm$^2$) | Collapse limit (nm) |
|---|---|---|---|---|---|---|
| Comparative Example 2-1 | R-20 | 47 | poor, T-top | 4.3 | 0.09 | 45 |
| Comparative Example 2-2 | R-21 | 44 | poor, some footing | 3.9 | 0.09 | 43 |
| Comparative Example 2-3 | R-22 | 43 | poor, some footing | 4.0 | 0.08 | 41 |
| Comparative Example 2-4 | R-23 | 42 | poor, some footing | 4.1 | 0.07 | 40 |
| Comparative Example 2-5 | R-24 | 42 | poor, some footing | 4.0 | 0.08 | 42 |
| Comparative Example 2-6 | R-25 | 48 | poor, some footing | 3.9 | 0.09 | 43 |
| Comparative Example 2-7 | R-26 | 47 | poor, some footing | 3.8 | 0.08 | 39 |
| Comparative Example 2-8 | R-27 | 42 | poor, some footing | 3.7 | 0.06 | 38 |

It is evident from the data of Tables 7 and 8 that the resist compositions within the scope of the invention form patterns of good profile having a high resolution, minimal LWR, and low defect density. They are thus best suited as the ArF immersion lithography material.

5) Evaluation of Resist Composition: ArF Lithography Test 2

Examples 4-1 to 4-19 and Comparative Examples 3-1 to 3-8

On a substrate, a spin-on carbon film ODL-50 (Shin-Etsu Chemical Co., Ltd.) having a carbon content of 80 wt % was deposited to a thickness of 200 nm and a silicon-containing spin-on hard mask SHB-A940 having a silicon content of 43 wt % was deposited thereon to a thickness of 35 nm. On this substrate for trilayer process, the resist composition (R-1 to R-27) in Table 5 or 6 was spin coated, then baked on a hot plate at 100° C. for 60 seconds to form a resist film of 100 nm thick. Using an ArF excimer laser immersion lithography scanner NSR-610C (Nikon Corp., NA 1.30, σ 0.98/0.78, 4/5 annular illumination), pattern exposure was performed through Mask A or B described below.

Mask A is a 6% halftone phase shift mask bearing a line pattern with a pitch of 100 nm and a line width of 50 nm (on-wafer size). After exposure through Mask A, the wafer was baked (PEB) for 60 seconds and developed. Specifically, butyl acetate was injected from a development nozzle while the wafer was spun at 30 rpm for 3 seconds, which was followed by stationary puddle development for 27 seconds. As a result, the unexposed regions which had been masked with Mask A were dissolved in the developer, that is, image reversal took place to form a line-and-space (L/S) pattern with a space width of 50 nm and a pitch of 100 nm.

Mask B is a 6% halftone phase shift mask bearing a line pattern with a pitch of 200 nm and a line width of 45 nm (on-wafer size). After exposure through Mask B, the wafer was baked (PEB) for 60 seconds and developed. Specifically, butyl acetate was injected from a development nozzle while the wafer was spun at 30 rpm for 3 seconds, which was followed by stationary puddle development for 27 seconds. As a result, the unexposed regions which had been masked with Mask B were dissolved in the developer, that is, image reversal took place to form an isolated space pattern (referred to as "trench pattern", hereinafter) with a space width of 45 nm and a pitch of 200 nm.

Evaluation of Sensitivity

As an index of sensitivity, the optimum dose (Eop, mJ/cm$^2$) which provided an L/S pattern with a space width of 50 nm and a pitch of 100 nm on exposure through Mask A was determined.

Evaluation of Exposure Latitude (EL)

The exposure dose which provided an L/S pattern with a space width of 50 nm±10% (i.e., 45 nm to 55 nm) on exposure through Mask A was determined. EL (%) is calculated from the exposure doses according to the following equation:

$$EL(\%)=(|E1-E2|/Eop)\times 100$$

wherein E1 is an exposure dose which provides an L/S pattern with a space width of 45 nm and a pitch of 100 nm, E2 is an exposure dose which provides an L/S pattern with a space width of 55 nm and a pitch of 100 nm, and Eop is the optimum exposure dose which provides an L/S pattern with a space width of 50 nm and a pitch of 100 nm.

Evaluation of Line Width Roughness (LWR)

An L/S pattern was formed by exposure in the optimum dose (determined in the sensitivity evaluation) through Mask A. By observation under TDSEM S-9380 (Hitachi Hitechnologies, Ltd.), the space width was measured at longitudinally spaced apart 10 points, from which a 3-fold value (3σ) of standard deviation (σ) was determined and reported as LWR. A smaller value of 3σ indicates a pattern having a lower roughness and more uniform space width.

Evaluation of Mask Error Factor (MEF)

An L/S pattern was formed by exposure in the optimum dose (determined in the sensitivity evaluation) through Mask A with the pitch fixed and the line width varied. MEF was calculated from variations of the mask line width and the pattern space width according to the following equation:

$$MEF=(\text{pattern space width})/(\text{mask line width})-b$$

wherein b is a constant. A value closer to unity (1) indicates better performance.

Evaluation of Depth-of-Focus (DOF) Margin

The exposure dose and DOF which ensured to form a trench pattern with a space width of 35 nm on exposure through Mask B were defined as the optimum exposure dose and the optimum DOF, respectively. The depth (nm) over which focus was changed that could form a resist pattern with a space width of 35 nm±10% (i.e., 31.5 nm to 38.5 nm) was determined and reported as DOF. A larger value indicates a smaller change of pattern size with a change of DOF and hence, better DOF margin.

The results are shown in Tables 9 and 10.

TABLE 9

| | Resist | $E_{op}$ (mJ/cm$^2$) | EL (%) | LWR (nm) | MEF | DOF (nm) |
|---|---|---|---|---|---|---|
| Example 4-1 | R-1 | 40 | 18 | 3.2 | 3.2 | 150 |
| Example 4-2 | R-2 | 41 | 19 | 3.0 | 3.4 | 140 |
| Example 4-3 | R-3 | 39 | 18 | 3.1 | 3.3 | 150 |
| Example 4-4 | R-4 | 40 | 17 | 2.9 | 3.3 | 130 |
| Example 4-5 | R-5 | 41 | 19 | 3.0 | 3.2 | 140 |
| Example 4-6 | R-6 | 40 | 18 | 3.1 | 3.3 | 150 |
| Example 4-7 | R-7 | 40 | 19 | 3.2 | 3.5 | 150 |
| Example 4-8 | R-8 | 40 | 19 | 3.2 | 3.2 | 140 |
| Example 4-9 | R-9 | 42 | 18 | 3.3 | 3.4 | 130 |
| Example 4-10 | R-10 | 38 | 17 | 3.0 | 3.3 | 150 |
| Example 4-11 | R-11 | 39 | 19 | 3.1 | 3.2 | 140 |
| Example 4-12 | R-12 | 41 | 18 | 3.0 | 3.4 | 130 |
| Example 4-13 | R-13 | 40 | 19 | 2.9 | 3.2 | 150 |
| Example 4-14 | R-14 | 41 | 18 | 3.0 | 3.1 | 150 |
| Example 4-15 | R-15 | 38 | 18 | 3.1 | 3.3 | 140 |
| Example 4-16 | R-16 | 41 | 17 | 3.0 | 3.2 | 150 |
| Example 4-17 | R-17 | 39 | 18 | 2.9 | 3.2 | 150 |
| Example 4-18 | R-18 | 40 | 17 | 3.1 | 3.1 | 140 |
| Example 4-19 | R-19 | 40 | 18 | 3.2 | 3.1 | 150 |

TABLE 10

| | Resist | $E_{op}$ (mJ/cm$^2$) | EL (%) | LWR (nm) | MEF | DOF (nm) |
|---|---|---|---|---|---|---|
| Comparative Example 3-1 | R-20 | 47 | 10 | 4.6 | 4.3 | 70 |
| Comparative Example 3-2 | R-21 | 44 | 12 | 4.2 | 4.4 | 80 |
| Comparative Example 3-3 | R-22 | 43 | 11 | 4.0 | 4.5 | 80 |
| Comparative Example 3-4 | R-23 | 42 | 10 | 4.1 | 4.2 | 100 |
| Comparative Example 3-5 | R-24 | 42 | 12 | 4.5 | 4.3 | 90 |
| Comparative Example 3-6 | R-25 | 48 | 13 | 4.4 | 4.3 | 100 |

TABLE 10-continued

| | Resist | $E_{op}$ (mJ/cm$^2$) | EL (%) | LWR (nm) | MEF | DOF (nm) |
|---|---|---|---|---|---|---|
| Comparative Example 3-7 | R-26 | 47 | 10 | 4.3 | 4.4 | 80 |
| Comparative Example 3-8 | R-27 | 42 | 14 | 3.9 | 3.9 | 100 |

As seen from the results of Tables 9 and 10, the resist compositions within the scope of the invention form negative patterns via organic solvent development with the advantages of hole size uniformity, improved exposure latitude, LWR and MEF of L/S patterns, and improved DOF margin of trench patterns. The compositions are advantageously applicable to the organic solvent development process.

Japanese Patent Application No. 2016-090752 is incorporated herein by reference.

Although some preferred embodiments have been described, many modifications and variations may be made thereto in light of the above teachings. It is therefore to be understood that the invention may be practiced otherwise than as specifically described without departing from the scope of the appended claims.

The invention claimed is:

1. A carboxylic acid onium salt having the formula (1):

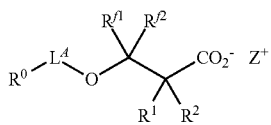

(1)

wherein $R^0$ is hydrogen, or a $C_1$-$C_{20}$ straight, branched or cyclic monovalent hydrocarbon group which may contain a heteroatom, $R^1$ and $R^2$ are each independently hydrogen, or a $C_1$-$C_{20}$ straight, branched or cyclic monovalent hydrocarbon group which may contain a hydroxyl moiety, cyano moiety, carbonyl moiety, ether bond, ester bond, sulfonate bond, carbonate bond, lactone ring, sultone ring, or carboxylic anhydride, or $R^1$ and $R^2$ may bond together to form a ring with the carbon atom to which they are attached, $R^{f1}$ and $R^{f2}$ are each independently fluorine or a $C_1$-$C_6$ perfluoroalkyl group, $L^A$ is a single bond or forms an ester bond, sulfonate bond, carbonate bond or carbamate bond with the vicinal oxygen atom, $Z^+$ is a sulfonium cation having the formula (2) or an iodonium cation having the formula (3):

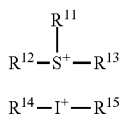

(2)

(3)

wherein $R^{11}$, $R^{12}$ and $R^{13}$ are each independently a $C_1$-$C_{20}$ straight, branched or cyclic monovalent hydrocarbon group which may contain a heteroatom, any two of $R^{11}$, $R^{12}$ and $R^{13}$ may bond together to form a ring with the sulfur atom in the formula, $R^{14}$ and $R^{15}$ are each independently a $C_1$-$C_{20}$ straight, branched or cyclic monovalent hydrocarbon group which may contain a heteroatom.

2. The onium salt of claim 1 wherein $R^{f1}$ and $R^{f2}$ are trifluoromethyl.

3. The onium salt of claim 1 wherein $Z^+$ is a sulfonium cation of formula (2).

4. The onium salt of claim 1 wherein $L^A$ is a single bond or forms a sulfonate bond with the vicinal oxygen atom.

5. The onium salt of claim 1 wherein $L^A$ is a single bond and $R^0$ is hydrogen.

6. The onium salt of claim 1 wherein the anion moiety of the onium salt is selected from the group consisting of the following formulae:

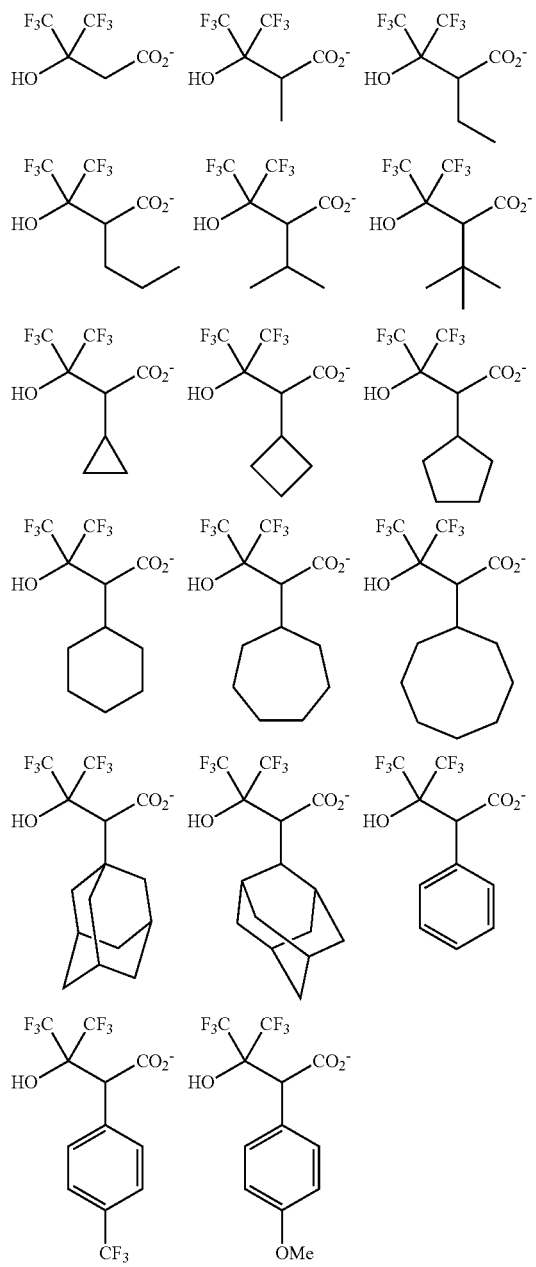

143
-continued
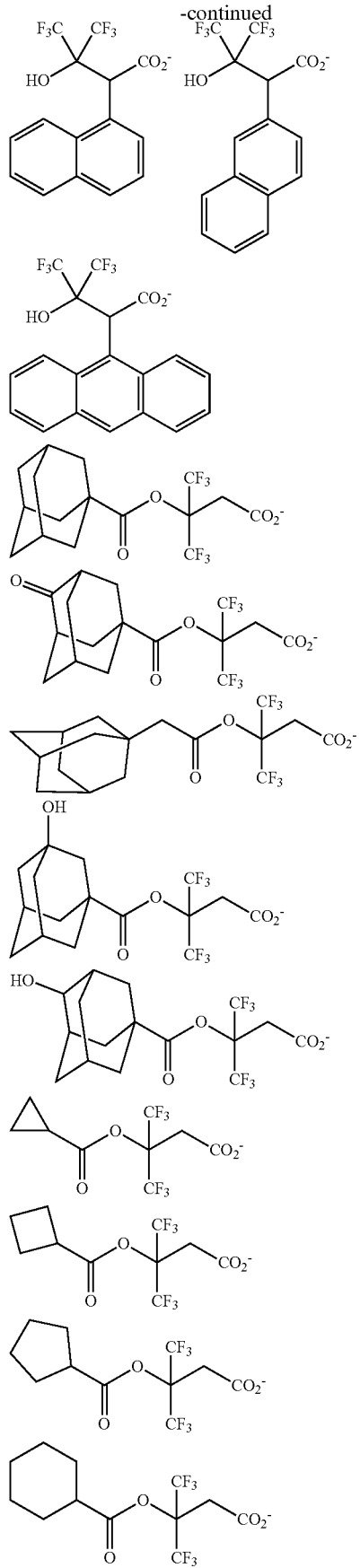
144
-continued
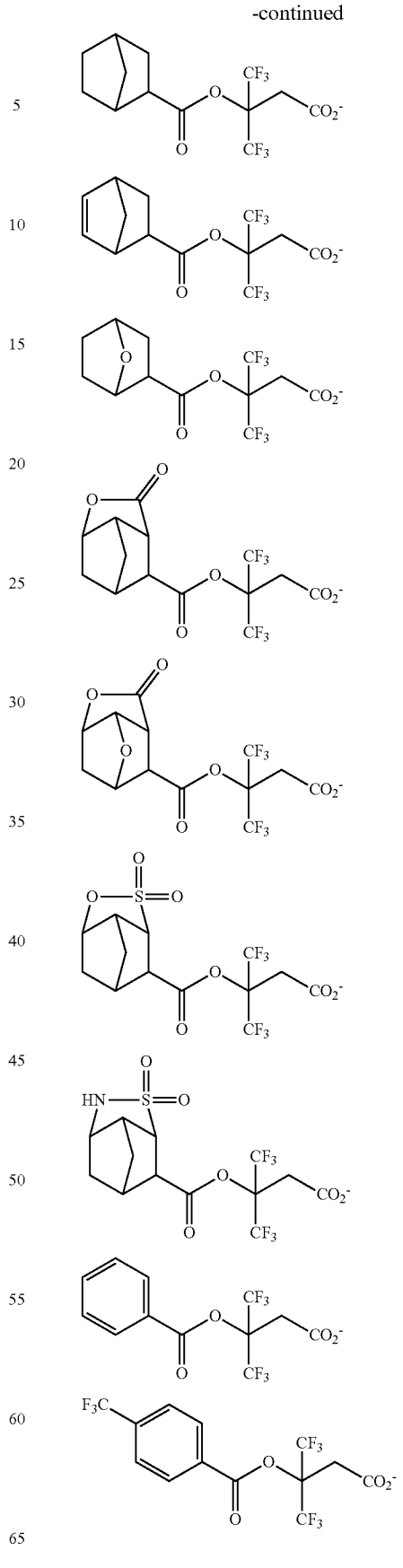

-continued

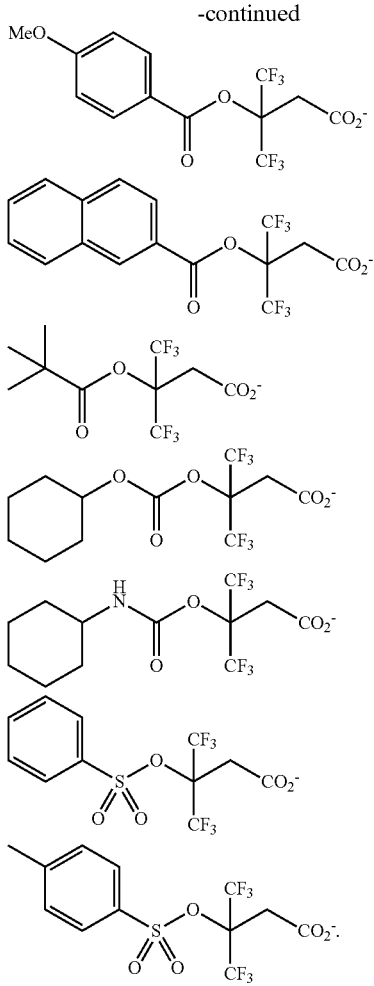

7. An acid diffusion inhibitor comprising the carboxylic acid onium salt of claim 1.

8. A chemically amplified resist composition comprising (A) the acid diffusion inhibitor of claim 7, (B) a base resin, (C) a photoacid generator, and (D) an organic solvent, wherein
said base resin contains a polymer comprising recurring units having the formula (a) and recurring units having the formula (b):

(a)

(b)

wherein $R^A$ is hydrogen, methyl or trifluoromethyl, $Z^A$ is a single bond, phenylene, naphthylene or (backbone)—C(=O)—O—Z'—, Z' is a $C_1$-$C_{10}$ straight, branched or cyclic alkylene group which may contain a hydroxyl moiety, ether bond, ester bond, or lactone ring, or a phenylene or naphthylene group, $X^A$ is an acid labile group, and $Y^A$ is hydrogen or a polar group having at least one structure selected from the group consisting of hydroxyl, cyano, carbonyl, carboxyl, ether bond, ester bond, sulfonate bond, carbonate bond, lactone ring, sultone ring, and carboxylic anhydride.

9. The resist composition of claim 8 wherein said polymer further comprises recurring units of at least one type selected from recurring units having the formulae (c1) to (c3):

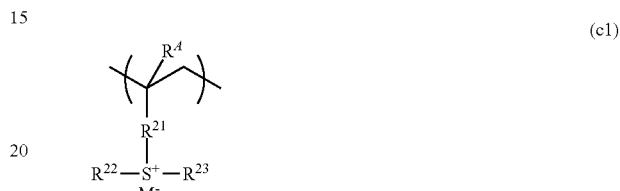

(c1)

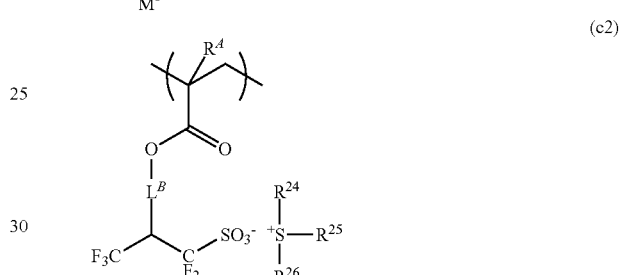

(c2)

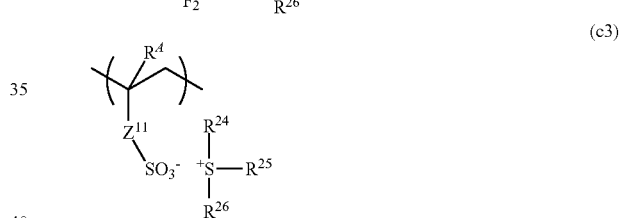

(c3)

wherein $R^A$ is as defined above,
$R^{21}$ is a single bond, phenylene, —O—$R^{31}$—, or —C(=O)—$Z^{22}$—$R^{31}$—, $Z^{22}$ is —O— or —NH—, $R^{31}$ is a $C_1$-$C_6$ straight, branched or cyclic alkylene group, $C_2$-$C_6$ straight, branched or cyclic alkenylene group or phenylene group, which may contain a carbonyl (—CO—), ester (—COO—), ether (—O—) or hydroxyl moiety,
$L^B$ is a single bond or —$Z^{33}$—C(=O)—O—, $Z^{33}$ is a $C_1$-$C_{20}$ straight, branched or cyclic divalent hydrocarbon group which may contain a heteroatom,
$Z^{11}$ is a single bond, methylene, ethylene, phenylene, fluorinated phenylene, —O—$R^{32}$—, or —C(=O)—$Z^{44}$—$R^{32}$—, $Z^{44}$ is —O— or —NH—, $R^{32}$ is a $C_1C_6$ straight, branched or cyclic alkylene, $C_2$-$C_6$ straight, branched or cyclic alkenylene or phenylene group, which may contain a carbonyl, ester, ether or hydroxyl moiety,
$R^{22}$ to $R^{26}$ are each independently a $C_1$-$C_{20}$ straight, branched or cyclic monovalent hydrocarbon group which may contain a heteroatom, or any two of $R^{21}$, $R^{22}$ and $R^{23}$ may bond together to form a ring with the sulfur atom in the formula, any two of $R^{24}$, $R^{25}$ and $R^{26}$ may bond together to form a ring with the sulfur atom in the formula, and
$M^-$ is a non-nucleophilic counter ion.

10. The resist composition of claim 8 wherein component (C) is a photoacid generator having the formula (4) or (5):

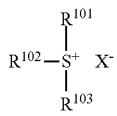   (4)

wherein $R^{101}$, $R^{102}$ and $R^{103}$ are each independently a $C_1$-$C_{20}$ straight, branched or cyclic monovalent hydrocarbon group which may contain a heteroatom, any two of $R^{101}$, $R^{102}$ and $R^{103}$ may bond together to form a ring with the sulfur atom to which they are attached, and X⁻ is an anion selected from the formulae (4A) to (4D):

   (4A)

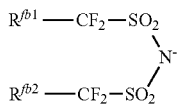   (4B)

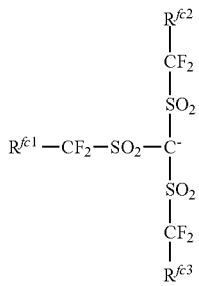   (4C)

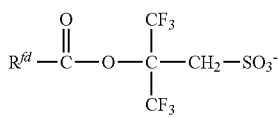   (4D)

wherein $R^{fa}$, $R^{fb1}$, $R^{fb2}$, $R^{fc1}$, $R^{fc2}$, and $R^{fc3}$ are each independently fluorine or a $C_1$-$C_{40}$ straight, branched or cyclic monovalent hydrocarbon group which may contain a heteroatom, $R^{fb1}$ and $R^{fb2}$, or $R^{fc1}$ and $R^{fc2}$ may bond together to form a ring with the carbon atoms to which they are attached and the carbon atom therebetween, $R^{fd}$ is a $C_1$-$C_{40}$ straight, branched or cyclic monovalent hydrocarbon group which may contain a heteroatom,

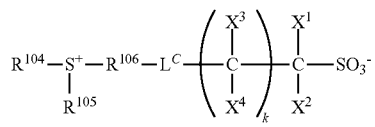   (5)

wherein $R^{104}$ and $R^{105}$ are each independently a $C_1$-$C_{30}$ straight, branched or cyclic monovalent hydrocarbon group which may contain a heteroatom, $R^{106}$ is a $C_1$-$C_{30}$ straight, branched or cyclic divalent hydrocarbon group which may contain a heteroatom, any two of $R^{104}$, $R^{105}$ and $R^{106}$ may bond together to form a ring with the sulfur atom to which they are attached, $L^C$ is a single bond, ether bond, or a $C_1$-$C_{20}$ straight, branched or cyclic divalent hydrocarbon group which may contain a heteroatom, $X^1$, $X^2$, $X^3$ and $X^4$ are each independently hydrogen, fluorine or trifluoromethyl, with the proviso that at least one of $X^1$, $X^2$, $X^3$ and $X^4$ is a substituent other than hydrogen, and k is an integer of 1 to 3.

11. The resist composition of claim 8, further comprising (E) a nitrogen-containing compound.

12. The resist composition of claim 8, further comprising (F) a surfactant which is insoluble or substantially insoluble in water and soluble in alkaline developer and/or a surfactant which is insoluble or substantially insoluble in water and alkaline developer.

13. A pattern forming process comprising the steps of applying the chemically amplified resist composition of claim 8 onto a substrate, prebaking to form a resist film, exposing the resist film to KrF excimer laser, ArF excimer laser, EB or EUV through a photomask, baking, and developing the exposed resist film in a developer.

14. The pattern forming process of claim 13 wherein the exposing step is by immersion lithography wherein a liquid having a refractive index of at least 1.0 is interposed between the resist film and a projection lens.

15. The pattern forming process of claim 14, further comprising the step of forming a protective film on the resist film, and in the immersion lithography, the liquid is interposed between the protective firm and the projection lens.

* * * * *